(12) United States Patent
Laemmli et al.

(10) Patent No.: US 7,790,379 B2
(45) Date of Patent: Sep. 7, 2010

(54) MAPPING OF PROTEINS ALONG CHROMATIN BY CHROMATIN CLEAVAGE

(75) Inventors: Ulrich Karl Laemmli, Onex (CH); Manfred Schmid, Risskov (DK)

(73) Assignee: Universite de Geneve, Geneva (CH)

( * ) Notice: Subject to any disclaimer, the term of this patent is extended or adjusted under 35 U.S.C. 154(b) by 693 days.

(21) Appl. No.: 11/437,163

(22) Filed: May 19, 2006

(65) Prior Publication Data

US 2007/0009937 A1    Jan. 11, 2007

Related U.S. Application Data

(60) Provisional application No. 60/683,264, filed on May 19, 2005.

(51) Int. Cl.
*G01N 33/53* (2006.01)
(52) U.S. Cl. ............................................. 435/6; 435/7.1
(58) Field of Classification Search ........................ None
See application file for complete search history.

(56) References Cited

U.S. PATENT DOCUMENTS 6,027,880 A * 2/2000 Cronin et al. .................. 435/6

OTHER PUBLICATIONS

Bartel, P. L. et al. (1996) "A Protein Linkage Map of *Escherichia coli* Bacteriophage T7," *Nat. Genet.* 12: 72-77.
Belotserkovskaya, R. et al. (2004) "Transcription Through Chromatin: Understanding a Complex FACT," *Biochim. Biophys. Acta.* 1677: 87-99.
Chien, C.-T. et al. (1993) "Targeting of SIR1 Protein Establishes Transcriptional Silencing at *HM* Loci and Telomeres in Yeast," *Cell* 75: 531-541.
Giraud-Panis, M.-J. et al. (1995) "The Modular Character of a DNA Junction-resolving Enzyme: A Zinc-binding Motif in Bacteriophage T4 Endonuclease VII," *J. Mol. Biol.* 252: 596-610.
Ishii, K. et al. (2003) "Structural and Dynamic Functions Establish Chromatin Domains," *Mol. Cell.* 11: 237-248.
Katou, Y. et al. (2003) "S-phase Checkpoint Proteins Tof1 and Mrc1 Form a Stable Replication-pausing Complex," *Nature* 424: 1078-1083.
Lee, J.-S. et al. (1998) "Studying the Recruitment of Sp1 to the β-globin Promoter With an in Vivo Method: Protein Position Identification with Nuclease Tail (Pin*Point) ," *Proc. Natl. Acad. Sci. U.S.A.* 95: 969-974.
Lee, T. I. et al. (1998) "Regulation of Gene Expression by TBP-associated Proteins," *Genes Dev.* 12: 1398-1408.
Longtine, M. S. et al. (1998) "Additional Modules for Versatile and Economical PCR-based Gene Deletion and Modification in *Saccharomyces cerevisiae*," *Yeast* 14: 953-961.

(Continued)

*Primary Examiner*—Jacob Cheu
(74) *Attorney, Agent, or Firm*—John P. White; Cooper & Dunham LLP

(57) ABSTRACT

The present invention is directed to a method for localizing, in chromatin or DNA, the binding loci of a chromatin or DNA binding protein comprising the following steps:
  a) tethering, directly or indirectly, an enzyme with regulatable activity to said chromatin binding protein,
  b) transiently activating the regulatable enzymatic activity bound to the targeted chromatin and
  c) mapping the enzymatically-modified genomic sites introduced by the enzyme into the chromatin.

According to an embodiment of the invention, the regulatable enzyme is a regulatable protease. The mapping step may be carried out on specific DNA fragments, or on a chromosome-wide scale or a genome-wide scale.

The present invention is also directed to kits for carrying out the methods of the invention.

56 Claims, 15 Drawing Sheets

OTHER PUBLICATIONS

Orlando, V. (2000) "Mapping Chromosomal Proteins in Vivo by Formaldehyde-crosslinked-chromatin Immunoprecipitation," *Trends Biochem. Sci.* 25: 99-104.

Rusche, L. N. et al. (2003) "The Establishment, Inheritance, and Function of Silenced Chromatin in *Saccharomyces cerevisiae*," *Annu. Rev. Biochem.* 72: 481-516.

Schmid, M. et al. "Nup-PI: The Nucleopore-Promoter Interaction of Genes in Yeast," *Molecular Cell* 21: 379-391 and Supplemental Data (15 pages).

Shortle, D. (1983) "A Genetic System for Analysis of Staphylococcal Nuclease," *Gene* 22: 181-189.

Telford, D. J. et al. (1989) "Micrococcal Nuclease: Its Specificity and Use for Chromatin Analysis," *Int. J. Biochem.* 21: 127-137.

van Steensel, B. et al. (2001) "Chromatin Profiling Using Targeted DNA Adenine Methyltransferase," *Nat Genet.* 27: 304-308.

van Steensel, B. et al. (2000) "Identification of in Vivo DNA Targets of Chromatin Proteins Using Tethered Dam Methyltransferase," *Nat. Biotechnol.* 18: 424-428.

Zhao, K. et al. (1995) "Visualization of Chromosomal Domains With Boundary Element-Associated Factor BEAF-32," *Cell* 81: 879-889.

Schmid, M. et al. (2004) "ChIC and ChEC: Genomic Mapping of Chromatin Proteins," *Molecular Cell* 16: 147-157.

\* cited by examiner

MAPPING OF PROTEINS ALONG CHROMATIN BY CHROMATIN CLEAVAGE

This application claims the benefit of U.S. Provisional Application No. 60/683,264, filed May 19, 2005, the contents of which are hereby incorporated by reference into this application.

FIELD OF THE INVENTION

The present invention is in the domain of cellular biology; it relates to a method for mapping the genomic binding loci of chromatin protein with a very high resolution.

BACKGROUND OF THE INVENTION

Most cellular processes, such as DNA replication, transcription and chromosome dynamics, are regulated by binding of protein complexes to specific cis-acting elements of chromatin templates.

Many of these interactions have recently been studied with the aid of the chromatin immunoprecipitation technique (ChIP), which is a versatile, widely used method to localize bound proteins to genomic loci with a resolution of about 1 kb (reviewed by Orlando, 2000). ChIP is based on formaldehyde fixation of cells followed by immunoprecipitation of fragmented chromatin with specific antibodies. One basic assumption of ChIP is that immunoprecipitation is applied to soluble (or solubilized) chromatin that consists of linear or specifically branched, not randomly crosslinked, chromatin fragments. Toward this goal, fixed cells are exposed to a combined action of sonication (sometimes nucleases) and denaturing agents. This fragmentation-solubilization step is followed by centrifugation to remove large insoluble material prior to the immunoprecipitation step. Although rarely stated, many structural-type chromatin proteins remain quite insoluble and significant amounts are lost into the pellet during centrifugation.

The ChIP method is afflicted with several problems and limitations. Often this method yields results associated with a high background, where the signal to noise ratio is low. This background has different causes such as, limited antibody specificity, non-specific chromatin aggregation and fixation artifacts. The chemical fixation step, usually by formaldehyde, is necessary as to 'freeze' proteins of interest to chromatin to allow fragmentation by sonication. But fixation is an uncontrolled step, that also leads to non-specific crosslinking of chromatin fragments into branched aggregates, it also yields 'nuclear crumbs' by shattering the fixed nucleus by sonication that are not removed by the centrifugation step. Hence, the basic assumption, unbranched chromatin fragments, is not necessarily met.

In consequence, the data obtained by ChIP, an in vitro method, do not necessary reflect the in vivo situation.

Moreover, ChIP analyses with insoluble-type proteins appear afflicted with increased background, supposedly arising by non-specific crosslinking of chromatin into branched aggregates or 'nuclear crumbs'.

An alternative technique for identification of DNA loci that interact in vivo with specific nuclear proteins is named DamID (van Steensel and Henikoff, 2000). In this method, the adenine methyltransferase (Dam) for *E. coli* is expressed as a fusion protein, X-Dam, in vivo. X is a protein of interest bound to chromatin that one wants to genomically map. The targeted, chromatin bound X-Dam, methylates in vivo adenine (N6 position) at GATC sequences, which occur every 200-300 bp. A restriction enzyme, DpnII, is then used to measure the extent of methylation. This enzyme cleaves the DNA, if a Dam site is unmethylated, while it does not cleave, if the site is methylated. Hence, to map a X-Dam protein genomically, one measures around putative genomic targets of X, the relative cleavability of Dam sites using either PCR and Southern blotting.

Main disadvantages of DamID are poor resolution and unregulated expression. First, Dam sites only occur on average every 200-300 bp, so sampling distances are large; the DNA in-between remains unsampled. Second, since methylation occurs continuously, it is not regulated ON/OFF, methylation occurs in a large DNA neighbourhood (several kb) surrounding genomic binding sites for X.

Another alternative method, which only works in vivo, is based on the technique named "PIN*POINT" (Lee et al, 1998). According to this technique, a fusion gene product X-FokI is expressed in the cell, wherein X is the chromatin protein under study and FokI stands for the nuclease moiety of the endonuclease FokI. The binding of the X protein to DNA is made detectable by the nuclease-induced cleavage near the binding site of X, by primer extension or ligation-mediated PCR.

However, expression of an active, non-regulatable nuclease in vivo is very damming to the cell. In vivo DNA breaks accumulated during the entire expression period. This induces the DNA damage checkpoint pathway, which alters the cell physiology dramatically.

Therefore, in view of the drawbacks of the available techniques there is a need for a technique which combines a high resolution mapping (at most around 100 base pairs or even less) with confidence and also a high sensitivity to biological changes without interferences by artefacts linked to the method.

The technique must also preferably be adapted for in vivo and in vitro uses, have a reduced reaction time and be suitable for a genome-wide mapping, even for genome as complex as the human genome.

SUMMARY OF THE INVENTION

The present invention concerns methods for localizing the binding loci of a chromatin or DNA binding protein. The methods of the invention comprise the following steps:
  a) Tethering, directly or indirectly, an enzyme having a regulatable activity to a chromatin or DNA binding protein of interest,
  b) Transiently activating the regulatable enzyme bound to the targeted chromatin and
  c) Mapping of the genomic sites in the chromatin which have been enzymatically modified by the regulatable enzyme.

According to the invention, a regulatable enzymatic activity is thus targeted to the locus (or loci) where a chromatin protein binds, by tethering the enzyme to the chromatin or DNA binding protein or to the chromatin or DNA binding domain of said protein.

During the tethering step, the regulatable enzyme is inactive or maintained in an inactive state. According to the invention, the enzyme may be rendered active at any time by changing the conditions which maintain the enzyme in an inactive state. This transition from inactive to active state may be triggered by the addition of an effector (e.g. chemical compound or peptide) or by switching the temperature for example.

According to the present invention, after activation, the enzyme introduces modification of its substrate into the targeted chromatin, in the vicinity of the locus or loci where the chromatin protein binds the chromatin. By mapping these enzymatically modified sites, it is thus possible to identify precisely the binding regions of the chromatin protein of interest.

Due to the regulatable feature of the enzymatic activity, the activation is transient and the period of activation can be precisely defined.

BRIEF DESCRIPTION OF THE DRAWINGS

The invention may be further illustrated by reference to the accompanying drawings wherein.

(1A) The major steps of the ChIC procedure are illustrated.

(Step 1) Binding of the primary antibody (AB) and subsequent centrifugation-washing steps.

(Step 2) Binding of the secondary AB and subsequent washing steps.

(Step 3) Binding of the fusion protein pA-MN to the secondary AB and final washing steps.

(Step 4) Activation of the nuclease MN moiety of pA-MN with $Ca^{2+}$ ions. Double-stranded DNA breaks are expected to be introduced adjacent to the genomic position of the antigen.

(1B) Immuno-blots of ChIC experiments with fixed crude nuclei derived from cells expressing either the antigen Gbd-myc13 (strain KIY64 transformed with pGBC11-myc13), Sir3-myc13 (strain KIY67) or no antigen (no myc, strain KIY64). The blots reveal as indicated, the antigens (top panels) and the heavy chains of the ABs (IgH) and pA-MN (bottom panels) at the final steps of the procedure. T (lanes 1, 5, 9) shows the proteins at step 3. S (lanes 2, 6, 10) represents the first supernatant fraction following step 3. B (lanes 3, 7, 11) shows the components bound in the final fraction of crude nuclei at step 4. As control, free pA-MN was added to KIY64 nuclei (no myc) at step 4. F (lanes 4, 8, 12) are aliquots of the free pA-MN containing samples (KIY64, no myc).

Figure 1:
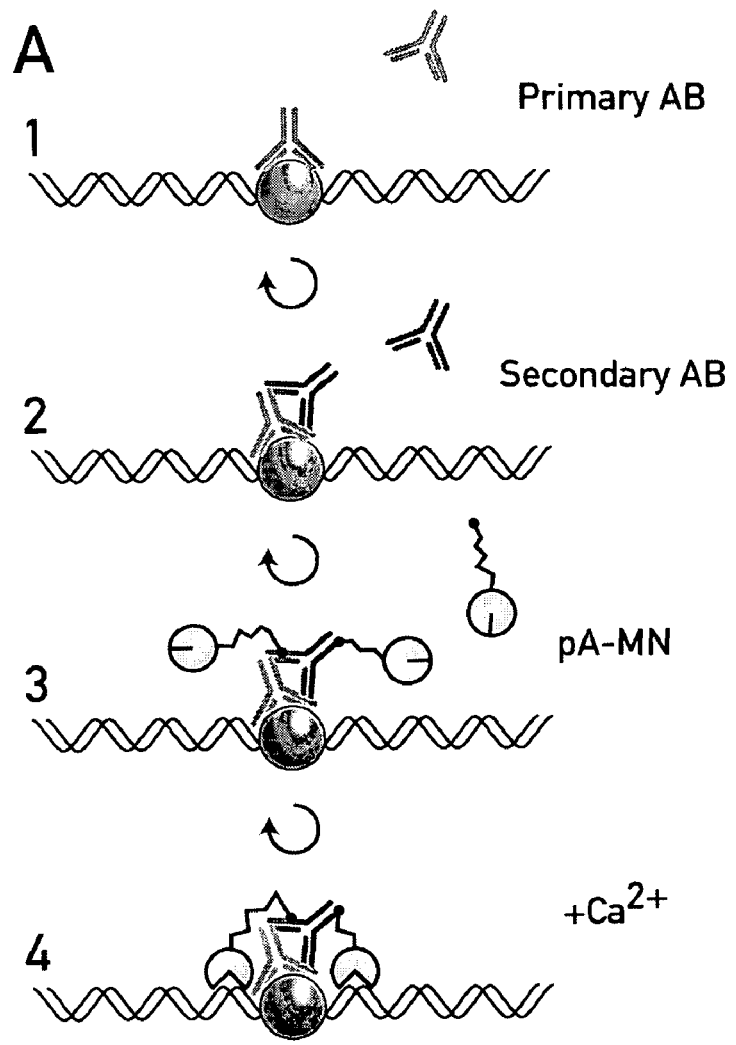
FIG. 1 depicts an outline of the ChIC method.
Figure 1:
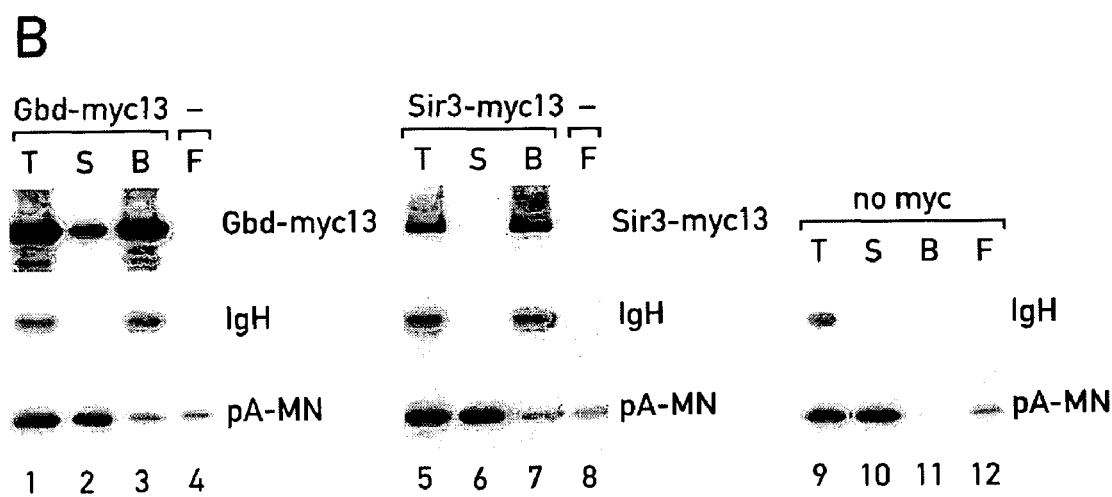
Figure 2:
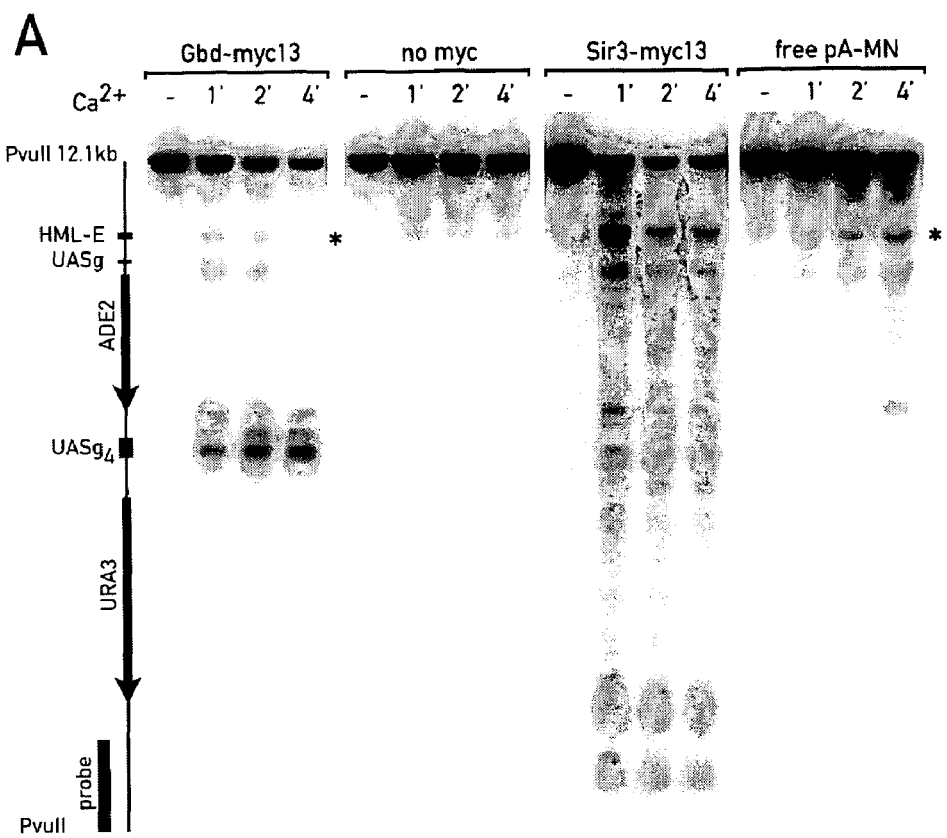
Figure 2:
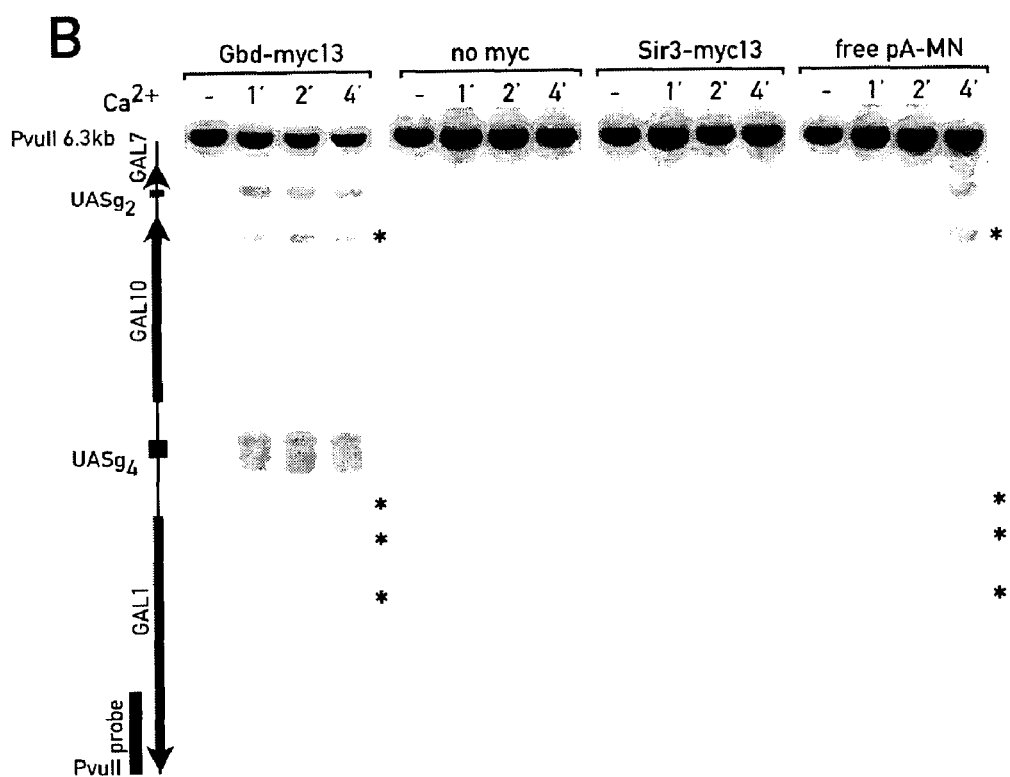

FIG. 2 represents the genomic localization of Gbd-myc13 and Sir3-myc13 by ChIC DNA digestion patterns of the ChIC experiment presented in FIG. 1B with yeast strains expressing Gbd-myc13, Sir3-myc13 or no antigen, as indicated. Control digests were carried out by adding free pA-MN to nuclei at step 4. DNA samples were Southern blotted by indirect end-labeling at two genomic loci. Digestion times following activation of pA-MN nuclease with $Ca^{2+}$ ions are shown. The genomic maps and position of probes (table 3) are depicted on the left. Major HS sites (nuclease hypersensitive sites) are marked with asterisks.

(2A) ChIC patterns at the modified HML locus.

(2B) ChIC patterns at the GAL1-10 locus.

Figure 3:
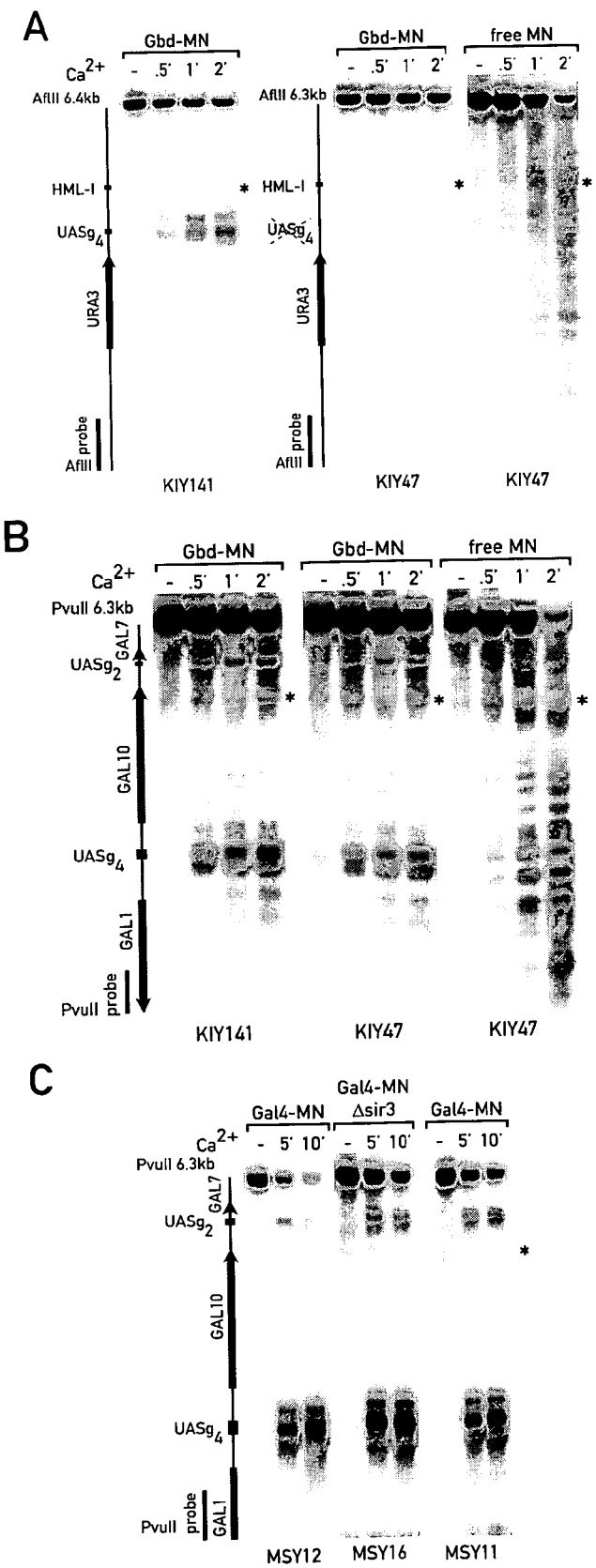

FIG. 3 represents an in vitro ChEC experiments for Gbd-MN and Gal4-MN

In vitro ChEC patterns are shown for Gbd-MN and Gal4-MN at a modified HML locus and at the GAL1-10 locus. Genomic maps of these loci and the position of the probes (Table 3) are depicted. HS sites are indicated by asterisks.

(3A) In vitro ChEC patterns for Gbd-MN in strains KIY141 and KIY47 containing differently modified HML loci. It is to be noted that the UASg sites of strain KIY141 are deleted in KIY47. The digestion pattern of free MN was obtained from strain KIY47 that expresses Gbd without MN.

(3B) DNA samples of (3A) probed at the GAL1-10 locus.

Figure 6:
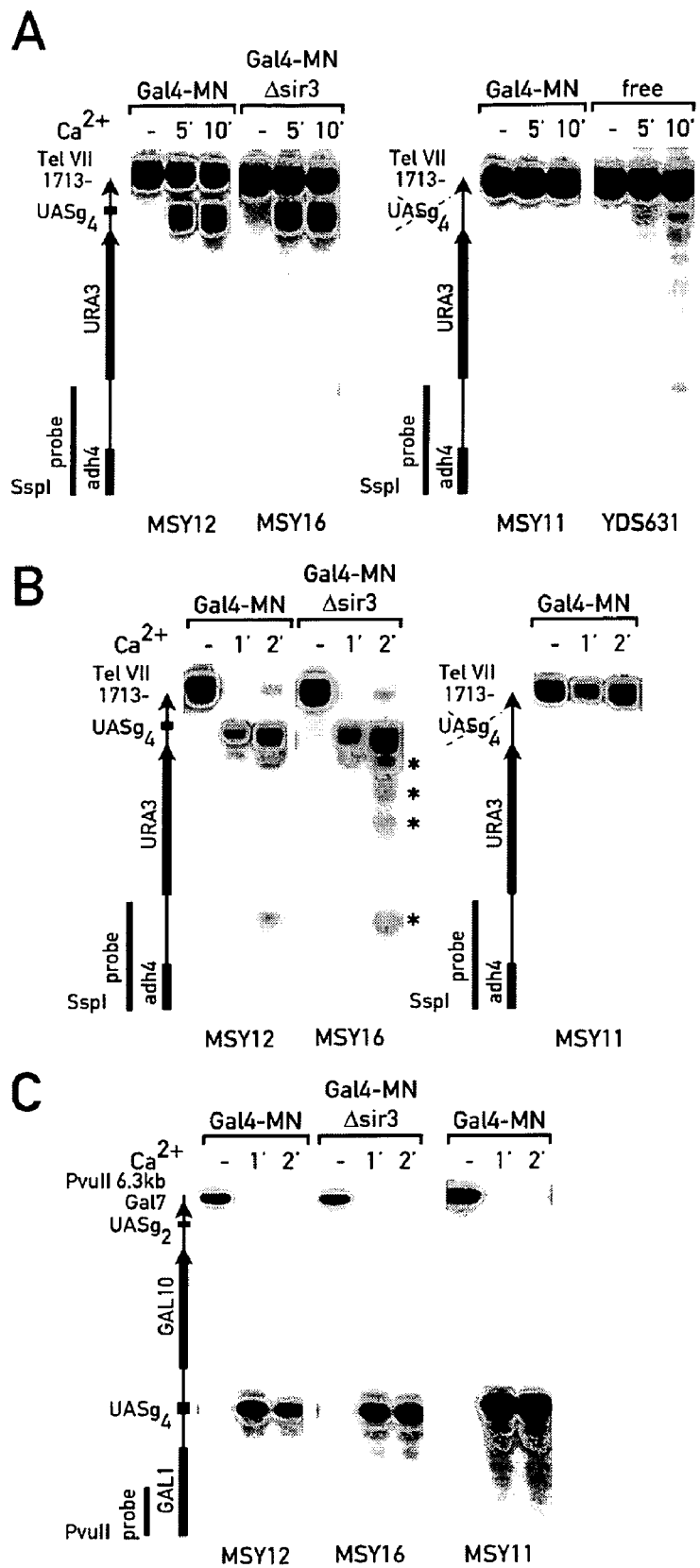

(3C) In vitro ChEC patterns of Gal4-MN at the GAL1-10 locus in strains (MSY12, MSY16 and MSY11) carrying different telomere-linked constructs presented in FIG. 6. The SIR3 gene (Δsir3) was deleted in strain MSY16.

Figure 4:
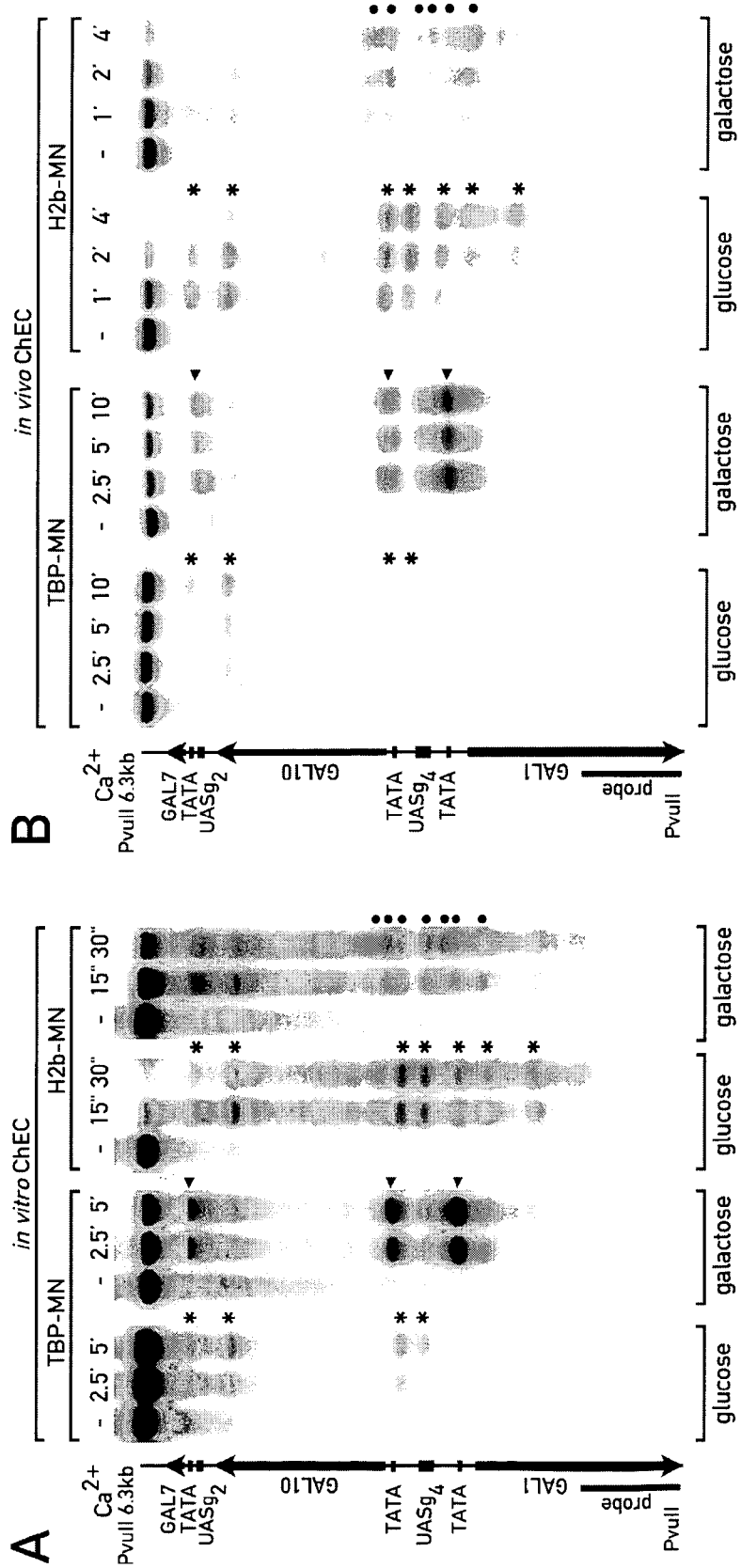

FIG. 4 illustrates the recruitment of the TATA-box binding protein The in vitro (4A) and in vivo ChEC (4B) patterns of TBP-MN (strain TD348) and H2b-MN (strain TD347) were compared at the GAL1-10 locus following activation of this locus by growth in galactose. The repressed ChEC patterns of this locus were obtained by growth in glucose. Genomic maps including position of the probes (Table 3) and TATA boxes in the promoters of the GAL1, GAL7 and GAL10 genes are indicated. Specific cleavage bands at TATA boxes are indicated by arrowheads, major HS sites with asterisks and mobilized nucleosomes with dots.

(4A) In vitro ChEC patterns obtained following addition of $Ca^{2+}$ ions at 30° C. for the times indicated to fixed cells lyzed with glass beads.

(4B) In vivo ChEC patterns obtained following addition of $Ca^{2+}$ ions at 0° C. for the times indicated to native cells permeabilized with digitonin.

Figure 5:
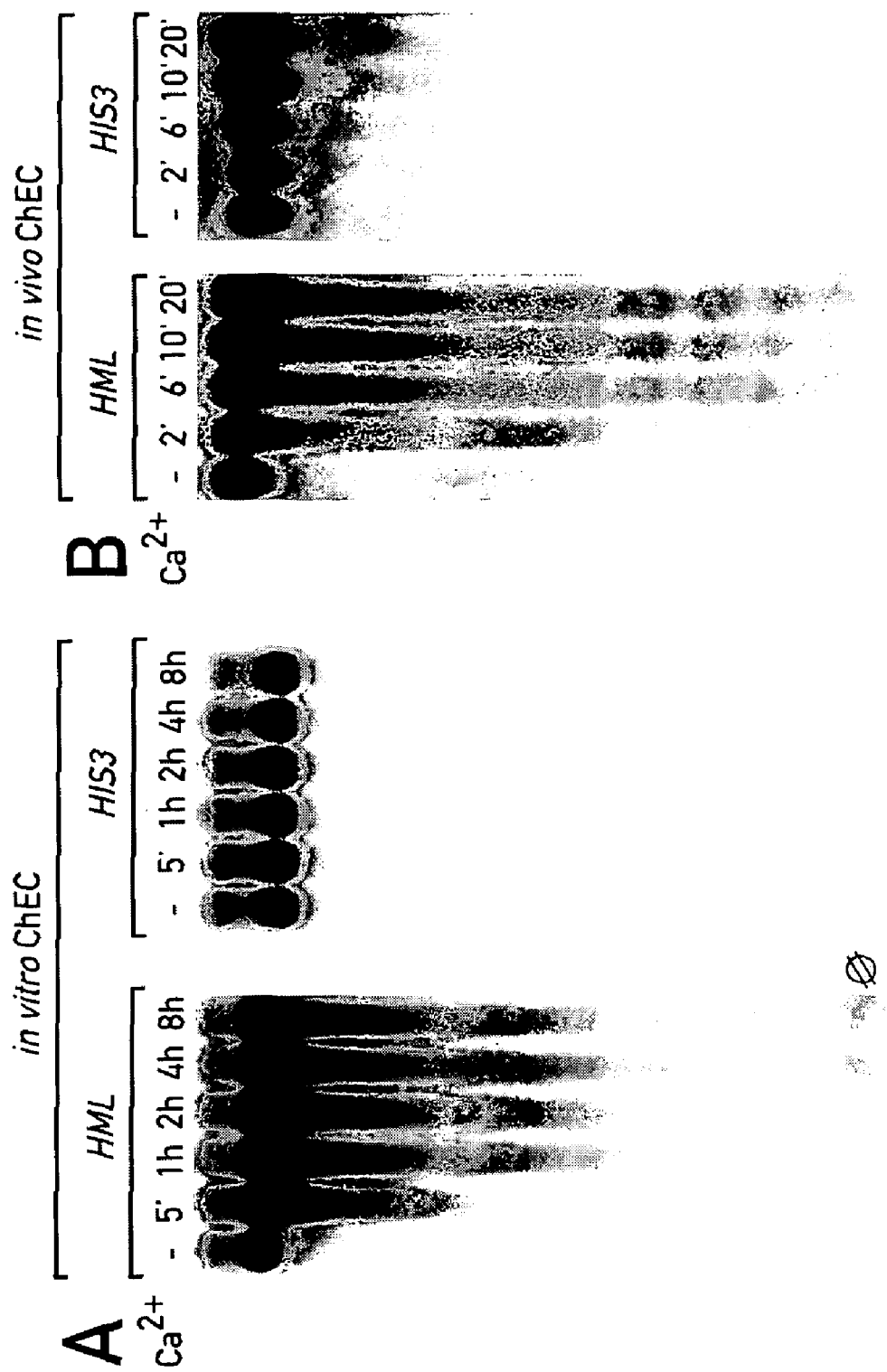

FIG. 5 shows that ChEC of Sir3-MN yields a nucleosomal pattern at HML

In vitro (5A) and in vivo (5B) ChEC patterns of a strain expressing Sir3-MN (TD345). ChEC was done as described in FIG. 4 except that incubation with $Ca^{2+}$ was done at 30° C. in either case. It is to be noted that longer digestion times were used for fixed cells (5A). DNA samples were not probed by indirect end-labeling, but DNA was loaded without restriction digestion and hybridized with probes encompassing the HML or HIS3 locus (Table 3). The position of mono-nucleosomes is indicated.

FIG. 6 shows in vitro (A) and in vivo (B & C) ChEC experiments with three yeast strains expressing Gal4-MN that harbour different telomere constructs. Strains MSY12 and MSY16 have a telomere-linked URA3 gene with 4 UASg sites inserted downstream toward the telomere (see maps). The SIR3 gene was deleted (Δsir3) in strain MSY16.

Strain MSY11 lacks the downstream UASg sites. Positions of the probes (Table 3) are depicted on the genomic maps. Subsidiary cleavage sites are indicated by asterisks.

(A) In vitro ChEC patterns at the telomere in the strains indicated. Digestion times at 30° C. are shown. The digestion pattern of free MN obtained with strain YDS631 is shown. This strain is identical to MSY11 but expressed the endogenous GAL4 gene lacking an MN-tag.

(B) In vivo ChEC pattern of the same strains as in (A). Digestion times at 30° C. are indicated. It must be noted that the extent of digestion is considerably higher under these conditions.

(C) DNA samples of (B) probed at the GAL1-10 locus.

Figure 7:
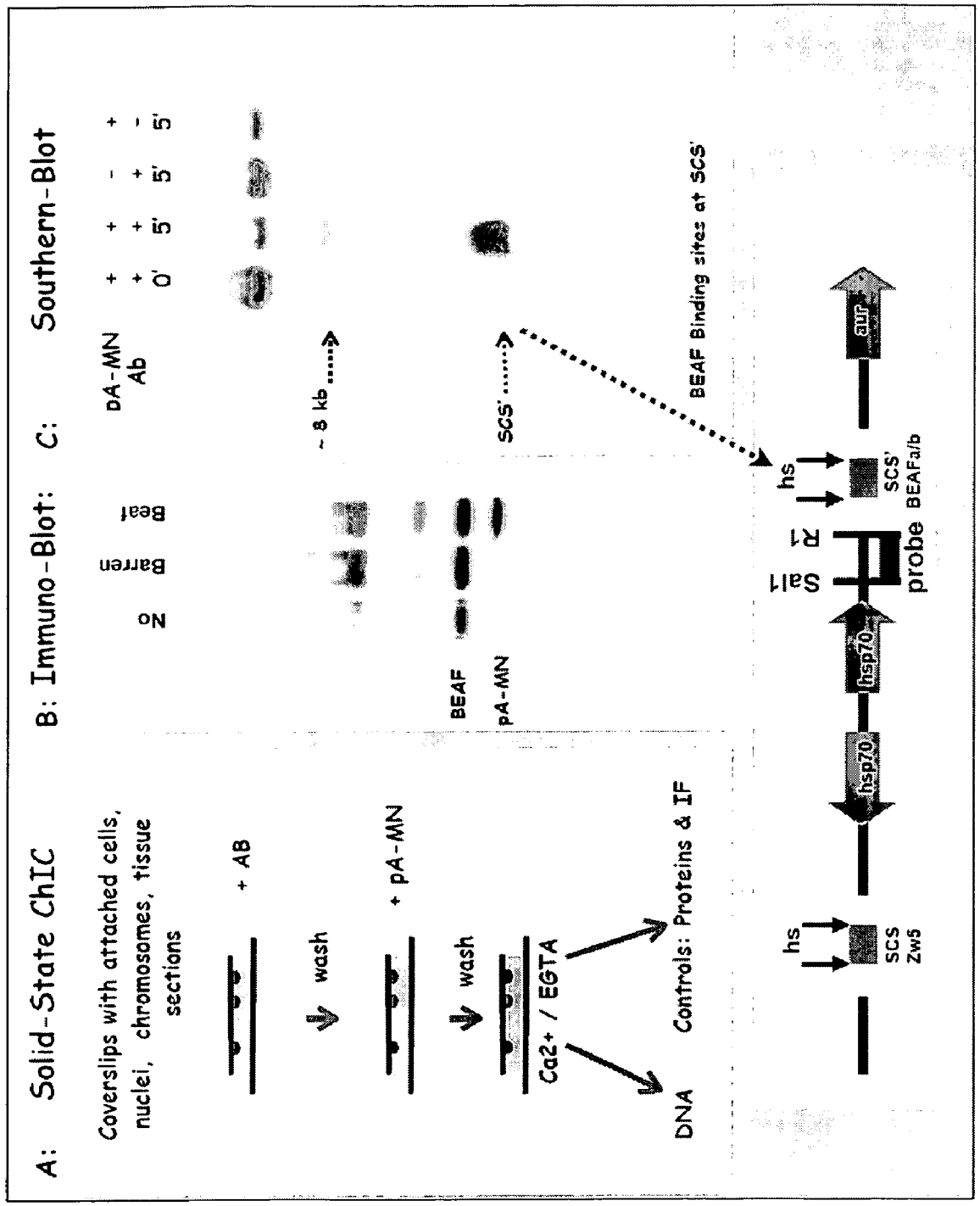

FIG. 7 represents the mapping of BEAF by Solid-State ChIC in *Drosophila* Nuclei Panel 7A: Generic outline of the solid-state ChIC (ss-ChIC) procedure. By way of example: Kc nuclei were attached to pre-coated coverslips and stained with the primary Abs (anti-BEAF and anti-dBarren). Following washing steps, pA-MN was applied. Washing and incubation steps were carried out by floating and transfer of grids onto drops deposited on Parafilm. Cleavage was induced and stopped by addition of $Ca^{2+}$ and EGTA, respectively. Additional steps that might be needed to enhance specificity of binding are not shown.

Panel 7B: Immuno-blot of proteins bound at the final step. The blot shows the antigen BEAF in all lanes and that pA-MN is only retained if a primary Ab (anti-BEAF or anti-dBarren) was added (indicated at top).

Panel 7C: Southern blot using indirect end-labeling with the probe indicated in the map (bottom). This probe detects cleavage sites from the SaI1 site toward the right. As observed in the blot, cleavage occurs at the known scs' site (arrow) and at an unknown location about 8 kb distal (arrow). The digestion times and added components are indicated at the top. It is to be noted that cleavage is only observed following incubation (5'), if both the specific Abs and pA-MN were added (indicated).

Figure 8:
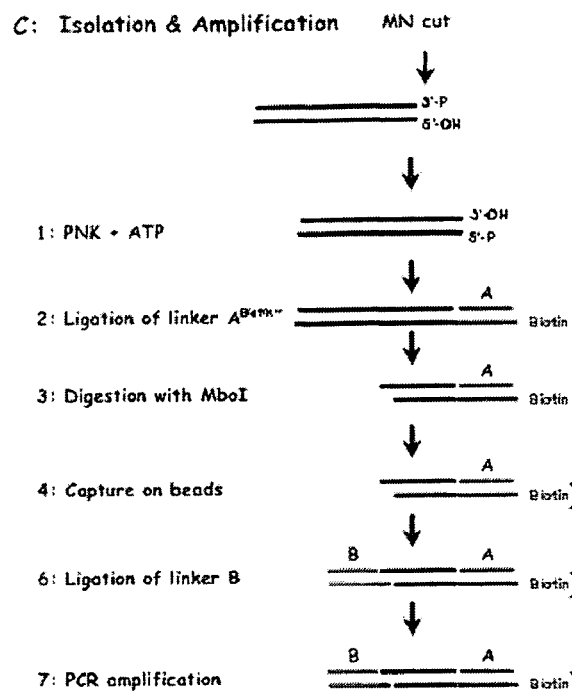

FIG. 8 represents the amplification of DNA flanking MN-cuts.

(A) Panel A: Common nicks terminate with 3'OH residues, while the MN-cuts contain 3' phosphates (P). It is therefore possible to selectively block nicks, to render them unavailable for ligation and to subsequently phosphorylate MN-cuts. This is outlined next:

(B) Panel B: Random nicks are blocked from ligation by the addition of a dideoxy-nucleotide with terminal transferase (TdT) using a ddNTP mixture.

(C) Panel C: Outline of the individual steps of isolation and amplification of DNA flanking MN-cuts:

Step 1, Phosphorylation: MN-cuts introduced by ChIC or ChEC are phosphorylated with T4 polynucleotide kinase (PNK).

Step 2, Ligation of linker A: Biotinylated linker A is ligated to MN-cuts and unbound linker is removed.

Step 3, Digestion: DNA is digested with Mbo I and liberated DNA fragments removed.

Step 4, Beads: Primer A bound to MN cuts is tethered to strepavidin-magnetic beads and unbound DNA is washed away. The bound fraction is enriched for DNA flanking MN-cuts.

Step 5, Ligation of linker B: Ligation of linker B to the Mbo I sites of bead-bound DNA and removal of excess linker.

Step 6, PCR amplification: Amplification of bead-bound DNA by PCR using primers specific for the linkers A and B. This amplified DNA, adequately labeled, serves as the hybridization probe.

Figure 9:
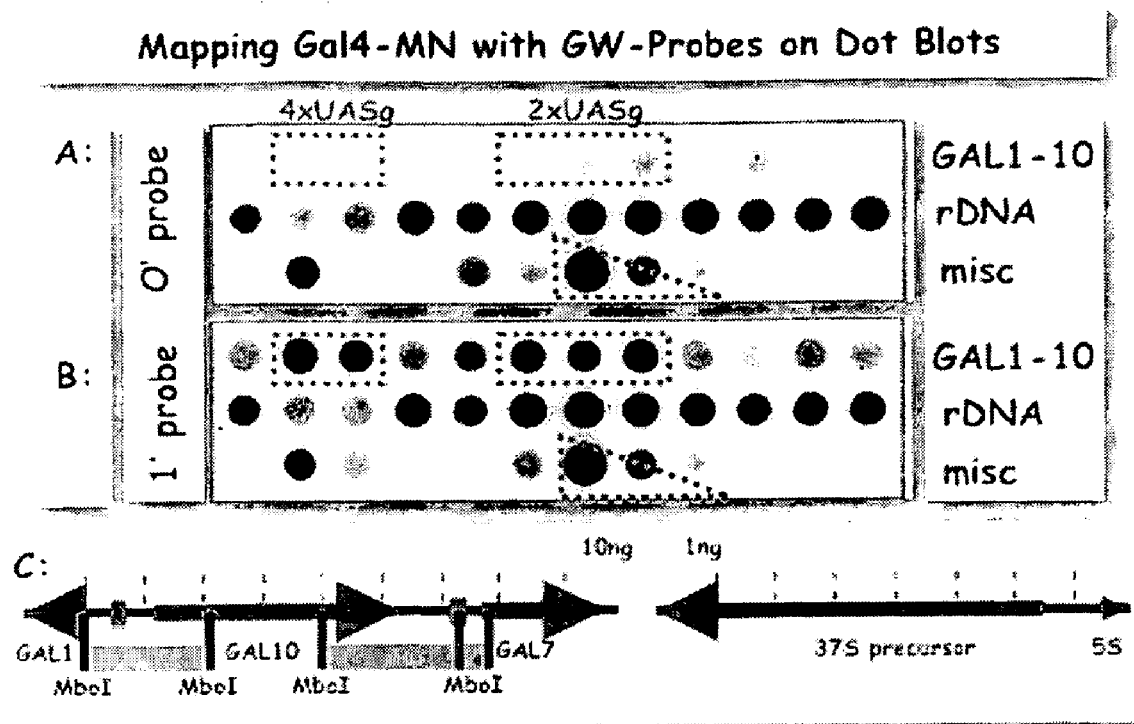

FIG. 9 depicts the mapping of Gal4-MN with gw-probes at the GAL locus. Two filters containing spotted DNA were hybridized with gw-probes (FIG. 8) obtained from a Gal4-MN in vivo ChEC experiment carried out essentially as described (see FIG. 6).

The control filter A was hybridized with the zero-minute (0') gw-probe, where cleavage by Gal4-MN was omitted ($Ca^{2+}$ was not added). This gw-probe serves as the background control. Filter B was probed with the gw-probe obtained from samples after one-minute Gal4-MN digestion (1'). The top and second rows of each filter contain spotted PCR-fragments spanning the GAL and rDNA locus, respectively. The bottom row of each filter contains loading controls. Panel C: The positions of the probe fragments are marked in the maps by vertical lines.

Figure 10:
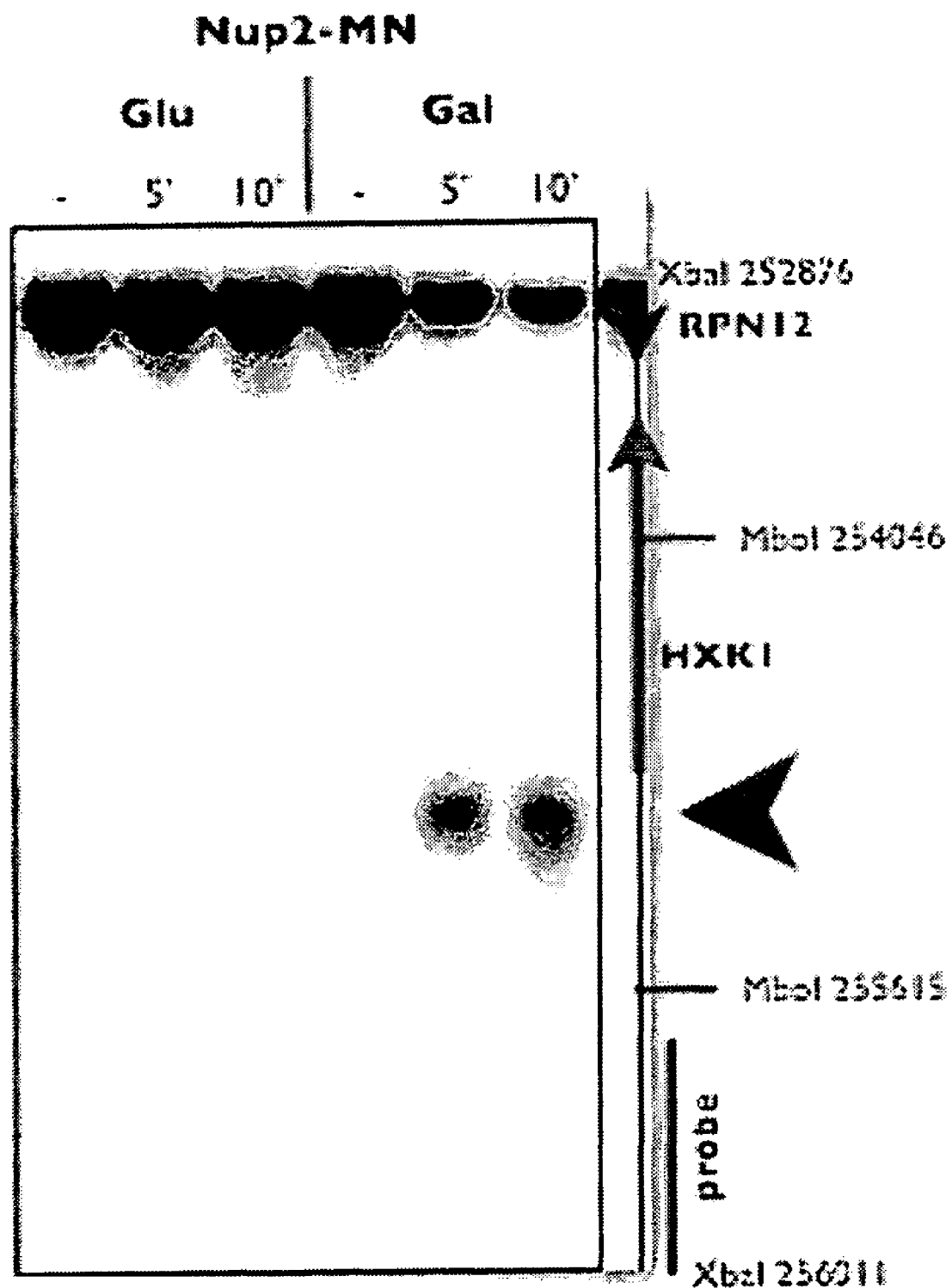

FIG. 10 represents the galactose-dependent cleavage of the HXK1 promoter by Nup2-MN.

Cells expressing Nup2-MN were grown in galactose and glucose and cleavage induced in in vivo ChEC experiments by permeabilizing cells for $Ca^{2+}$ ions. Digestion was for 0, 5 and 10 minutes. DNA was prepared, digested with Xba I, separated by agarose gel electrophoresis and probed by indirect end-labeling with the DNA fragments indicated in the map. It is to be noted that a strongly enhanced cleavage band near the HXK1 promoter is observed in the samples (5' & 10') derived from galactose-grown cells. Similar promoter-specific, activation-dependent cleavage bands were observed at the GAL locus.

FIG. 11 represents the galactose-dependent cleavage of the HXK1 promoter by Nup2-MN.

Panel A: Gw-probes were prepared from glucose and galactose cells expressing Nup2-MN after in vivo ChEC-cleavage for 5 minutes. These probes were hybridized to tiling arrays encompassing the entire yeast chromosome VI. The plot shows log 2 ratios of the hybridization signal (probe-sets) of the galactose versus glucose probe (for details, see Materials and Methods of example 3).

Panel B: The ratio data of panel A are shown at higher-resolution around the HXK1 gene. The signals shown represent the value of probe-sets, where 16 features representing 300 bp are combined.

Panel C: Depicted are the ratio data for each single feature around the HXK1 gene (for details, see Materials and Methods of example 3).

Figure 12:
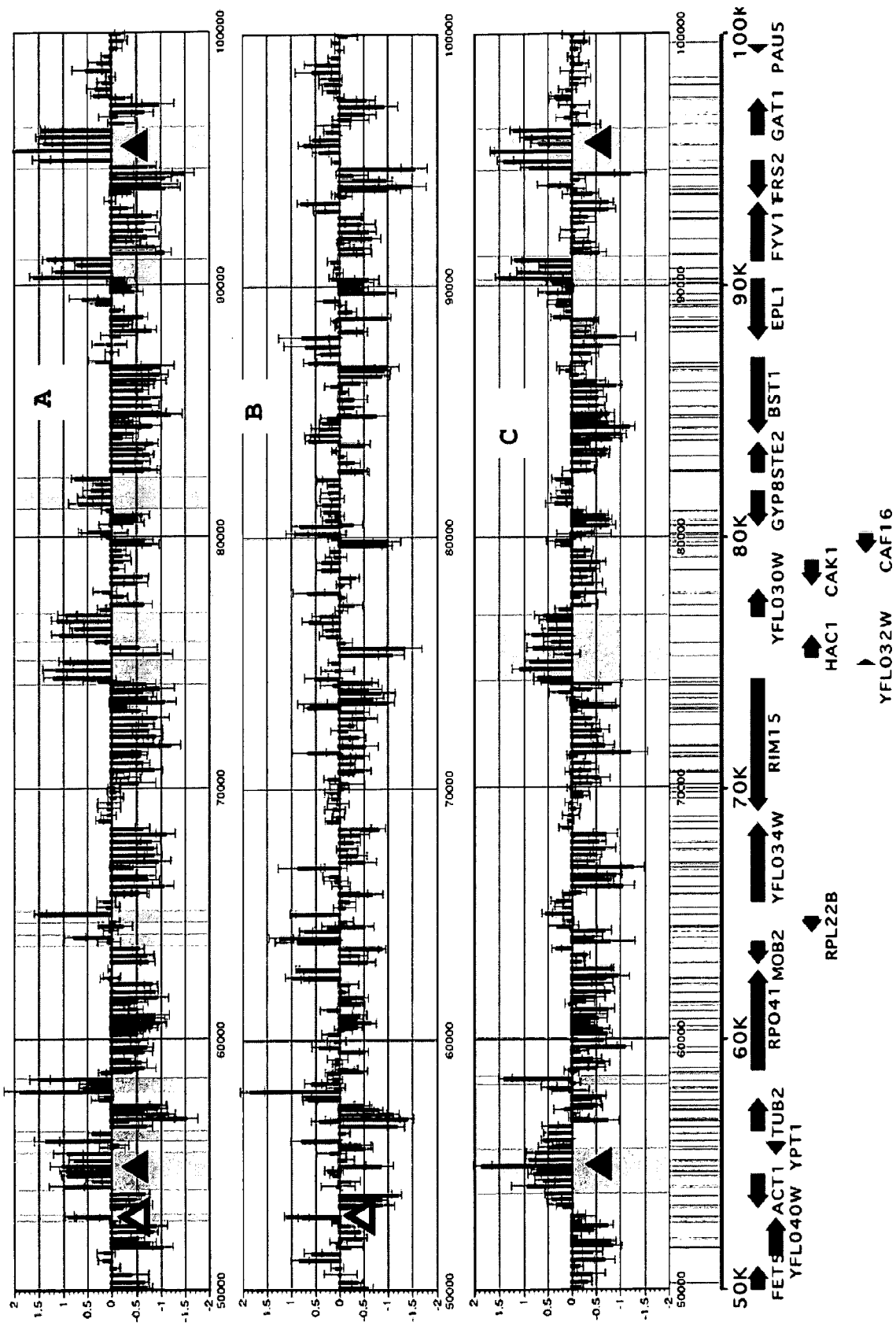

FIG. 12 represents the constitutive Nup2-MN cleavage analyzed chromosome-wide for chromosome VI.

Cells expressing Nup2-MN or H2bMN grown in galactose where processed by the ChEC protocol. Digestion conditions for these cells were 5 minutes at 30° C. and 1 minute on ice, respectively. Gw-probes were prepared and hybridized to tiling arrays of chromosome VI as described in FIG. 10.

Panel A: Uncorrected data of Nup2-MN expressing cells. The ratio of the hybridization signals (log 2) obtained with the 5-min over the zero-min probe were plotted.

Panel B: Uncorrected data for H2b-MN expressing cells. The ratios of the hybridization signals (log 2) obtained with the 1-min over the zero-min probe were plotted.

Panel C: The Nup2-MN data of panel A were corrected for the H2b-MN data of panel B in order to remove the bias introduced at hypersensitive sites.

Figure 13:
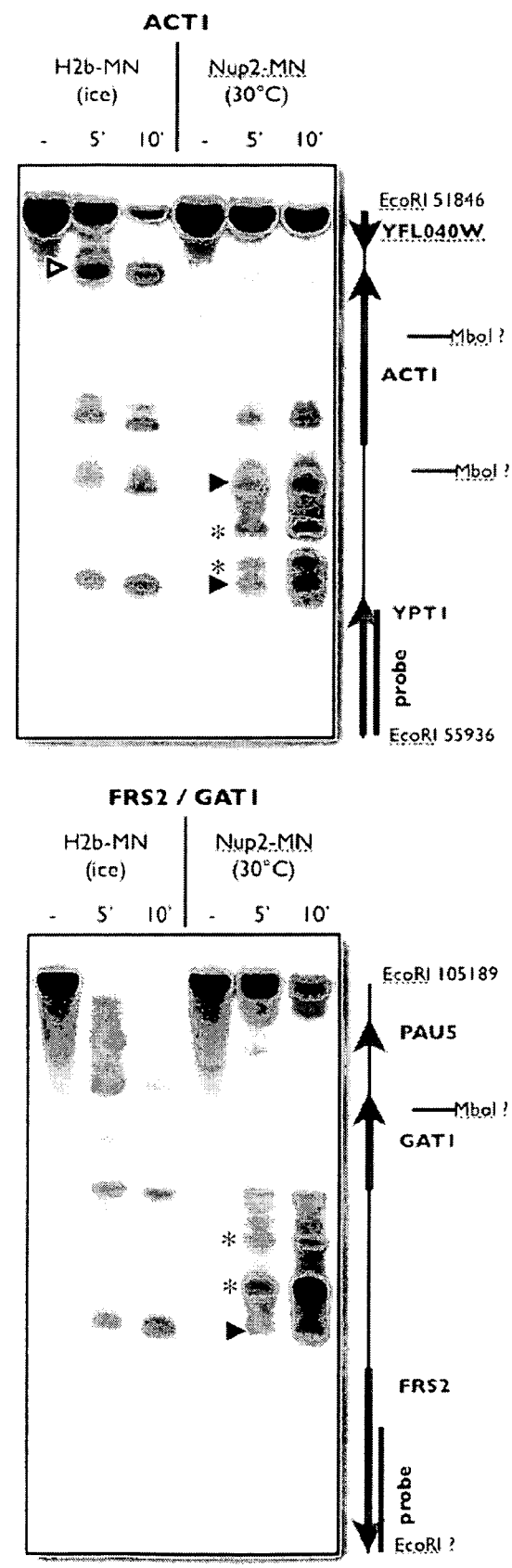

FIG. 13 illustrates the Nup2-MN cleavage at ACT1 and FRS2/GAT1

Cells expressing Nup2-MN and H2b-MN were grown in galactose and cleavage induced in in vivo ChEC experiments by permeabilizing cells for $Ca^{2+}$ ions. Digestion was done for 0, 5 and 10 minutes at 30° C. for Nup2-MN and 0, 1 and 2 minutes on ice for H2b-MN. DNA was prepared, digested with EcoRI, separated by agarose gel electrophoresis and probed by indirect end-labeling with the DNA fragments indicated in the map. Nup2-MN cleavage sites that coincide with H2b-MN sites but are enhanced are marked by closed arrowheads. Cleavage sites specific found only in the Nup2-MN pattern are marked by asterisks.

Panel A: Indirect end-labeling at the ACT1 gene. A strong hypersensitive 3' of ACT1 is indicated by an open arrowhead.

Panel B: Indirect end-labeling at the FRS2/GAT1 gene.

DETAILED DESCRIPTION OF EMBODIMENTS OF THE INVENTION

Throughout this specification and experimental part, reference is made to the publications Schmid M., et al 2004 and Schmid M. et al 2006 (with the supplemental data provided at http://www.molecule.org/cqi/content/full/21/3/379/DC1/). These publications are hereby incorporated by reference.

In the context of the present invention, the following terms are defined in the following manner:

Chromatin is the material of which chromosomes are composed, that is a complex of DNA coated with proteins, mainly histones, and RNA. The fundamental structural unit of chromatin is an assemblage, called the nucleosome, composed of five types of histones (designated H1, H2A, H2B, H3, and H4) and DNA.

A chromatin protein, or a chromatin or DNA binding protein is a protein which often binds specific sites in the genome of a cell. Such a protein may bind either DNA or a proteinaceous component of chromatin. Chromatin or DNA binding proteins are generally involved in regulating genome expression, chromosomal replication or cellular proliferation function. Examples of chromatin proteins are transcriptional activators and repressors. Other DNA-binding proteins are associated with centromeres or with telomeres where their role comprises regulation of chromosome replication and maintenance. Chromatin proteins are often active as complex of several components. Any protein participating in such a chromatin-binding complex will also be considered as a chromatin binding protein in the context of the present application.

A nuclease is an enzyme catalysing the hydrolysis of the nucleic acids into nucleotides or polynucleotides. In the context of the present invention, the term "nuclease" more specifically designs a deoxyribonuclease.

Tether of two entities may be carried out by chemical bound (for example via a peptidic bound) or via interactions like antibody-antigen interactions.

Hypersensitive sites (HS) are short segments of chromatin, where the DNA is more accessible to proteins, for instance nucleases. These segments are sensitive to chemical and enzymatic attack because they are less well protected by proteins. These segments are called hypersensitive sites to indicate their extreme sensitivity to enzymatic digestion.

The present invention relates to a method for localising, in chromatin or DNA, the binding loci of a chromatin or DNA binding protein comprising the steps of tethering, directly or indirectly, an enzyme with a regulatable activity, to said chromatin protein, of transiently activating the enzyme bound to the targeted chromatin and of mapping of the genomic sites in the chromatin which have been enzymatically modified by the regulatable enzyme.

During the tethering step, the regulatable enzyme is preferably kept inactive. The enzyme may be any type of enzyme capable of introducing, into DNA or into protein, an enzymatic modification which can be detected. This enzymatic activity may be phosphorylation, acetylation, methylation, lysis, etc. . . . A preferred enzyme in the context of the present application is a nuclease, specifically an endo-deoxyribonuclease. The regulatable enzyme used in the context of the application is preferably deprived of any chromatin binding domain before the tethering step. Therefore, in the absence of the tether mentioned above, the regulatable enzyme is not directed to specific sites into the chromatin. By regulatable enzymatic activity, it is meant that the enzyme can be switched from an inactive state to an active state upon control. This switch can be controlled by the addition of an effector or by changing the conditions like temperature of the solution containing the enzyme (thermo-sensitivity). Particularly preferred effectors are small chemicals, especially ions like $Ca^{2+}$, whose concentrations can be suddenly raised and also very rapidly decreased. It is thus possible to induce a temporal activation during times as short as a few seconds. Moreover, regulation of the enzymatic activity by means of an effector also allows tight control on the localization of the enzymatic activity.

According to a preferred embodiment of the present invention, the enzyme used in the above-mentioned method is a nuclease, said nuclease having a regulatable activity.

Most of the further aspects and embodiments of the invention will thus be described with a regulatable nuclease as the regulatable enzyme. It is however to be noted that most of these aspects or embodiments are equally applicable to any other regulatable enzymes as defined above. The invention is by no way limited to the choice of a nuclease as the enzyme.

The nuclease which can be used is any protein capable of inducing cleavage sites into DNA, either single or preferably double-stranded cleavage sites, provided this activity is regulatable. The nucleases used in the methods of the invention, are preferably capable of breaking the DNA in a largely sequence-independent manner, generally at nucleosomal linker regions and at nuclease hypersensitive sites. Many nucleases however cleave the DNA in a sequence-specific manner, i.e. cleavage occurs mainly at recognition sequences of a few nucleotides. According to the invention, the nucleases which are used are preferably devoid of such specificity. They can be obtained for example by separating the nuclease domain and the sequence-specific DNA binding domain of known nucleases.

Suitable nucleases for the invention are relatively small, in order not to perturb the cellular and nuclear processes, they have a robust activity and they are well tolerated by cells in general. The same criteria are to be applied in the choice of any other regulatable enzymatic activity according to the general embodiment of the invention. The regulatable nucleases (or other enzymatic activity) of the invention are maintained in an inactive stage during the tethering step. By inactive state, it is meant that the activity of the nuclease is too low to be monitored, or is less than 10% of its maximal rate when active, preferably, less than 4% or less than 1%. The transition from an inactive state to an active state is regulatable or controllable; it may be triggered by the addition of a chemical compound or by switching the temperature for example.

The inactive state of the nuclease may be due to a change in the conformation of the protein which renders it inactive. By switching the conditions such as temperature, pH or ion concentration, it is possible to abolish this conformational change in order to render the nuclease active. The oxidative/reductive conditions may also be responsible for a conformational inactive state. By switching from conditions preventing the disulfide bounds to permissive conditions, the nuclease protein may be rendered active.

Alternatively, the inactive state may be due to the absence of a cofactor, for example an ion, necessary to the function of the nuclease, or due to the presence of an inhibitor. By providing this cofactor or removing this inhibitor, it is thus possible to activate the nuclease.

A particularly preferred nuclease according to the invention is the micrococcal nuclease (MN), whose robust enzymatic activity stringently depends on $Ca^{2+}$ ions of millimolar concentrations. This enzyme introduces DNA double stranded breaks in chromatin at nucleosomal linker regions and at nuclease hypersensitive (HS) sites (Telford and Stewart, 1989). The MN sequence used in the invention preferably comprises the sequence encoding the mature chain of Nuclease A (amino acids 83 to 231 of Genbank P00644, SEQ ID No. 1).

```
SEQ ID N°1:
ATSTKKLHKEPATLIKAIDGDTVKLMYKGQPMTFRLLLVDTPETKHPKKG

VEKYGPEASAFTKKMVENAKKIEVEFDKGQRTDKYGRGLAYIYADGKMVN

EALVRQGLAKVAYVYKPNNTHEQHLRKSEAQAKKEKLNIWSEDNADSGQ
```

It is clear for the skilled person in the art that variants from such sequence may also be active as nuclease. The invention thus also encompass any protein comprising a sequence derived from sequence SEQ ID No. 1 and having at least 70% of identity with sequence SEQ ID No. 1, preferably at least 80, 90 or 95% of identity.

The percentage of sequence identity is the relationship between two sequences which can be measured by counting the number of identical residues and calculating them as a percentage of the total number of residues in the shortest sequence.

When the nuclease is the micrococcal nuclease, the inactive state is obtained by keeping the nuclease in a milieu poor in Ca²⁺ (below millimolar concentrations). A raise in Ca²⁺ concentration leads to an activation of the nuclease. This enzyme has thus a regulatable enzymatic activity according to the invention.

An enzyme according to the invention is thus preferably rendered active by influx of a given ion, for example Ca²⁺.

The enzyme, e.g. nuclease, of the invention is tethered to a chromatin protein binding the chromatin at defined sites, which are preferably sequence-specific sites. By tethering the enzyme to this chromatin protein of interest, the previously non-specific enzyme (e.g. nuclease) is recruited to a specific sequence defined by the tethered chromatin protein.

In a preferred embodiment of the present invention, the nuclease (or other enzymatic activity) is tagged. The tag used may be any type of tag, for example a His-Tag in order to ease the purification of the protein, or an epitope like the myc epitope, or avidin, streptavidin or biotin.

According to preferred embodiments, the nuclease is part of a fusion protein X-nuclease or nuclease-X, wherein X is a peptidic domain. X may be an epitope or an antibody, X may also be an affinity domain for e.g. biotin. In the context of the application, by antibody, it is meant either a complete antibody or part of an antibody sufficient to direct an interaction. Such part is preferably the variable region Fab of an antibody.

The nuclease may also be fused to all or part of the staphylococcal protein A (pA) or to all or part of staphylococcal protein G (pG). These proteins have indeed different affinities for rabbit and mouse IgG. The nuclease may also be fused to any other protein or protein moiety, for example derivatives of pA or pG, which has an affinity for antibodies. A preferred embodiment of the invention is the fusion protein pA-MN, detailed in the examples. In this case, the pA moiety contains 2 IgG binding domains of staphylococcal protein A, i.e. amino acids 186 to 327 of Genbank AAA26676 (SEQ ID No. 2).

```
SEQ ID N°2:
SLKDDPSQSANLLSEAKKLNESQAPKADNKFNKEQQNAFYEILHLPNLNE

EQRNGFIQSLKDDPSQSANLLAEAKKLNDAQAPKADNKFNKEQQNAFYEI

LHLPNLTEEQRNGFIQSLKDDPSVSKEILAEAKKLNDAQAPK
```

It is clear for the skilled person in the art that variants from such sequence may also have affinity for antibodies. The invention thus also encompasses any protein domain comprising a sequence derived from sequence SEQ ID No. 2 and having at least 70% of identity with sequence SEQ ID No. 2, preferably at least 80, 90 or 95% of identity.

The invention is however not limited to this specific fusion protein.

Alternatively, the enzyme, e.g. nuclease, may be linked chemically to the X domain by a bound other than a peptidic bound.

According to the method of the invention, the enzyme is regulatable, it can thus be inactivated, i.e. return to an inactive state, after a given time of activation. The activation period according to the invention is indeed transient. This return to an inactive state may be carried out by reproducing the initial conditions responsible for the inactive stage of the enzyme. This is achieved for example by switching the temperature or the pH value to the initial temperature or pH, or sequestering the cofactor necessary to the activity of the enzyme, introducing the inhibitor, or by destroying the regulatable enzyme.

When the enzyme is the micrococcal nuclease, this inactivation step is carried out by addition of Ca²⁺ chelating agents, for example EDTA (ethylenediamine tetraacetic acid) or EGTA (ethylene glycol bis-(B-aminoethylether) N,N,N-,N-tetraacetic acid).

The temporal activation of the nuclease can be easily controlled. By this way, one may vary the time of nuclease action, for determining the binding sites with greater affinity and those which are less specific for the chromatin protein of interest.

The time of activation of the nuclease may be as long as several hours, but it is preferably less than an hour to shorten processing time and improve the specificity. Preferred activation times are less than 10 minutes, less than five minutes. Preferably, the activation time is around one or two minutes. Under certain circumstances, it may be advantageous to have time of activation as short as 30 seconds or less.

The time of activation is greatly dependent on the temperature at which the reaction takes place. When the enzymatic reaction is to be carried out on ice, at zero degree, the time of activation must be adapted accordingly, that is lengthened with respect to the same enzymatic reaction carried out at room temperature or at 30° C.

Alternatively, when the reaction times are to be shortened, it is recommended to raise the temperature of the enzymatic reaction.

According to an embodiment of the method, tethering of the regulatable enzyme, e.g. regulatable nuclease, to the chromatin protein of interest is done indirectly. By indirectly, it is meant that there is no chemical bound between the enzyme and the chromatin protein of interest. The tether may be of the type of antigen-antibody interaction. This may be obtained for example by fusing the enzyme to a domain X having affinity for rabbit (alternatively mouse, or other) antibodies. The chromatin protein of interest will interact with a primary rabbit (alternatively mouse, or other) antibody specific for this chromatin protein, which will in turn interact with the enzyme via the X domain.

Alternatively, a second antibody may be introduced, which binds specifically the primary antibody and interacts with the enzyme via the X domain. Other interactions may be envisaged, using antibody-antigen interactions or other known interactions with sufficient affinity and specificity. The X domain, to which the enzyme may be linked or fused, is chosen with a view to allowing this cascade of interactions thus tethering indirectly the enzyme to the chromatin protein of interest.

Suitable X domains have already been exemplified, they comprise the domain having SEQ ID No. 2 and related sequences with affinity for antibodies.

The indirect tethering of the enzyme, e.g. nuclease, with the chromatin protein under study is preferably carried out via one antibody; alternatively, two antibodies may be used. It can however be envisaged that 3 or more antibodies are used for tethering the regulatable enzyme to the chromatin protein.

The antibodies used according to the method of the invention for tethering the regulatable enzyme to the chromatin binding protein are preferably polyclonal antibodies, in order to better interact with their target even if some of the epitopes of their target have lost their initial conformation. Monoclonal antibodies may also successfully be used in this method.

The antibodies may advantageously be tagged, for example fluorescently tagged, which allows their detection and their localization. The antibodies may also be tagged by biotin. Biotinylated antibodies are indeed of great interest, especially in the case wherein the regulatable enzyme is linked to an X domain having affinity for biotin, e.g. avidin or streptavidin. The indirect tethering is thus obtained by interaction of the X domain linked to the regulatable enzyme with the biotin born by the primary antibody specific for the chromatin protein of interest or born by a second or further antibody, specific for the primary antibody.

As mentioned above, for inducing an indirect tether between the chromatin protein of interest and the regulatable enzyme (for example a regulatable nuclease), it is important to have a primary antibody specific for said chromatin protein of interest. However, the method of the invention may be carried out even without possessing such a specific antibody. Indeed, according to one embodiment, the chromatin protein is linked, preferably as a fusion protein, to one or several given epitopes for which specific antibodies are available. Such an epitope may be for example the myc epitope, as illustrated in the example 1 of the present invention.

By chromatin protein, it is meant either the chromatin protein of interest or the fusion protein as described above, encompassing said chromatin protein of interest. This latter fusion protein also possesses the capacity to bind the chromatin, at the same loci as the non-fused protein of interest.

Thanks to the use of a chromatin protein comprising a fusion of the protein of interest with one or several epitopes, it is possible to use the same antibody, irrespective of the chromatin protein of interest under study. By this way, the method of the invention may easily be repeated for testing different chromatin proteins of interest without undue experimentation.

According to the embodiment illustrated in example 1, the chromatin protein of interest is fused to 13 myc epitopes. The primary antibody used for the indirect tethering is thus a mouse antibody directed to these myc epitopes. The second antibody is a rabbit anti-mouse antibody (RAM). This second antibody interacts with pA (staphylococcal protein A) fused to the nuclease. Alternatively, the nuclease may be fused to pG which is capable of interacting directly with a high affinity with antibodies from a different species, rendering unnecessary the step with the second antibody.

Another advantageous possibility is to used a regulatable enzyme covalently linked to an antibody, preferably linked to an antibody specific for the chromatin protein of interest (or for a tag bound to said chromatin protein). This covalent link may be a fusion protein comprising the enzyme and the antibody. According to the invention, a fusion between a regulatable nuclease (e.g. micrococcal nuclease) and an antibody directed to a chromatin protein is particularly preferred. It is thus possible to achieve an indirect tether without need to introduce additional antibodies, if the antibody part is provided linked to the regulatable enzyme.

Use of antigen/antibody interactions implies that blocking and washing steps are preferably introduced into the method of the invention, in order to maintain the specificity of the tethering between the regulatable nuclease (or another chosen enzyme) and the chromatin protein of interest.

In another embodiment of the present invention, the tether between the regulatable nuclease (or another chosen enzyme) and the chromatin binding protein of interest is a direct link. One application of this embodiment is the expression of a fusion protein comprising both the regulatable nuclease (or other chosen enzyme) and the chromatin protein. Preferably, when both proteins are expressed as a fusion protein, a linker is inserted between both coding sequences, in order to ensure the right conformation of both moieties. In the fusion protein, the nuclease moiety is preferably positioned in C-terminal with respect to the chromatin binding protein of interest. Alternatively, fusion protein comprising the nuclease moiety in N-terminal with respect to the chromatin protein may also be used. According to another possibility, it is also envisaged that the nuclease is fused internally in the fusion protein, i.e. linked at both sites by other peptides.

With regard to the linker between both moieties, its length is preferably comprised between 0 and 10 amino acids, even if longer linker may be necessary in specific conditions. The sequence and length of the linker are generally not a key feature of the fusion protein. Sequence and length are however preferably chosen to optimize the precision of localized enzymatic cleavage of the DNA. In this respect, linker is thus preferably as short as possible, however allowing accessibility to the DNA for the tethered nuclease. The linker is preferably unable to interact with the chromatin, and also preferably unable to interact with any of the domains of the fusion protein. When the chromatin protein under study is part of a complex of several proteins, it may be advisable to lengthen the linker.

The fusion protein comprising the regulatable enzyme and the chromatin protein of interest may be expressed from a plasmid bearing the coding sequence for said fusion protein. The plasmid is then introduced into the cell comprising the targeted chromatin. According to this embodiment, the fusion protein is expressed from the plasmid, under a promoter carried by the plasmid. The chosen promoter may be for example an inducible promoter, for controlling the induction of the fusion protein. The promoter may also induce over-expression of the fusion protein. According to the invention, the promoter used to express the fusion protein from the plasmid does preferably not lead to over-expression of the fusion protein.

Alternatively, it is also envisaged to introduce by homologous recombination, at the locus of the chromatin binding protein of interest in the genome of the cell, the DNA sequence coding for the regulatable nuclease moiety (or another chosen enzyme) and optionally for the linker, in fusion with the gene encoding the chromatin protein of interest. By this way, the fusion protein is expressed from the endogenous locus, under the control of the endogenous regulatory elements, thus at physiological level.

The DNA encoding the fusion protein may also be inserted into the genome of the cell at non-homologous sites, by stable transformation.

An advantage of the present method of the invention is that it may be carried out according to an in vitro or an in vivo protocol, resulting however in very similar results, as shown in the examples. The invention may also advantageously be carried out in a cell-free system, with purified chromatin and purified proteins and protein complexes.

The in vivo and in vitro embodiments concern steps a) and b) of the method as defined previously.

There are several ways of carrying out the invention according to the in vitro embodiment. Illustrative particular in vitro protocols are presented hereinafter, one protocol is named ChIC for chromatin immunocleavage; it can be carried out in solution or in a solid state; the second one is named in vitro ChEC, for chromatin endogenous cleavage. For these protocols, the regulatable enzyme is a regulatable nuclease.

The ChIC method consists in tethering indirectly the nuclease and the chromatin protein of interest, via antibodies. This procedure is preferentially to be applied to crude nuclei, especially formaldehyde-fixed nuclei. These nuclei are obtainable inter alia by breaking cells mechanically (e.g. with glass beads) or by spheroplasting. In the presence of detergent, the cells thus opened allow accessibility of chromatin to antibodies. Other methods suitable for obtaining crude nuclei of cells while maintaining the chromatin structure are well known in the domain. The methods limiting the proteolytic damage are preferred. The in vitro embodiment of the method may be applied to chromatin extracted from the cells by any means maintaining the chromatin structure, providing proteolytic damage has been limited.

The different ways for indirectly tethering the nuclease to the chromatin protein via antigen/antibody interaction have been detailed above. In this protocol, it is supposed that the nuclease is expressed as a fusion protein with another peptidic domain, called X domain.

Steps a) and b) of the ChIC procedure of the invention in solution may be carried out according to the following steps:

Step 1: Binding of the primary antibody to crude nuclei that were previously blocked with BSA (Bovine serum albumin) or other well known blocking solutions. Following incubation, excess antibodies are removed by a number of washing-centrifugation steps. The primary antibody is specific for the chromatin protein of interest or for any tag linked to the chromatin protein.

Step 2: A second antibody is then optionally added. This second antibody layer ensures more quantitative retention of the nuclease fused to the X domain, when the X domain has higher affinity with the second antibody than with the primary antibody used in Step 1. This step can be omitted if the primary antibody has a high affinity for the X moiety. Following incubation, excess antibodies are removed by a number of washing-centrifugation steps.

Step 3: Addition of the fusion protein comprising the nuclease to crude nuclei that are very stringently washed following incubation. All above steps are carried out in a buffer and at conditions ensuring that the nuclease is maintained inactive.

Step 4: Change in the buffer and/or in the conditions, thus allowing the nuclease to switch form an inactive to an active state.

The invention is not limited to this specific protocol. Variants can be envisaged.

It is immediately apparent that the above-described ChIC may easily be adapted to the choice of other regulatable enzymes.

The ChIC method may also be carried out by "solid-state", in order to shorten the processing times, to improve the specificity and to allow additional improvements. According to this specific procedure, chromosomes, nuclei or permabilized cells are attached to a solid support, for example glass coverslips.

It is important to attach the material sufficiently firmly in order to prevent loss of material during the washing steps. In view of step c), i.e. mapping the breaks introduced in chromatin, it is however also necessary to attach the DNA to the support in a reversible manner. This may be done by choosing an appropriate support or an appropriate coating on the support, said coating being a tethered material allowing direct or indirect tethering. This coating may allow reversible retention of the chromatin. In this case, the inventors have found that a suitable coating is for example the commercially available "polyphenolic proteins" (BD Cell-Tak™).

Alternatively, the chromatin may be covalently bound to the solid support. Different chemicals are known for their capacity to covalently bind chromatin. This covalent bound is preferably sensitive to lysis, for example hydrolysis, in order to be able to remove the bound chromatin for the mapping step. Formaldehyde fixation of chromatin to the solid support is also envisaged in the context of the present invention.

The advantages of the solid-state ChIC protocol are ease of handling, rapidity of procedure and high specificity. It also offers the opportunity to carry out optical quality controls. Importantly, the solid-state ChIC can be carried out with all biological material that is immuno-stainable; this includes tissue sections obtained from biopsies.

This protocol can also easily be modified for being adapted to another regulatable enzyme.

As mentioned above, another example of in vitro procedure for the method of the invention is the in vitro ChEC. According to this particular procedure, the chromatin binding protein of interest and the nuclease are both parts of a fusion protein. Preferred nucleases for this application have a relatively low molecular weight in order to be fused to the chromatin protein of interest without serious physiological consequences.

In order to implement the ChEC procedure, the chosen nuclease must also be in an inactive state under the conditions present in the cytoplasm and nucleus of the cells. The activation of the nuclease is then triggered by change of these natural conditions. Such a nuclease is for example the micrococcal nuclease. Indeed, the $Ca^{2+}$ level in the cytoplasm and nucleus of the cells is too low (around 50 to 200 nM) to activate the nuclease (which requires a $Ca^{2+}$ concentration in the millimolar range, optimally 10 mM, for being active as nuclease).

According to the in vitro ChEC method, the cells under investigation, which express the fusion protein (nuclease fused to the chromatin protein of interest), are fixed (preferentially with formaldehyde) and lysed (for example with glass beads or spheroplasting), prior to changing the conditions thus triggering the activation of the regulatable nuclease. It is demonstrated in the experimental part of the application that the nuclease moiety of the fusion protein retains sufficient nucleolytic activity despite fixation. When the in vitro ChEC method is implemented with the micrococcal nuclease, the change in the conditions is addition of $Ca^{2+}$.

The specific procedures for carrying out in vitro the methods of the invention are not limitative, any other derived or different procedure may of course be envisaged by one skilled in the art, especially depending on the chosen regulatable enzyme or nuclease and its mode of activation.

It must also be noted that, in addition to these procedures, the present invention also provides protocols for carrying out in vivo the method of the invention. In vivo and in vitro aspects are relative to the steps (a) (tetheing) and (b) (activating) of the mentioned method detailed above. The mapping step of the method is carried out in vitro, independently of the previous steps.

One procedure suitable for carrying out in vivo the method of the invention is the in vivo ChEC. According to this procedure, the nuclease is expressed in the cells under investigation as a fusion of the chromatin protein of interest. Most of the requirements mentioned for the preceding protocols, specifically in vitro ChEC, are identical for this procedure. However according to the vivo ChEC procedure, in step b) of the method of the invention, the cells are not fixed and lysed. On the contrary, cells under investigation are native cells and change of the conditions in order to trigger activation of the nuclease is carried out on the whole cells.

When the nuclease used in this procedure is the micrococcal nuclease, influx of calcium ion into the cell may be triggered by activation of a ionophore, a $Ca^{2+}$ transporter. It may also be triggered by permeabilization of the living cells, for example with digitonin. The method of the invention can be carried out in a cell-free system, or in a cell.

The chromatin binding protein of interest is a protein from a prokaryotic cell or preferably from a eukaryotic cell, lower eukaryotes like yeast, or higher eukaryotes like fly cells, mammalian cells or human cells. The method of the invention is however not limited to any type of cell or chromatin binding protein.

Step c) of the method of the invention is directed to the mapping of the enzymatically modified sites introduced by the enzyme into the chromatin. When the regulatable enzyme is a regulatable nuclease, step c) is directed to the mapping of the cleavage sites introduced into the chromatin by the nuclease tethered to the chromatin protein of interest.

According to the invention, in case of a regulatable nuclease, the mapping of the cleavage sites can be carried out with a very good resolution, thus defining the binding loci of the protein of interest with high confidence. The resolution obtained by the method of the invention is far better than the resolution obtained by the methods disclosed in the prior art. Indeed, according to the invention, the cleavage sites may be mapped with a resolution less than 300 bases, even less than 100 bases. Under appropriate conditions, a resolution even better can be obtained, allowing localization of the cleavage sites with a resolution of a few dozen of nucleotides or even less. Examples of results showing such a resolution are given in the experimental part of the present application. Localization of the cleavage sites is informative of the localization of the binding loci of the chromatin protein of interest. Indeed, the inventors have shown in the example 1, that cleavage sites and binding loci are co-localised within a few tenths of nucleotides. Therefore, the binding loci of the chromatin protein of interest are deduced from the mapping of the cleavage sites (or other enzymatic modifications). Cleavage sites of the regulatable nuclease may be mapped by Southern blotting with the indirect end labeling method, in which a DNA fragment abutting a restriction enzyme cleavage site is used as hybridization probe. This procedure maps DNA cleavage cuts relative to this restriction site. This procedure for mapping the cleavage sites is illustrated in the example 1 and in FIG. 2A.

The restriction enzyme used in this procedure generally cleaves the targeted DNA under study every 2 to 12 kb. However, when a higher resolution is wished, a restriction enzyme may be chosen that cleaves closer to the expected binding locus of the chromatin protein of interest.

The cleavage sites of the regulatable nuclease may also be mapped by PCR technologies like LM-PCR (Ligation-mediated Polymerase Chain reaction), real-time PCR or by primer extension.

According to the primer extension technique, a primer complementary to a sequence next to the sequence of interest (distance generally inferior to 500 bp) is annealed. A primer-dependent DNA polymerase (ie Taq polymerase, E. coli DNA Polymerase, Sequenase, Vent polymerase) is then used to extend this primer. The polymerase will stall at the position of nicks in the template strand. The product length is informative about the position of nick compared to the hybridization site of the primer.

The LM-PCR technique maps single and double-stranded breaks. This technique can be used in combination with primer extension to map single-strand breaks using an amplification step (ie less starting material required, more stringent, . . . ). After primer extension, an Adaptor (linker) is added to the double stranded end created by the stalled polymerase and amplification by PCR is carried out, using a first primer, complementary to a sequence next to the sequence of interest, and a second primer specific for the Adaptor. The product length gives the position of the nick compared to primer site. LM-PCR can be used to map double-stranded breaks (ds-breaks) by directly starting with ligation of an adaptor (or linker) to the ds-breaks. PCR with combination of a specific primer (as in primer extension) and a primer for Adaptor is then carried out. The product length gives the position of ds-breaks with respect to the hybridization site of the primer.

Products are normally separated on sequencing gels, which, under appropriate condition, gives a single base pair resolution.

These LM-PCR and primer extension procedures are perfectly suited for detecting the loci of cleavage sites with a very high resolution, below 5 nucleotides if the migration gel is sufficiently resolutive.

The inventors have also found that the specificity of the cleavage pattern for a given chromatin protein tethered to a nuclease according to the invention, may be improved by deducing from this pattern the loci which are not specific for the chromatin protein of interest. Indeed, in the chromatin, the attachment of regulatory proteins to the DNA can also create short segments of chromatin relatively free of nucleosomes. These sites are very sensitive to chemical and enzymatic attacks. These sites, called hypersensitive sites, are thus very likely to be cleaved by the tethered nuclease, even if the chromatin protein of interest does not bind tightly at these sites. Moreover, due to their sensitivity, these sites may also be cleaved by any other nuclease present in the cell during the different steps of the method of the invention. Therefore, the mapping of the cleavage sites introduced into the chromatin also reveals the hypersensitive sites of the chromatin, although they are not necessarily specific for the chromatin protein of interest.

In one embodiment of the method of the invention, it is thus recommended to deduce the non-specific general binding sites along the chromatin form the binding loci already mapped. In order to carry out this step, it is thus important to determine the hypersensitive sites in the chromatin under study. This may be done by carrying out the method in the invention, however with free nuclease, i.e. without tethering the nuclease to any specific chromatin binding protein. This free protein will introduce cleavage in the DNA at the sites which are highly accessible and not protected, that are the hypersensitive sites of the chromatin.

The inventors have also compared the pattern obtained with free nuclease and with the same nuclease bound to a histone protein (see Example 1). They were able to conclude that the pattern is very similar. In order to determine the hypersensitive sites of the chromatin, one can thus carry out simultaneously the method of the invention with the nuclease tethered to the chromatin protein of interest on one side and with the nuclease tethered to a histone protein on the other side. The signals obtained with the first experiment are to be balanced by those obtained for the second experiment.

The correction procedure is also applicable to other regulatable enzymes according to the invention, it is not limited to the nuclease embodiment.

According to a first aspect of the method of the invention, the localisation of the binding locus of interest is determined by the extent of digestion (when the regulatable enzyme is a nuclease) of a given chromatin fragment with a probe specific for that chromatin fragment. The method is thus used in order to precisely define the binding site on a fragment already identified. A very high resolution is preferred for this application of the method of the invention.

Alternatively, the method of the invention may be used on a chromosome-wide scale or a genome-wide scale.

The chromosome- or genome-wide mapping may be carried out with DNA fragments abutting the DNA enzymatically-modified sites introduced by the activated tethered regulatable enzyme. These DNA fragment are then hybridized to the DNA to be screened, encompassing the entire chromosome or genome, or fragments thereof.

When the regulatable enzyme is a nuclease, the chromosome- or genome-wide mapping may be carried out by hybridizing DNA fragments abutting the DNA cleavage sites introduced by the activated tethered nuclease to DNA encompassing the entire chromosome or genome. The DNA fragments abutting the DNA cleavage sites are called gw-probes. These probes are specific for the binding loci of chromatin protein under study. They are obtained by carrying out steps a) and b) of the method of the invention, followed by generation of probes specific for the cleavage sites introduced into the targeted chromatin.

These gw-probes are hybridized with DNA encompassing the entire chromosome or genome, or the region of interest, or specific DNA fragment to be screened. It must be noted that the gw-probes may be used against any library, representing a whole chromosome, a whole genome, or only regions or fragments of interest.

These probes are labeled in order to detect their hybridization to an element of the screened library. They are labeled by any conventional techniques. For example, a fluorescent label is perfectly suitable for the gw-probes. As mentioned above, it may also be important to deduce non-specific binding sites from the binding loci identified by the present invention. In this respect, two sets of gw probes may advantageously be used, one set corresponding to the probes abutting the DNA cleavage sites of the chromatin protein of interest, the other set corresponding to probes abutting non-specific DNA cleavage sites. The results obtained with the first set of probes are to be corrected by balance with the results obtained from the second set. An example of such a correction is given in example 3 and illustrated in FIG. 12.

According to a specific embodiment of the invention, a different label is linked to each of the gw probe, in order to ease the correction step. The labels may be fluorescent labels with different wavelengths, thus allowing simultaneous screening of the library with both probes.

Different methods are available for designing the gw-probes abutting the DNA cleavage sites, one potential method comprises the following steps:
1. preventing DNA breaks, other than those introduced by the tethered nuclease, from subsequent modification,
2. rendering the cleavage sites introduced by the activated tethered nuclease capable of ligation with a linker
3. ligating a linker to said cleavage sites
4. digesting the chromatin with a restriction enzyme or another nuclease, or DNA fragmentation by mechanical shearing (i.e. sonicaion), or chemical fragmentation
5. isolation of the DNA fragments encompassing the linker and optionally amplification of said fragments.

Variants of this method and alternatives are well known to the skilled person in the domain.

When the regulatable enzyme used in the method of the invention is a nuclease, the following precisions may be added for the steps mentioned above (see also example 3 of the present application):

Step 1: the cleavage sites introduced by the nuclease are 5'-OH/3'-P; this step consists in preventing the DNA breaks which have a 3'-OH from subsequent modification, they are thus modified by adding a ddNTP (dideoxynucleotide triphosphate) to the 3'-OH and creating a 3'-H that is not ligateable. These ends are also not a substrate for Terminal Transferase Step 2: a T4 polynucleotide kinase (PNK) may be used to modify the 5'-OH/3'-P ends introduced by the nuclease into 5'-P/3'OH; these ends are ligateable and are also suitable substrates for Terminal Transferase.

Alternative treatment with a phosphatase (ie Calf Intestine Alkaline Phosphatase (CIAP)) would make 5'-OH/3'-OH ends that are substrates for Terminal Transferase.

Step 3: the linker which is used may be biotinylated to allow subsequent isolation of the fragments. Alternative epitopes for isolation are also possible.

Alternative treatment with Terminal Transferase in combination with a single dNTP or single biotinylated dNTP will create a homopolymeric tail that replaces the linker added by ligation.

Step 5: the isolation of the DNA is preferably achieved with the help of biotin bound to the linker used in step 3. Amplification may be carried out by ligating a second linker, linker B, to the digestion end from step 4 and a PCR is then carried out using primers specific for both linkers.

Alternatively, amplification can be carried out by in vivo transcription using in step 3 or step 5 a linker containing an RNA polymerase promoter sequence.

The genome-wide application of the present method is preferably carried out with an array, comprising the library of fragments to be screened. This array is preferably a microarray or dot blots, in order to automate the sample screening. Advantageous microarrays are tiling microarrays. Such microarrays may be commercially available or be designed especially for carrying out the invention.

The array may comprise samples of different types; it may comprise genomic DNA, and/or cDNA, and/or DNA comprising mainly chromatin binding regions, and/or DNA comprising regulatory regions, and/or RNA, and/or RNA comprising mainly chromatin binding regions. Any combination of such samples may also be envisaged.

The method is perfectly suitable to determine whether a given protein binds the chromatin of a cell at a suspected specific locus. It may indeed be useful to confirm for example preliminary results indicating the binding of said protein at a suspected specific locus in chromatin. In this embodiment of the invention, the method comprises the following steps:
tethering a regulatable enzyme, for example a regulatable enzyme, to said chromatin binding protein,
transiently activating the regulatable enzyme in presence of the targeted chromatin and
detecting whether, at the given specific locus, an enzymatic modification has been introduced into the chromatin by the regulatable enzyme.

In the specific case where a regulatable nuclease is used, this last step consists in detecting whether a cleavage site has been introduced into the chromatin at the given specific locus.

The invention may alternatively be applied for screening for proteins which are capable of binding the chromatin of a cell at a given specific locus. There are indeed situations where binding sites for chromatin protein are identified or suspected, however without identification of the corresponding binding protein. A library of candidate proteins may be screened for their capacity to bind said suspected locus in the chromatin. According to this embodiment, the method comprises the following steps:
tethering, preferably indirectly, a regulatable nuclease to a candidate protein,
transiently activating the nuclease in presence of the targeted chromatin and
detecting whether a cleavage site has been introduced into the chromatin at the given specific locus.

It must be noted that this method may also be carried out with any other regulatable enzyme. In this case, the last step consists in detecting whether, at the given specific locus, an enzymatic modification has been introduced into the chromatin by the regulatable enzyme.

The invention also concerns a method for localising, in chromatin or DNA, the binding loci of a chromatin or DNA binding protein comprising the following steps:
  a) Fixing the targeted chromatin
  b) Binding a primary antibody, specific to the chromatin binding protein;
  c) Optionally, binding of a second antibody, specific for the primary antibody;
  d) Adding a nuclease in an inactive state, fused to a domain having an affinity for the primary antibody (or optionally for the second antibody), e.g. pA; pG or an antibody, or an affinity domain for e.g. biotin;
  e) Transiently adding $Ca^{2+}$;
  f) Mapping the cleavage sites introduced by the nuclease into the chromatin;

wherein steps b) to d) are carried out in a buffer containing an agent chelating the $Ca^{2+}$ ion.

Such a method is exemplified in details in example 1.

The invention is also directed to kits for carrying out the method of the invention. The kits of the invention may be specific for a given chromatin protein, known to be implied in numerous cellular pathways by binding to different loci of the genome. Such a chromatin protein is for example a silencer, which can bind the chromatin at numerous loci. Alternatively, kits according to the invention may be of general applicability, irrespective of the chosen chromatin protein under study.

A kit of the second type, for localising the binding loci of a chromatin binding protein of interest in chromatin, generally comprises at least the following components:
  an enzyme having regulatable enzymatic activity;
  an antibody specific for a given tag (for example for the myc tag) or epitope
  instructions for cloning a chromatin binding protein of interest in frame with said tag or epitope (for example myc tag);
  means for activating the enzymatic regulatable activity.

The antibody is advantageously linked to the regulatable enzyme, for example directly fused. Alternatively, the kit may comprise means for carrying out this link.

When the kit is prepared for a specific chromatin protein, it preferably comprises:
  an enzyme having regulatable enzymatic activity;
  an antibody specific for said chromatin protein,
  means for activating the enzymatic regulatable activity.

The antibody is advantageously linked to the regulatable enzyme, for example directly fused. Alternatively, the kit may comprise means for carrying out this link.

The antibody is preferably tagged, for example with an affinity domain. Alternatively, the regulatable enzyme may also be provided as a fusion protein, as exemplified in the application. The kit may also provide the specific chromatin protein, optionally as a fusion protein with a tag, as exemplified above.

A kit of the invention may advantageously comprise means to reduce background for increasing the specificity. As detailed above, such means may comprise all the necessary material for comparing the results obtained with a chromatin protein of interest to the results obtained with a non-specific chromatin protein or with free regulatable enzyme. When a nuclease is used as regulatable enzyme, the example 3 (specificity) provides examples of means to reduce background to increase specificity.

A preferred regulatable enzymatic activity is a $Ca^{2+}$-dependent nucleolytic activity. The micrococcal nuclease is an example of an enzyme having such a $Ca^{2+}$-dependent nucleolytic activity. In this case, the means for activating the regulatable enzymatic activity is for example a ionophore, or digitonin in order to permeabilize the cell.

The kits of the invention may further comprise a solid support for immobilizing the crude nuclei containing the targeted chromatin. Suitable solid supports are coverslips, preferably coated glass coverslips, as detailed previously in the application.

In preferred embodiments, kits of the invention comprises the regulatable enzyme as part of a fusion protein with a domain X, wherein X is a domain having affinity for an antibody (e.g. pA, or pG), or an affinity domain for e.g. biotin. Alternatively, X may be an antibody or part of an antibody, for example directed to a specific chromatin protein; alternatively, the antibody may be directed to a tag to be linked to the chromatin protein under study.

As mentioned above, preferred regulatable enzymes according to the invention are regulatable nucleases, especially Ca2+-dependent nucleases. Examples of such nucleases have already been given. A particularly preferred nuclease is the micrococcal nuclease having the sequence SEQ ID No. 1 or a nuclease having at least 70% sequence identity with said sequence.

Different buffers, solutions, positive and/or negative controls and instructions may be added to the kits of the invention

EXAMPLES

Example 1

Genomic Mapping of Chromatin Proteins

To map the genomic interaction sites of chromatin proteins two related methods were developed and experimentally explored in *Saccharomyces cerevisiae*. The ChIC method (chromatin immuno-cleavage) consists of tethering to specifically bound antibodies a fusion protein (pA-MN) consisting of micrococcal nuclease (MN) and staphylococcal protein A. The nuclease is kept inactive during the tethering process (no $Ca^{2+}$). The ChEC method (chromatin endogenous cleavage) consists of expressing fusion proteins in vivo, where MN is C-terminally fused to the proteins of interest. The specifically tethered nucleases are activated with $Ca^{2+}$ ions to locally introduce double-stranded DNA breaks. It is demonstrated that ChIC and ChEC map proteins with a 100-200 bp resolution and excellent specificity. One version of the method is applicable to formaldehyde fixed nuclei, another to native cells with comparable results. Among various model experiments, these methods were used to address the conformation of yeast telomeres.

The methods introduced here consist of tethering micrococcal nuclease in an inactive state (no $Ca^{2+}$ ions) directly (in vivo) or indirectly (via antibodies) to proteins of interest.

Results

Outline of the ChIC method: The basic idea of the chromatin immuno-cleavage (ChIC) method is to indirectly tether a nuclease, whose activity can be controlled, to antibodies that are specifically bound to a chromatin protein of interest. Subsequent activation of the tethered nuclease results in DNA cleavage in the vicinity of the chromatin bound protein. Mapping of such DNA cleavage sites provide information about the genomic interaction sites of the protein of interest. The micrococcal nuclease (MN) was selected as enzyme of choice since its robust enzymatic activity stringently depends on $Ca^{2+}$ ions of millimolar (optimal 10 mM) concentrations. This enzyme introduces DNA double-strand breaks in chromatin at nucleosomal linker regions and at nuclease hypersensitive sites (HS) (Telford and Stewart, 1989).

To tether MN to antibodies, a fusion protein was prepared consisting of two immunoglobulin binding domains of staphylococcal protein A (Harlow and Lane, 1999) that are N-terminally fused with MN. The protein (called pA-MN) has a molecular weight of 34 kD and was expressed in E. coli. Purified pA-MN was found to have comparable specific activity as the untagged enzyme. In a general sense, the ChIC method is akin to the antibody staining techniques for immunofluorescence studies, where the last step involves the addition of pA-MN. ChIC differs also from the staining techniques in that it is carried out in solution, where excess antibodies and pA-MN are removed by centrifugation in a microfuge. The ChIC method as been explored using *Saccharomyces cerevisiae* as a model system.

Crude nuclei were prepared from fixed yeast cells either by breaking cells mechanically with glass beads or by spheroplasting. Both procedures yield opened cells (called crude nuclei here) that in the presence of detergent become accessible to antibodies. Although crude nuclei were prepared with either procedure, the glass bead method was generally preferred since it results in less proteolytic damage.

In the experiments presented in this example, proteins of interest were tagged with 13 myc epitopes. The main steps of the ChIC method including antibody and pA-MN binding are depicted in FIG. 1A.

Step 1: Binding of the primary antibody (anti-myc monoclonal antiserum 9E10 in these experiments) to crude nuclei that were previously blocked with BSA. Following incubation, excess antibodies were removed by a number of washing-centrifugation steps.

Step 2: A rabbit anti-mouse (RAM) antibody was then added. This second antibody layer ensures more quantitative retention of pA-MN, since protein A binds rabbit IgG with higher affinity than mouse IgG1 used in Step 1 (Harlow and Lane, 1999). This step can be omitted if the primary antibody has a high affinity for the protein A moiety. Following incubation, excess antibodies were removed by a number of washing-centrifugation steps.

Step 3: Addition of pA-MN to crude nuclei that were very stringently washed following incubation. All above steps were carried out with a buffer containing an excess of EDTA and EGTA to maintain the nuclease of pA-MN inactive.

Step 4: DNA cleavage by the bound pA-MN is induced by adding $Ca^{2+}$ ions and terminated at different times by chelation. IgG Sepharose beads are added to the cleavage reaction to sequester traces of unbound pA-MN or complexes thereof that become unbound. Note that these beads are too large to interfere with cleavage by the bound pA-MN enzyme in the crude nuclei.

Specificity Considerations: Successful mapping with ChIC depends on specific binding of antibodies and pA-MN. Hence, it is necessary to use high-quality antibodies, optimized concentrations of the added components (antisera and pA-MN) and to execute the washing steps with high stringency. One way to examine the specificity questions is by immunofluorescence microscopy using during step 2 a fluorescent antibody or during step 3 a fluorescent pA-MN protein. A more general method is to examine biochemically whether the retention of pA-MN in the final crude nuclei (step 4) is specific. Hence, is dependent on the addition of a primary antibody during step 1 and/or the expression of the epitope-tagged protein.

To explore the ChIC technique, the DNA-binding domain of GAL4 (Gbd) was tagged with 13 myc epitopes (Gbd-myc13) and expressed (ADH1 promoter) from a CEN plasmid. In a separate strain, the endogenous SIR3 gene of yeast was tagged with 13 myc epitopes (Sir3-myc13). The ChIC procedure was then carried out in parallel with these myc-expressing cells and an untagged yeast strain. Samples were analyzed by SDS-PAGE and Western blotting to follow the antigens, the added antibodies (heavy chain) and the fusion protein pA-MN. FIG. 1B shows as indicated the antigens (top panels), the bound antibodies and added pA-MN (bottom panels) at step 3 (lane 1, 5 & 9). The fractions thereof that remain bound to crude nuclei at the final step 4 are shown in lanes 3, 7 & 11. Lane 2, 6 & 10 represent the supernatant from the first centrifugation-washing step after incubation with pA-MN at step 3.

Of the total pA-MN (T) added during step 3 (panel B, lanes 1 & 5) about 10-20% is bound (B) in the final fraction (step 4) of crude nuclei derived from myc-tagged cells (panel B, lanes 3 & 7). In contrast, the pA-MN band is barely detectable in the final fraction obtained from untagged cells (lane 11). Similarly, the heavy chain band of the antibodies is only observed in the final fraction of crude nuclei (lanes 3 & 7) in myc-expressing cells. Note that some Gbd-myc13 but not Sir3-myc13 is lost into the first supernatant-wash (S) following step 3 (lanes 2 & 6). This loss is thought to be due to dissociation of loosely bound Gbd-myc13 that is strongly overexpressed from the plasmid (see below). Generally, no significant loss of antigen occurs into the supernatant-wash (S) during the ChIC procedure if endogenous genes, such as SIR3, are tagged and studied (panel B, lane 6).

This biochemical procedure established that retention of pA-MN is specific, since it is only observed with the myc-tagged strains. Importantly, this blotting analysis serves to conveniently assess the specificity of the procedure, that is, to determine the optimal concentrations of antibodies, pA-MN and the required stringency of the washing steps. Mapping of Gbd-myc13 and Sir3-myc13 at two Genomic Loci with ChIC. The Gal4 promoter derivative Gbd-myc13 is expected to bind UASg (Upstream Activating Sequences for the Gal genes) DNA elements. This expectation has been addressed in the GAL1-10 region and the silent mating-type locus HML into which a synthetic reporter containing UASg sites was inserted (Ishii and Laemmli, 2003). Cleavage sites were mapped by Southern blotting and indirect end-labeling, where a DNA fragment abutting a restriction enzyme cleavage site is used as hybridization probe. This procedure maps DNA cleavage cuts relative to this restriction site (see map FIG. 2A).

The HML data demonstrate that no cleavage occurs prior to the addition of the $Ca^{2+}$ ions (FIG. 2A, minus lanes). In contrast, addition of this ion yields prominent cleavage bands at the four UASg sites located between the ADE2 and URA3 gene (see map). Exposure to $Ca^{2+}$ for one minute suffices to obtain a strong pattern and further incubation (2 & 4 minutes) does not significantly enhance these bands nor create new ones. A second important cleavage band maps to the distal UASg element located 5' of the ADE2 gene. This band is less prominent, but note that distal cleavage bands are not quantitatively detected by indirect end-labeling Southern blots (see discussion). A weaker but noticeable band maps to the HML-E silencer element. This element contains a major nuclease hypersensitive site (HS, asterisk) that is revealed by digestion of the crude nuclei with free, unbound pA-MN (FIG. 2A, free pA-MN). Cleavage at the silencer in the Gbd-myc13 ChIC experiment could be due to a cryptic binding site or it may arise from a general interaction of the strongly overexpressed Gbd-myc13 (see below).

Examination of the same DNA at the GAL1-10 region (FIG. 2B) shows major cleavage bands at the four UASg sites between the GAL1 and GAL10 genes. A further band maps to the two UASg of the GAL7 gene promoter. A less pronounced band maps to the 3' end of the GAL10 gene; this is a HS site (asterisk) also noted in the control with free pA-MN. A number of weak bands can be observed throughout the GAL1 gene in the Gbd-myc13 pattern.

FIGS. 2A and 2B also contain the data obtained with the untagged strain (no myc). These patterns lack the prominent cuts at UASg sites and show only feeble background bands at the major HS sites.

These experiments establish that the ChIC method localizes Gbd-myc13 with excellent specificity to the UASg sites.

Sir3p is a component of the Sir complex that spreads along the chromatin of the silenced loci HML and HMR and the telomere proximal regions (Rusche et al., 2003). The ChIC pattern of Sir3-myc13 was analyzed at the HML locus and the GAL1-10 region by indirect end-labeling. FIG. 2 shows that Sir3-myc13 mediates a cleavage ladder throughout the HML locus. In contrast, the cleavage pattern is very feeble at the non-silenced GAL1-10 region. HML association of Sir3-myc13 and ensuing cleavage at HML is also evidenced by the strong reduction (90% at 4 minutes) of the 12.1 kb PvuII band of this locus upon addition of $Ca^{2+}$. In contrast, the intensity of the 6.3 kb PvuII band of the GAL1-10 region remains unchanged during incubation (compare Sir3-myc13, panels A& B).

Note that the cleavage bands at HML vary in intensity. This is proposed to reflect the variable accessibility of chromatin to cutting by the tethered nuclease. By way of example, the ChIC pattern of Sir3-myc13 shows a major cleavage band at the HML-E silencer, which encompasses a HS as observed with free pA-MN (asterisk). In general, the cleavage pattern obtained by Sir3-myc13 is similar to the pattern from free pA-MN indicating that Sir3-myc13 is spread homogenously throughout this silent locus. These experiments established that ChIC conveniently maps spreading-type chromatin proteins.

Chromatin Endogenous Cleavage (ChEC) with Fixed Cells. It is next demonstrated that ectopic and endogenous genes can be tagged with micrococcal nuclease, which allows direct genomic mapping. This method is called ChEC for chromatin endogenous cleavage. It is based on the reasoning that the $Ca^{2+}$ level in the cytoplasm and nucleus of yeast is too low (about 50-200 nM) to activate expressed MN (Natsoulis and Boeke, 1991). The low molecular weight of the MN-tag (17.6 kD) permits C-terminal tagging of many genes without serious physiological consequences. Indeed, none of the fusion constructs reported here displayed obvious growth defects.

Several methods (Table 1) were explored to activate the nuclease moiety of MN fusion proteins with $Ca^{2+}$. One reliable method (called in vitro ChEC) was to lyze paraformaldehyde fixed cells with glass beads or spheroplasting prior to the addition of $Ca^{2+}$. Importantly, it is noted that MN retains sufficient nucleolytic activity despite fixation.

A related method is described below where $Ca^{2+}$ is added to native, permeabilized cells (in vivo ChEC).

TABLE I

Comparison of ChIC and ChEC methods:

| | ChIC | in vitro ChEC | in vivo ChEC |
|---|---|---|---|
| Target Protein | Epitope-tagged, untagged | MN-tagged | MN-tagged |
| Tethering of MN | via antibody and pA-MN | direct fusion | direct fusion |

TABLE I-continued

Comparison of ChIC and ChEC methods:

| | ChIC | in vitro ChEC | in vivo ChEC |
|---|---|---|---|
| Cells Cleavage | fixed with glass-bead lyzed cells | fixed with glass-bead lyzed cells | native in permeabilized cells |

Gbd-MN: To explore the in vitro ChEC procedure, the Gbd domain of GAL4 was fused with MN (Gbd-MN) and this protein was overexpressed from a CEN plasmid as described above. Cleavage by Gbd-MN using in vitro ChEC was experimentally analyzed with two different constructs at the HML locus and at the GAL1-10 region. FIG. 3A shows that Gbd-MN cleaves very selectively at the 4 UASg sites of the HML construct (strain KIY141). In contrast, no cleavage was observed at this position in the related HML construct (strain KIY47) lacking UASg. In both strains, only very weak cleavage (background) is observed at the HML-1 element that harbours a major HS site (asterisk) as revealed by digestion with free MN (panel A). Note that for ChEC experiments, free MN (or H2b-MN, see below) is used as control instead of free pA-MN. The DNA samples from this experiment were also analyzed at the GAL1-10 locus. The blot shown in FIG. 3B establishes that Gbd-MN cleaves all UASg sites of this locus specifically. However, a minor cleavage band noted maps to a HS (asterisk, free MN) near the 3' end of GAL10. This latter band was also observed in the ChIC pattern of this same locus (FIG. 2B).

Note that the comparison of the ChIC and ChEC patterns obtained with Gbd-MN and Gbd-myc13 shows that both procedures yield similar data (compare FIGS. 2 and 3).

Gal4-MN: The unexplained cleavage bands at HS sites discussed before may arise from the unphysiological overexpression of the Gbd-MN and Gbd-myc13 protein. To address this question, GAL4 was C-terminally tagged (Gal4-MN) at its endogenous gene locus in a number of strains. Note that Gal4-MN and Gal4p were found to be similarly active in transcription. Examination of the ChEC pattern at the GAL1-10 region demonstrates that Gal4-MN exclusively cleaves the UASg sites of this locus (FIG. 3C). That is, in contrast to the data obtained with Gbd-myc13 and Gbd-MN, cutting at the 3' HS site of GAL10 is not observed with Gal4-MN. Western blotting demonstrated that the endogenous Gal4-MN gene is expressed at a level at least 100 fold lower than Gbd-myc13 and Gbd-MN that are overexpressed from a plasmid. It can be concluded that the background bands mediated by the latter fusion proteins are a consequence of overexpression. FIG. 3C shows that the in vitro ChEC pattern of Gal4-MN is identical for the three different strains shown (discussed below with FIG. 6), which attests to the high reproducibility of this procedure.

Comparison of in vitro and in vivo ChEC: Recruitment of TBP. The ChEC procedures provide a sensitive, high-resolution tool to study the recruitment of factors during gene activation or other dynamic nuclear processes. To explore this avenue, the TATA-binding protein (TBP, gene SPT15) was tagged with MN (TBP-MN) and used to study its recruitment to the GAL genes upon activation by galactose (Bryant and Ptashne, 2003). A strain was also prepared that carries a MN-tagged core histone H2b (H2b-MN, gene HTB2). This latter construct serves to reveal the nucleosomal ladder and the HS sites, since the resulting pattern was found to be similar to the one obtained by free MN. It was observed that strains expressing TBP-MN and H2b-MN fully support growth on galactose, indicating normal expression of GAL genes.

In vitro ChEC: The in vitro ChEC patterns of TBP-MN were examined at the GAL1-10 locus in cells grown with glucose (genes inactive) or with galactose (genes active). FIG. 4A shows that galactose leads to the appearance of strong cleavage fragments that cleanly map to the TATA box elements of this locus. Appearance of these bands is rapid and noted following a 15 second incubation at 30° C. with $Ca^{2+}$. In contrast, cleavage is absent or very weak under glucose growth at these sites. Examination of the latter pattern shows weak cutting at all the major HS (asterisk) sites. This "background" cleavage at HS sites observed in glucose grown cells is proposed to arise from a pool of TBP-MN that is non-limiting in yeast (Lee and Young, 1998), where cleavage at HS sites is due to their open-accessible chromatin structure.

FIG. 4A further shows the in vitro ChEC pattern of H2b-MN at the GAL1-10 locus obtained with glucose or galactose grown cells. Comparison of the two patterns of H2b-MN reveals some subtle differences. The glucose pattern of H2b-MN consists of a nucleosomal ladder that is superimposed by the more prominent HS bands (asterisk). In contrast, the HS sites of the galactose pattern nearly disappear and the nucleosomal ladder in the GAL10 gene is less pronounced (FIG. 4A). In general, H2b-MN cleavage is reduced at the entire locus as evidenced by the slower disappearance of the 6.3 kb PvuII fragment.

This observation is consistent with a transcription-dependent modification of chromatin structure and displacement of histones (Belotserkovskaya et al., 2004). It will be of great interest to follow up in greater detail the modification of the ChEC pattern of H2b-MN upon gene activation. It is reiterated that the H2b-MN patterns are very similar to those obtained with free MN (compare FIGS. 2A and 3B to FIG. 4A).

In vivo ChEC: In vivo ChEC data at the GAL1-10 locus was collected in parallel with the above experiment. In initial attempts to develop an in vivo ChEC procedure the ionophore calcimycin (A23187) was used to raise the intra-cellular $Ca^{2+}$ level in living cells. Although the attempts of the inventors were not exhaustive, addition of calcimycin to live cells induced only weak cleavage, probably due to the rapid transport of $Ca^{2+}$ into vacuoles. The inventors opted subsequently for a procedure that permeabilizes yeast cells to $Ca^{2+}$ ions with digitonin (Cordeiro and Freire, 1995). In this procedure digitonin is added to live cells for 5 minutes at 30° C. followed by the addition of $Ca^{2+}$ after chilling in ice. Careful inspection of the in vitro and in vivo patterns (FIGS. 4A and B) shows that they are virtually indistinguishable. The native pattern also demonstrates the galactose-dependent recruitment of TBP and the low-level cleavage bands at the HS sites in the glucose pattern that are thought to reflect the general binding of uncommitted TBP. Similarly, examination of the H2b-MN data also shows the weakening of the HS sites, a fuzzier nucleosomal ladder (GAL10 gene) and slower disappearance of the 6.3 kb PvuII fragment upon gene activation by galactose. These data inspire confidence that the ChEC method provides reliable information on the native chromatin state.

In summary, these experiments demonstrate that TBP is not poised at the TATA-boxes of the unexpressed GAL1-10 locus, but is dispersively bound. This general binding is detected as feeble cleavage at HS sites, where detection is most sensitive due to their open chromatin structure. Upon induction by galactose, TBP is recruited from general binding sites to sequence-specific binding at TATA boxes.

Comparison of in vitro and in vivo ChEC patterns of Sir3-MN. The next experiment applies ChEC to a spreading-type chromatin protein. The endogenous SIR3 was tagged (Sir3-MN) and analyzed by in vitro and in vivo ChEC (FIGS. 5A and 5B). DNA samples were not examined by indirect end-labeling, but probed without restriction digest. As expected, Sir3-MN yields a nucleosomal pattern at HML, but not at the non-silenced HIS3 locus (FIG. 5). The in vitro and in vivo ChEC patterns are again similar, but note the much slower cleavage reaction of Sir3-MN (long cleavage times) with fixed cells (FIG. 5A, in vitro ChEC). These experiments confirm the nucleosomal-type association of the Sir complex with silenced chromatin regions. Control experiments showed that H2b-MN cuts chromatin at HML and HIS3 with similar kinetics. These experiments suggest that isolated nucleosomal DNA, obtained by digestion with Sir3-MN or other spreading-type proteins, could serve to probe microarrays for genome-wide analyses of MN-tagged proteins.

Telomere Looping? It was also tested whether ChEC is suitable to study telomere conformation. Biochemical and expression studies suggested that telomeres form foldback loops mediated by the silencing proteins (de Bruin et al., 2001; Strahl-Bolsinger et al., 1997). The expression study showed that Gal4p can activate URA3 from a downstream UASg, if it is telomere-linked, while the same reporter at an internal genomic location remains inactive. This downstream-activation process was proposed to arise by silencing-dependent looping of Gal4p, bound downstream, to reach the upstream promoter.

Three strains with different telomere-linked URA3 constructs were studied. Strains MSY12 and MSY16 (not MSY11) contain UASg sites downstream of a telomere-linked URA3 (FIG. 6, maps). SIR3 was deleted in strain MSY16 to serve as a 'no looping' control. All strains expressed the tagged Gal4-MN gene and were grown in galactose containing media to ensure transactivation. It was expected that ChEC patterns might contain cuts around the promoter region, if looping occurs in the silenced strain MSY12. These cuts should be absent in the sir3Δstrain MSY16 (no looping) and in strain MSY11 (no UASg).

While no cleavage occurs in the control MSY11 strain (no UASg), the ChEC patterns of Gal4-MN reveal massive cutting at the UASg sites in the strains harbouring this element (FIG. 6A). This observation reiterates the impressive specificity of the ChEC method. Close examination of these patterns shows no detectable cutting throughout the URA3 gene using a probe that scans the DNA from an SspI site (at 1713 bp) toward the telomere.

To increase the sensitivity of detection, we carried out in vivo ChEC experiments that result in more extensive cleavage. FIG. 6B shows again specific cleavage at UASg sites. Note also that the full-length telomere band (1713 bp) is nearly completely digested in the UASg harboring strains (MSY12 & 16), while it remains uncleaved in the control strain (MSY11). This extensive cleavage reaction yields in the former two strains subsidiary cleavage bands throughout the URA3 gene that are absent in strain MSY11 (no UASg). Subsidiary cleavage, therefore, is UASg-dependent and is not arising as 'background' from uncommitted Gal4-MN proteins. Interestingly, the subsidiary pattern throughout URA3 is identical in the silenced (looped?) or non-silenced (non-looped?) strains MSY12 and MSY16, respectively. Hence, subsidiary cleavage through URA3 is dependent on the telomere-linked UASg, but is independent of silencing (looping?). It is important to point out that the subsidiary cleavage bands are very weak and are only observed after extensive digestion. By way of example, the band near the URA3 promoter (asterisk, FIG. 6B) amounts to only about 7% of the undigested band in strains MSY12 and MSY16.

Do telomeres mediate silencing-dependent cleavage at more distal location? The above DNA samples were probed from a Pst1 site (at 6991 bp) either toward the telomere and from there toward the centromere (up to 10671 bp). Again, such blots showed very similar subsidiary cleavage in the silenced and non-silenced strains.

The DNA samples of the telomere experiment were also analyzed at the GAL1-10 locus to control for the expression of Gal4-MN. All three strains showed similar cleavage at the 4 UASg sites in the GAL1-10 spacer region (FIG. 6C). Note that the UASg band at GAL7 is no longer visible due to extensive digestion in this experiment. As observed at telomeres, all three strains showed similar subsidiary cleavage in the GAL1 gene. These observations suggest that subsidiary cleavage is not a telomere-looping phenomenon but is also observed at internal loci.

These telomere experiments provide no evidence for a silencing-dependent, stable looping configuration with this artificial telomere constructs.

Discussion. New techniques according to the invention were presented to map the genomic interaction regions of chromatin proteins (summarized in Table I). The method called ChIC (chromatin immuno-cleavage) consists of tethering the fusion protein pA-MN (protein A fused to micrococcal nuclease) to antibodies that in turn are specifically bound to a chromatin protein. The MN moiety is kept in an inactive state during the tethering process by chelation of $Ca^{2+}$ ions. The method called ChEC (chromatin endogenous cleavage) consists of expressing fusion proteins in vivo, where MN is C-terminally fused to the coding region of a protein of interest. Importantly, the nucleolytic activity of MN remains inactive in vivo due to the low intracellular level of $Ca^{2+}$ ions. It is demonstrated that the activation of the nuclease tethered by either method with $Ca^{2+}$ ions, generates localized DNA breaks that mark the binding sites with excellent resolution.

Resolution: Double-stranded DNA cleavage of MN occurs preferentially at nucleosomal linker regions in chromatin and prominently at HS (hypersensitive) sites. This cleavage behaviour has important consequences for the resolution and specificity of the data. Theoretically, one would expect that a tethered MN cuts at a nearby nucleosomal linker or HS site. Indeed, close inspection of the ChEC results established that cleavage by the DNA-binding proteins TBP-MN, Gal4-MN and Gbd-MN occurs within about 100-200 bp of their known binding sites (FIGS. 3 and 4). Interestingly, the resolution of the ChIC data of Gbd-myc13 is similar despite the presence of the antibody and pA-MN linker proteins. This is evident from a comparison of the ChIC and ChEC patterns of Gbd-myc13 and Gbd-MN, respectively (FIGS. 2B and 3B). Even though the resolution achieved might vary for different target proteins and genomic loci, these data showed that the resolution of ChIC & ChEC is significantly better than that of ChIP (about 1000 bp, Orlando, 2000). The resolution is also better than that of the DamID method, which is based on the in vivo tethering of Dam methyltransferase to chromatin proteins (van Steensel and Henikoff, 2000). A model experiment established that Gbd-Dam mediates targeted methylation in a region of a few kilobases surrounding a UASg binding site.

Specificity and low-level cleavage at HS sites: Adequate specificity controls are of paramount importance to validate ChIC and ChEC patterns. One critical control for ChIC is the demonstration that retention of pA-MN by the crude nuclei is dependent on the myc-tagged antigens (FIG. 1B, Gbd-myc13 or Sir3-myc13). The ChIC data presented here, however, are directly validated by the observation that cleavage occurs predominantly at the expected binding sites. Hence, Gbd-myc13 mediates cleavage at the UASg sites and the silencing protein Sir3-myc13 leads to a nucleosomal pattern at the silenced HML locus but not at the non-silenced GAL1-10 locus (FIG. 2). A further important control showed that ChIC cleavage is absent with cells lacking a myc-tagged antigen (FIG. 2).

The Gbd-myc13 and Gbd-MN studies were carried out by overexpression (over 100-fold) of these proteins relative to the endogenous Gal4p. These experiments illustrate the potential specificity of ChIC and ChEC methods. Examination of the cleavage patterns of Gbd-myc13 and Gbd-MN show, as expected, strong cleavage at all UASg elements. But these digests also reveal low-level cutting at all HS sites that were defined by digestion with free MN and free pA-MN (FIGS. 2 and 3). Low-level cleavage is expected for overexpressed or naturally overabundant chromatin-bound proteins. Such proteins will not only bind specifically to a subset of sites, but due to their abundance, they will also interact non-specifically and dispersively along chromatin. Non-specific binding is thought to mediate the low-level bands at all HS, where chromatin is most easily cut. Importantly, cleavage at specific DNA elements is more prominent due to a higher occupancy. This assumption is validated for all sequence-specific proteins studied in this report.

The conclusion that low-level cleavage at HS sites is due to the overexpression of the Gbd proteins is based on studies with Gal4-MN. This gene was MN-tagged at its genomic location, where it is expressed at normal physiological level. Although Gal4-MN cleaves massively at its specific UASg sites, no significant low-level cutting at HS sites is observed (FIG. 3C). Supposedly, the low abundance of this protein only allows interactions with its specific UASg sites.

Caution: The above considerations illustrate that ChIC and ChEC experiments should preferably be carried out with target proteins expressed at normal physiological levels. It also illustrates that overabundant or overexpressed proteins, however, can be mapped (see Gbd-myc13 and Gbd-MN), since it is generally possible to distinguish between specific and general binding sites. Toward this end, it is of importance to carry out control digests with free pA-MN or free MN and to carefully compare such patterns to that obtained with ChIC or ChEC. Specific binding sites can be assigned to a genomic location with confidence where the control and ChIC/ChEC digests are significantly different. To define specific binding of spreading-type proteins, digestion patterns of free and tethered MN have to be compared at different loci.

Most DNA-binding proteins are known to interact at or cause HS sites. ChIC or ChEC experiments with such proteins, results in specific cleavage at a subset of HS sites only, while free MN (or pA-MN) cleaves (defines) all HS sites throughout the genome. Hence as above, comparison of the 'free' and 'tethered' cleavage patterns uniquely identifies the specific binding sites even if they overlap with HS sites.

Inclusion of a digest with free pA-MN is also important to generally examine the specificity of the ChIC technique. Poor antibody specificity or other experimental shortcomings will synergistically contribute to render the patterns of the free and tethered nuclease to be alike.

One basic assumption of the ChIC & ChEC technique is that the tethered MN moiety can reach the DNA, that is, can cleave. For target proteins that are part of a large complex, extension of the linker length between the target protein and pA to the MN moiety is probably necessary.

In vivo and in vitro ChEC: The ChIC and ChEC experiments discussed were carried out with fixed cells. The result section also includes comparison of the in vivo and in vitro ChEC pattern of TBP-MN at the GAL1-10 locus. These experimental variations differ simply in whether fixed or native cells are used prior to activation of MN. The observation that both ChEC patterns are nearly indistinguishable, demonstrates that both procedures are valid (FIGS. 4A and B).

Some low-level cutting was also observed at the HS sites in both ChEC patterns of the abundant TBP-MN protein. The HS sites in this experiment were determined by studying the digest obtained by the tagged histone H2b-MN. Such patterns were shown to be similar to that of free MN, that is, composed of prominent HS sites and a nucleosomal ladder.

Of interest is the comparison of the ChEC patterns of TBP-MN in the repressed or induced GAL1-10 locus. Activation of this locus by growth in galactose results in the massive recruitment of TBP-MN to the TATA-boxes, which are unoccupied in the repressed state (growth in glucose). This observation reiterates the notion that cleavage of specifically bound proteins is significantly enhanced. Of note are the subtle changes of the H2b-MN digest during locus activation. Experiments with MN-tagged transcription activators should permit detailed studies of the events leading to gene activation, especially a study of the chromatin perturbations mediated by targeted chromatin remodeling complexes with the help of MN-tagged histones.

A typical nucleosomal ladder is generated by Sir3-MN at the HML locus, where this silencing protein spreads along nucleosomes, if this digest is probed not by end-labeling, but by conventional Southern blotting (FIG. 5). Note again that Sir3-MN digestion is not observed if the same DNA samples are probed for the non-silenced HIS3 locus. These experiments also show that it is possible to isolate short nucleosomal DNA obtained by Sir3-MN digestion and use it as a probe to study the genomic distribution of this protein by probing microarrays. More generally, it is of great importance to explore experimental possibilities to extend the ChIC/ChEC methods to genome-wide analysis. One possible way would be to construct selective libraries that represent DNA fragments abutting the cleavage sites introduced by the tethered nuclease. One other procedure would be to enrich DNA fragments abutting MN cleavage sites and use those as probes for microarray analysis.

Indirect end-label and long-range: In most experiments presented in this example 1, DNA cleavage sites were measured by indirect end-labeling Southern blots. Exploiting this method, combined with the specificity of ChIC/ChEC, allows analysis on >10 kb regions in a single blot (e.g. FIG. 2A). In addition, repetitive sequences can be uniquely analyzed if a neighboring single-copy region is used as probe-binding site. One caveat of indirect end-labeling is that distal cleavage sites cannot be quantitatively detected if a strong cleavage site exists closer to the probe. In such cases, distally cut DNA is under-represented or becomes invisible. Shorter cleavage times, probing with the reciprocal distal probe or choosing other restriction enzyme/probe combinations are required to detect or confirm distal sites in such cases.

Telomere looping: Recent expression studies of a telomere-linked gene suggest that telomeres adopt looped structures dependent on the Sir silencing complex (de Bruin et al., 2001). Using a very similar experimental setup, Gal4-MN was targeted to UASg elements downstream of a telomere-linked URA3 gene. The ChEC pattern of Gal4-MN was then studied by indirect end-labeling in a telomere-proximal region in silenced and non-silenced strains (sir3Δ) and, a strain lacking UASg sites. The results showed massive UASg-dependent cleavage at this element. If telomere looping were a frequent conformation, then additional telomere-proximal cleavage bands should be observed in the silenced strain. The data revealed weak subsidiary and UASg-dependent cleavage throughout the analyzed 10.6 kb telomere-linked region. Interestingly, however, the subsidiary patterns are indistinguishable in the URA3 gene region shown in FIG. 6 and also the remainder of the sampled region. A number of control experiments were carried out (not shown). This includes the demonstration that the expression behavior of Gal4-MN is akin to that of Gal4p (de Bruin et al., 2001) and the notion that identical ChEC patterns were obtained with gal80Δ strains. This final control was carried out since de Bruin et al., used gal80Δ strains for their study.

These observations are difficult to reconcile with stable telomere loops. One possible explanation is that telomere looping is a rare, transient-stochastic event. Transient looping might occur frequently enough in silenced cells to allow downstream-activation of URA3, but be too rare to be biochemically detected by ChEC.

This telomere results illustrate the potential of the presented techniques and provocatively suggests that telomere conformation needs to be addressed with further structural tools, such as electron microscopy.

In summary, the data presented validate the experimental potential of the ChIC & ChEC methods. These tools should provide inroads toward a better elucidation of the epigenetic function of chromatin.

Experimental Procedures

Plasmids, Yeast Strains and Southern Probes

The coding region of the *Staphylococcus aureus* micrococcal nuclease (MN) was obtained by PCR from plasmid pFOG405 kindly provided by David Shortle and Wesley Stites (Shortle, 1983). The MN sequence used for all constructs encodes the mature chain of Nuclease A (amino acids 83 to 231 of Genbank P00644, SEQ ID No 1). The plasmid pK19pA-MN that drives expression of the pA-MN fusion protein in *E. coli* was cloned as follows: The MN coding sequence was PCR amplified and used to replace the EcoRI/BamHI fragment of plasmid pK19SEVII (Giraud-Panis et al., 1995). The pA moiety of pA-MN contains 2 IgG binding domains of staphylococcal protein A (amino acids 186 to 327 of Genbank AAA26676) that were fused to MN. The amino acid sequence of the pA and MN fusion region is daqapkDDDKEFatstkk (SEQ ID No 3) (the C-terminal sequence of pA is underlined, the short linker is in capitals and the N-terminus of MN is in italics). The yeast MN-tagging plasmids pFA6a-MN-KanMX6 and pFA6a-MN-His3MX6 were constructed as follows: The MN coding sequence was PCR amplified and used to replace in-frame the 3HA tag of plasmids pFA6a-3HA-KanMX6 or pFA6a-3HA-His3MX6 (Longtine et al., 1998). Gbd-MN and Gbd-myc13 were expressed from the plasmid pGBC11-MN and pGBC11-myc13, respectively. These are CEN plasmids that express Gbd fusion proteins under the control of the ADH1 promoter. pGBC11-MN was cloned by inserting the MN coding region into pGBC11 (Bartel et al., 1996). pGBC11-myc13 was constructed by insertion of a fragment containing 13 myc epitopes obtained from pFA6a-myc13-KanMX6 (Longtine et al., 1998) into pGBC11.

Epitope tagging and deletion of endogenous yeast genes was done by PCR-mediated gene disruption (Longtine et al., 1998). The MN-tagging cassettes presented here are used with the F2/R1 primers of the pFA6a-type plasmids (Longtine et al., 1998) and results in C-terminal fusion of MN to the target protein. A 7 amino acid linker encoded by the F2 primer separates target protein and MN-tag (amino acid sequence of the fusion: xRIPGLINatstkk (SEQ ID No 4) where the C-terminal amino acid of the target sequence is represented by an x, the linker is in capitals and the N-terminus of MN is in italics). Genotypes of the yeast strains used are shown in Table 3. Probes used for Southern blotting are described in Table 3.

pA-MN Expression and Purification

E. coli strain JM101 was transformed with pK19pA-MN and cultivated at 37° C. in NZYM medium containing 50 mg/l kanamycin. Expression of pA-MN was induced by adding 2 mM IPTG to exponentially growing cells. Bacteria from 200 ml culture were harvested after a 2 hour induction period, collected in 10 ml TEN (10 mM Tris-HCl pH 7.5, 1 mM EDTA, 150 mM NaCl) supplemented with 5 mM DTT. One mg of chicken egg white lysozyme (Sigma) was added and incubated for 10 minutes on ice. Cells were opened by sonication for 30 seconds using a Branson Sonifier 250 at output of 4. The extract was cleared by centrifugation for 20 minutes at 12000 rpm in a SS34 rotor (Beckman) at 4° C. Most of the pA-MN was recovered in the soluble supernatant (S1). pA-MN was purified from S1 using IgG-Sepharose 6 Fast Flow (Pharmacia) essentially as described by the manufacturer. 500 µl of cleared S1 were incubated with 15 µl drained IgG-Sepharose beads for 3 hours. Beads were washed twice with TEN supplemented with 0.03% Empigen (Empigen BB, Calbiochem); twice with TEN500 containing 0.03% Empigen (TEN supplemented with 500 mM NaCl) and once with 5 mM $NH_4Ac$ pH 5.0. pA-MN was eluted with 0.5 M $HAc/NH_4Ac$, pH 3.4. Eluates were neutralized using NaOH and glycerol added to a final concentration of 50%. Approximately 10 µg of highly purified protein were obtained per 1 ml starting culture. Long-time aliquots were stored at −70° C., short-term aliquots at −20° C.

DNA Isolation and Southern Blotting

DNA aliquots in 1× STOP of fixed samples were reverted by overnight incubation at 65° C. Fixed and unfixed samples were incubated with 20 µg proteinase K for 2 h at 50° C. DNA was extracted twice with phenol:chloroform:isoamylalcohol (25:24:1) and once with chloroform:isoamylalcohol (24:1). DNA was precipitated with 2× volume of absolute ethanol and washed with 70% ethanol. The DNA pellets were resuspended in TE (10 mM Tris-HCl, pH 7.5; 1 mM EDTA) containing 10-20 µg RNaseA and incubated for 1 hour at 37° C. Purified DNA was digested with restriction enzyme (indicated on the maps of the Figures), separated on native agarose gels and transferred to Hybond N+ membranes (Amersham) using alkaline capillary transfer. Membranes were Southern probed with $^{32}$P-labelled radioactive probes as described previously (Kas and Laemmli, 1992; Sambrook and Russell, 2001). Blots were analyzed using the Molecular Imager FX from Bio-Rad. Images were linearly contrast-stretched identically with ImageJ.

Immunoblotting

Protein aliquots were diluted 1:1 with 2× sample buffer (Laemmli, 1970), incubated for 10 minutes at 95° C. and cleared by centrifugation. Aliquots corresponding to 500 µl yeast culture were loaded per lane on a SDS-PAGE mini-gel (Bio-Rad) and proteins transferred to two nitrocellulose membranes by diffusion blotting (Bowen et al., 1980). Myc-tagged proteins were detected using mouse-α-myc antibody (9E10) and HRP-conjugated sheep-α-mouse antibodies (RPN4201, Amersham). To visualize antibodies and pA-MN, the membranes were probed using rabbit-α-mouse (ab8516, Abcam Ltd.) as primary and HRP-conjugated goat-α-rabbit (172-1019, Bio-Rad) as secondary antibody.

TABLE 2

Yeast strains

| Strain | Genotype | Reference |
|---|---|---|
| KIY54 | W-1303B hml::E-4xUASg-ADE2-4xUASg-URA3-I | Ishii and Laemmli, 2003 |
| KIY64 | W303-1B ade2-1::his3 hml::E-4xUASg-ADE2-4xUASg-URA3-I | unpublished[a] |
| KIY67 | W303-1B ade2-1::his3 hml::E-4xUASg-ADE2-4xUASg-URA3-I SIR3-myc13:kan | unpublished[a] |
| YDS631 | W303-1B adh4::URA3-($C_{1-3}$A)n | Chien et al., 1993 |
| YDS634 | W303-1B adh4::URA3-4xUASg-($C_{1-3}$A)n | Chien et al., 1993 |
| TD345 | W303-1B ade2-1::his3 hml::E-4xUASg-ADE2-4xUASg-URA3-I SIR3-MN:kan | this study |
| TD347 | W303-1B ade2-1::his3 hml::E-4xUASg-ADE2-4xUASg-URA3-I HTB2-MN:kan | this study |
| TD348 | W303-1B ade2-1::his3 hml::E-4xUASg-ADE2-4xUASg-URA3-I SPT15-MN:kan | this study |
| MSY04 | W303-1B adh4::URA3-4xUASg-($C_{1-3}$A)n sir3::kan | this study |
| MSY11 | W303-1B adh4::URA3-($C_{1-3}$A)n GAL4-MN:His3 | this study |
| MSY12 | W303-1B adh4::URA3-4xUASg-($C_{1-3}$A)n GAL4-MN:His3 | this study |
| MSY16 | W303-1B adh4::URA3-4xUASg-($C_{1-3}$A)n sir3::kan GAL4-MN:His3 | this study |
| KIY141 | W303-1B hml::E-URA3-4xUASg-l | unpublished[a] |
| KIY47 | S288C hml::E-URA3-I | unpublished[a] |

[a]Unpublished yeast strains were kindly provided by Kojiro Ishii

Cultivation, fixation and isolation of crude nuclei. Yeast strains expressing Gbd-myc13 or Gbd-MN (transformed with pGBC11 plasmids) were grown in SC-TRP media. Yeast strains expressing endogenous genes were grown in YPAD media. For regulation of the GAL genes, cells were grown in YPAR (YPA containing 2% raffinose). One hour before harvesting, expression was induced by adding 2% galactose or repressed by adding 2% glucose. Strains expressing Gal4-MN were grown in YPAR containing 2% galactose to assure expression of a trans-activating form of Gal4p. All cultures were grown at 30° C. and harvested at an $OD_{600}$ of about 0.6.

Fixation was done by adding 1% paraformaldehyde to cultures at room temperature for 20 minutes. The reaction was stopped by the addition of 125 mM glycine (final) for 5 minutes. Cells were harvested, washed 3 times in YPAD and frozen at −70° C. All subsequent manipulations were performed on ice except stated otherwise. Protease inhibitors (PBPi) are added to all buffers at the following final concentration: PMSF (P) 1 mM, Benzamidine (B) 1 mM and the PI cocktail containing 10 µg/ml chymostatin, pepstatin A and leupeptin hemisulfate each. The letters P, B and Pi are used to indicate these inhibitors in the different buffers.

Crude nuclei were prepared from fixed, frozen cell pellets (50 ml of culture) as follows. Cells were washed 3 times by microfuge centrifugation in 1 ml of buffer A-P (15 mM Tris-HCl pH 7.4, 0.2 mM spermine, 0.5 mM spermidine, 80 mM KCl, 2 mM EDTA supplemented with PMSF). Cells were opened with about 400 µl of glass-beads (kept at −20° C.) in 350 µl of buffer A-PBPi using a Genie Vortex for 10 to 15 minutes until all cells are broken and glass-beads removed.

TABLE 3

Southern probes

| Probe | Genomic Position[a] | Origin | Used in FIG. |
|---|---|---|---|
| HML-I | chr III 14024-14454 | Restriction fragment from plasmid pHML-e-i-UAS-SIH[c] | 2A |
| GAL | chr II 279343-279834 | PCR fragment using yeast genomic DNA as template | 2B, 3B & C, 4A & B, 6C |
| HML-E | chr III 11226-11508 | PCR fragment using yeast genomic DNA as template | 3A |
| HML-long | [b] | 6.2 kb NotI/BgII fragment from pHML-E/I-U-ADE-U-URA[c] | left panels 5A & B |
| HIS3 | chr XV 721848-722629 | Restriction fragment from plasmid pHML-e-i-UAS-SIH[c] | right panels 5A & B |
| adh4 | chr VII 15849-16302 | Restriction fragment from plasmid E210[c] | 6A & B |

[a]chromosome number and homology to the *Saccharomyces cerevisiae* genome (*Saccharomyces* Genome Database, release 03 Mar. 2004; Cherry et al., 1998)
[b]contains fragments of HML-E and I silencer elements and the ADE2 and URA3 gene
[c]Ishii and Laemmli, 2003

Chromatin Immuno-Cleavage (ChIC)

Crude nuclei obtained by breakage with glass beads were washed once with 1 ml HEENT-PBPi (20 mM Hepes pH 7.5; 5 mM EDTA-K; 5 mM EGTA-K; 100 mM NaCl; 0.05% Tween 20, supplemented with PBPi inhibitors). Centrifugation for these and all subsequent washing steps were done in 1.5 ml Eppendorf tubes for 2 minutes at 13000 rpm in a cooled Biofuge (Heraeus). All steps were carried out at 4° C. Crude nuclei were blocked for 5 minutes with HEENT-PBPi containing 3% BSA and then for 5 minutes with blocking buffer (HEENT-PBPi containing 0.1% acetylated BSA (Aurion BSA-c™)).

Step 1: Following the blocking steps, crude nuclei were incubated on a rotating wheel for 2 hours in 500 µl blocking buffer containing 4 µg anti-myc mouse monoclonal antibody 9E10 (Santa Cruz Biotechnology). Excess antibody was removed with 3 washing steps in 1 ml wash buffer (HEENT-P).

Step 2: Pellets from step 1 were incubated for 1 hour in 500 µl blocking buffer containing 6 µg rabbit anti-mouse (RAM) antibody (ab8516, Abcam Ltd.) followed by 3 washes in 1 ml wash buffer.

Step 3: Pellets from step 2 were incubated for 1 hour in 500 µl blocking buffer containing 3 µg of purified pA-MN. Crude nuclei were stringently washed 2 times in 1 ml wash buffer, 2 times in 1 ml wash buffer containing 500 mM NaCl and incubated twice for 5 minutes in 1 ml wash buffer at 30° C.

Step 4: Pellets were resuspended in 600 µl digestion buffer (20 mM Hepes pH 7.5; 0.1 mM EGTA; 100 mM NaCl, 1 mM PMSF). A 150 µl aliquot (zero time point, $-Ca^{2+}$) was removed and mixed with an equal volume of 2×STOP solution (2% SDS; 400 mM NaCl; 20 mM EDTA; 4 mM EGTA; 0.2 µg/µl glycogen). 80 µl of a slurry of drained IgG Sepharose was then added to bind traces of free pA-MN. The IgG Sepharose beads had been previously washed as described by Pharmacia and equilibrated in digestion buffer. Digestion was as follows: Crude nuclei containing IgG Sepharose beads were spun and resuspended in 400 µl of digestion buffer supplemented with 2 mM $CaCl_2$ and incubated at 30° C. under gentle agitation. At indicated time points, 150 µl aliquots were taken from the mixture and immediately mixed with an equal volume of 2×STOP solution. Digestion with free pA-MN was done with blocked crude nuclei removed prior to step 1. These crude nuclei were washed once in digestion buffer and an aliquot (zero time point, $-Ca^{2+}$) removed. Nuclei were resuspended in digestion buffer containing 2 mM of $CaCl_2$. 300 ng pA-MN was added to roughly match tethered pA-MN and digestion was carried out at 30° C. for the indicated time.

In Vitro ChEC: Chromatin Endogenous Cleavage on Fixed Cells

Fixed cells were broken by glass-beads as described above, washed with 1 ml of buffer A-PBPi and resuspended in 450 µl of buffer Ag-PBPi (buffer A lacking EDTA but containing 0.1 mM EGTA). A 150 µl aliquot (zero time point, $-Ca^{2+}$) was mixed with an equal volume of 2×STOP. 2 mM $CaCl_2$ was added to the remaining suspension and gently stirred at 30° C. Aliquots were taken at the indicated times and mixed with an equal volume of 2×STOP. Controls were digested by addition of titrated amounts (0.5 units) of MNase (Sigma) to the digestion reaction.

In Vivo ChEC: Chromatin Endogenous Cleavage of Native Cells

Cells from 50 ml culture were grown to $OD_{600}$ of about 0.6, harvested and washed 3 times in 1 ml of buffer A-PBPi. Cells were permeabilized in 600 µl of buffer Ag-PBPi containing 0.1% digitonin by incubation for 5 minutes at 30° C. and agitation. Samples that were digested on ice (H2b-MN and TBP-MN) were chilled before the addition of $Ca^{2+}$. To induce cleavage 2 mM $CaCl_2$ (final) was added and incubated at 30° C. or on ice under gentle agitation. Aliquots were taken before and after addition of $Ca^{2+}$ at indicated times by mixing with an equal volume of 2×STOP lacking SDS. For DNA extraction, cells were broken using glass beads and 1% SDS (final) was added thereafter.

Example 2

'Solid State' SS-CHIC

In the ChIC procedure detailed in example 1, the binding and washings steps were carried out in suspension by centrifugation (Schmid et al., 2004). To shorten processing times, improve specificity (better washing) and achieve a number of additional improvements (below), the inventors have carried out the ChIC procedure by 'solid-state' (ss-ChIC), where chromosomes, nuclei or permeabilized cells are attached to glass coverslips. This is akin to staining protocols for immunofluorescence (IF, FIG. 7). In contrast to IF, it is necessary to reversibly attach large amounts of DNA (about 10 µg of DNA) per coverslip to allow Southern blotting. It is however to be noted, that it is possible to work with less material by using PCR amplification (see example relating to the genome-wide procedure).

Preliminary experiments established that polylysine-coated coverslips were found to be inadequate for ss-ChIC, due to loss of material during the washing steps. Different techniques were explored to tether the biological material more firmly to coverslips. One simple, common method is to dip the loaded coverslips into cooled (−20° C.) methanol for 20 minutes. This is followed by rehydration and the staining protocol. A second method is to pre-coat the coverslips with commercially available "polyphenolic proteins" (BD Cell-Tak™) essentially according to the manufactures procedure. Initial experiments established that cellular material (cells, nuclei, chromosomes, chromatin fragments) adhering to such coated coverslips is not lost during the ensuing staining procedure. It is to be noted that the Cell-Tak™ technique avoids the methanol de-/re-hydration steps that can lead to loss of antigenicity.

Mapping the *Drosophila* BEAF Protein Using ss-ChIC:

FIG. 7A outlines a generic ss-ChIC procedure, as exampled for nuclei (for detailed method, see below). Isolated, fixed *Drosophila* Kc nuclei were deposited to coated coverslips and incubated with the specific, primary Abs, anti-BEAF and separately, anti-dBarren. Following the washing steps, incubation was continued with pA-MN and subsequent to further washing steps, cleavage was induced and stopped by addition of $Ca^{2+}$ and EGTA, respectively. These steps were carried out while coverslips floated on small drops of buffers deposited on a Parafilm. It is to be noted that this protocol could be carried out with different chromatin-containing material and may include additional steps, e.g. a secondary Ab to enhance the binding of pA-MN.

FIG. 7B shows an immuno-blot of the proteins (indicated) bound following the final step. Such blots serve an important quality control to ascertain the specific retention/tethering of the pA-MN. Hence, it served to optimize ss-ChIC procedure. Examination of the data establishes that pA-MN is only retained, if a primary AB (anti-BEAF or dBarren) was added (indicated at top). A BEAF antibody was used to develop this blot, consequently, this antigen (not dBarren) is observed in all lanes.

FIG. 7C shows the specific mapping of BEAF to scs'. This element defines one of the boundaries of the heat-shock locus (see map, bottom and is a known target region for BEAF (Zhao et al., 1995). Specific binding of BEAF to scs' is experimentally manifested by cleavage bands (indicated) that map to this element. An indirect end-labeling procedure was applied to develop this Southern blot; the probe used, a SalI-EcoR1 fragment, is indicated. A novel binding site (about 8 kb distal) was also discovered in this experiment. Whereas the ChIC experiments presented in example 1 are all performed with yeast, the experiment shown in this example 2 demonstrates that ChIC works with remarkable specificity with higher eukaryotes containing complex genomes.

Advantages of ss-ChIC: The advantages of this procedure are ease of handling, rapidity of procedure, higher specificity and the opportunity to carry our optical quality controls, in addition to immuno-blotting. The latter point refers to optical examination (e.g. by fluorescence microscopy) of the specific retention of pA-MN using Abs. Importantly, ss-ChIC can be carried-out with all biological material that is immuno-stainable; this includes tissue sections obtained from biopsies. One further main advantage of ss-ChIC is that it can be carried with minute amounts of biological material in combination with PCR amplification.

Detailed procedure: Round coverslips (diameter 18 mm) were cleaned with ethanol, dried and coated with BD-Cell Tak™ according to the manufacturer's description. 55 µl of Kc nuclei ($OD_{260}$ about 64 per ml), isolated as described previously (Mirkovitch et al., 1984), were diluted in 3.5 ml of $HEEg_1N_{100}TP$ and after 15 minutes fixed with freshly prepared PAF (paraformaldehyde) at final concentration of 2%; all operations at room temperature. Fixation was stopped following 20 minutes by the addition of glycine (2.5 M) to a final concentration of 0.125 M. The fixed nuclei (550 µl) were then deposited by centrifugation on each of the 7 coated coverslips; roughly 10-20 µgr is estimated to be bound per support.

Coverslips were blocked with 300 µl of $HEEg_1N_{100}TP$ supplemented with 5% no-fat milk powder (Rapidlait, Migros, Switzerland) for 15 minutes. This and all subsequent reactions were carried out while coverslips floated on 300 µl drops that were deposited on Parafilm. It is important to note that this blocking step with no-fat milk is very critical (BSA is inefficient) to prevent non-specific association of the ABs and pA-MN. Following the blocking steps, the incubation was continued with 1000-fold diluted anti-sera for BEAF and dBarren for 2 hours in blocking solution. Thereafter, coverslips were washed, 4 times for 5 minutes using with $HEEg_1N_{100}TP$. Incubation with pA-MN (final about 1 µgr/ml) was performed in $HEEg_{100}N_{50}TP$ for 1 hour. Washing steps thereafter were 2 times 5 minutes for each of the following solutions: $HEEg_{100}N_{50}TP$, $HEEg_1N_{500}TP$ and finally $HEEg_1N_{100}TP$. Two coverslips were used for analysis by SDS gel electrophoresis. Toward this end, the proteins were eluted during 3 minutes with 90 µl FSB, while the coverslips were deposited on a hotplate (about 100 C°). The remaining coverslips were processed for DNA digestion (5 minutes) by incubation with 250 µl of $HEEg_{100}N_{100}TP$ supplemented with 5 mM $CaCl_2$. Digestion by the tethered MN was stopped with drops of 250 µl of STOP. Fixation by PAF was reverted by overnight incubation at 65° C., this was followed by the addition protease K (final 0.400 mgr/ml) and an additional incubation for 2 hours at 50° C. To prevent evaporation and facilitate sample recovery, the latter two operations were carried out with the coverslips deposited in tight-fitting round buckets made in a Teflon slab (volume about 3 ml) that could be sealed tightly with an O-ring lined lid. DNA was finally extracted by standard phenolic extractions and ethanol precipitation.

Buffers:

$HEEg_1N_{100}TP$: 20 mM Hepes pH 7.5, 1 mM EDTA, 1 mM EGTA, 100 mM NaCl, 0.05% Tween-20 and 1 mM PMSF (freshly added).

$HEEg_{100}N_{50}TP$: as $HEEg_1N_{100}TP$ but containing instead 100 mM EGTA and 50 mM NaCl.

$HEEg_1N_{500}TP$: as $HEEg_1N_{100}TP$ but containing instead 500 mM NaCl.

$HEEg_{0.1}N_{100}TP$: as $HEEg_1N_{100}TP$ but containing 0.1 mM EGTA.

STOP: 20 mM EDTA, 4 mM EGTA, 440 mM NaCl, 2% SDS, pH about 7.5.

FSB, final sample buffer (Laemmli, 1970): 0.0625 M Tris/HCl pH 6.8, 2% SDS, 10% glycerol, 5% β-merceptaethanol and 0.001% bromophenol blue.

Example 3

Genome-Wide (gw) ChIC & ChEC

Indirect end-labeling and Southern blotting are used to map the genomic locations of chromatin proteins in the procedures of example 1. The inventors have extended this method to a genome-wide (gw) analysis, where tiling microarrays, encompassing entire genomes or chromosomes, are probed with gw-probes.

To prepare gw-probes, it is necessary to isolate the DNA fragments abutting MN cuts (boxed, FIG. 8A). The restriction enzyme Mbo I, a frequent cutter, is used to trim the DNA flanking MN-cuts (depicted). The isolation and amplification protocol of this flanking DNA is outlined in panels B & C of FIG. 8 (see also legend of FIG. 8).

Example 3A

Mapping Gal4-MN to the Gal Locus Using gw-Probes and Dot Blotting

Several experiments established that gw-probes are specifically enriched for known sequences. One experiment is shown with yeast *Saccharomyces cerevisiae*, where GAL4p interaction sites (Gal4-MN) were mapped by probing dot blots encompassing the GAL locus and controls. FIG. 9 contains two dot blot filters A and B. The top row of each filter contains PCR-fragments encompassing the GAL locus. The middle rows contain spots spanning the rDNA repeat, where GAL4p does not bind. Loading controls were spotted in the bottom rows. The location of the PCR-fragments in the GAL locus is depicted with vertical lines in the map of panel C.

Filter A serves as the control and was hybridized with the zero-minute (0' probe, no Gal4-MN digestion) probe. Filter B shows the blot obtained with the one-minute (1' Gal4-MN digestion) probe; it serves to map Gal4-MN.

It is to be noted that the control rows (rDNA locus and loading controls) hybridize equally well to the zero and one-minute probes (compare filters A and B). In contrast, the one-minute probe (filter B) hybridizes with impressively enhanced intensity to dots (boxed) that encompass Gal4p binding sites (by comparison of top rows of each filter).

These gw-probes were prepared as described in FIG. 8, wherein Mbo I digestion is used to trim the flanking DNA. Hence, as is expected and is observed, the intensities of all dots between the known binding sites up to the flanking Mbo I sites are enhanced (underlined in the map), if hybridized with the one-minute probe (Filter B). This experiment and several others established that the amplification protocol works. Microarray experiments presented next confirm and extend this notion.

Example 3B

Genome-Wide Interaction of the Nucleopore Receptor Nup2P

GAL locus: This experiment improve the understanding of the role of the nucleopore complex (NPC) in gene expression. Nup2p is a receptor of the nuclear basket of the NPC and previous experiments identified this protein as transient gene activation/desilencing station (Ishii et al., 2002, Ishii & Laemmli, 2003). To dissect this intriguing phenomenon further, Nup2 was MN tagged (Nup2-MN) with the goal to map its genomic interaction sites.

Using a Nup2-MN expression strain, the inventors first studied the GAL locus of the yeast *Saccharomyces cerevisiae* by the conventional ChEC approach, detailed in example 1. The GAL locus contains three well-characterized genes that are repressed by glucose and strongly activated by galactose. The present studies established that Nup2-MN does interact with the genome in a highly selectively manner; the inventors have observed that Nup2-MN cleaves the promoter-regulatory region of the GAL genes specifically, if these genes are activated by galactose.

Galactose-Dependent Cleavage at HXK1:

This experiment has been carried out to determine whether genes routinely interact with the Nup2p receptor of the nuclear basket. Toward this aim, gw-probes were hybridized to Affymetrix tiling arrays that encompass chromosome VI of yeast (other chromosomes are not available to this date). Chromosome VI contains a glucose-repressed, galactose-activate gene, HXK1, encoding the hexokinase isoenzyme. Gw-probes were prepared from Nup2-MN expressing cells grown in glucose or galactose. Prior to the microarray experiments discussed next, the inventors determined by conventional blotting that Nup2-MN cleaves the HXK1 promoter in a galactose-dependent manner (FIG. 10). Examination of this data shows that Nup2-MN cleaves specifically at the HXK1 promoter (arrowhead) in the galactose (but not glucose) samples.

Figure 11A:
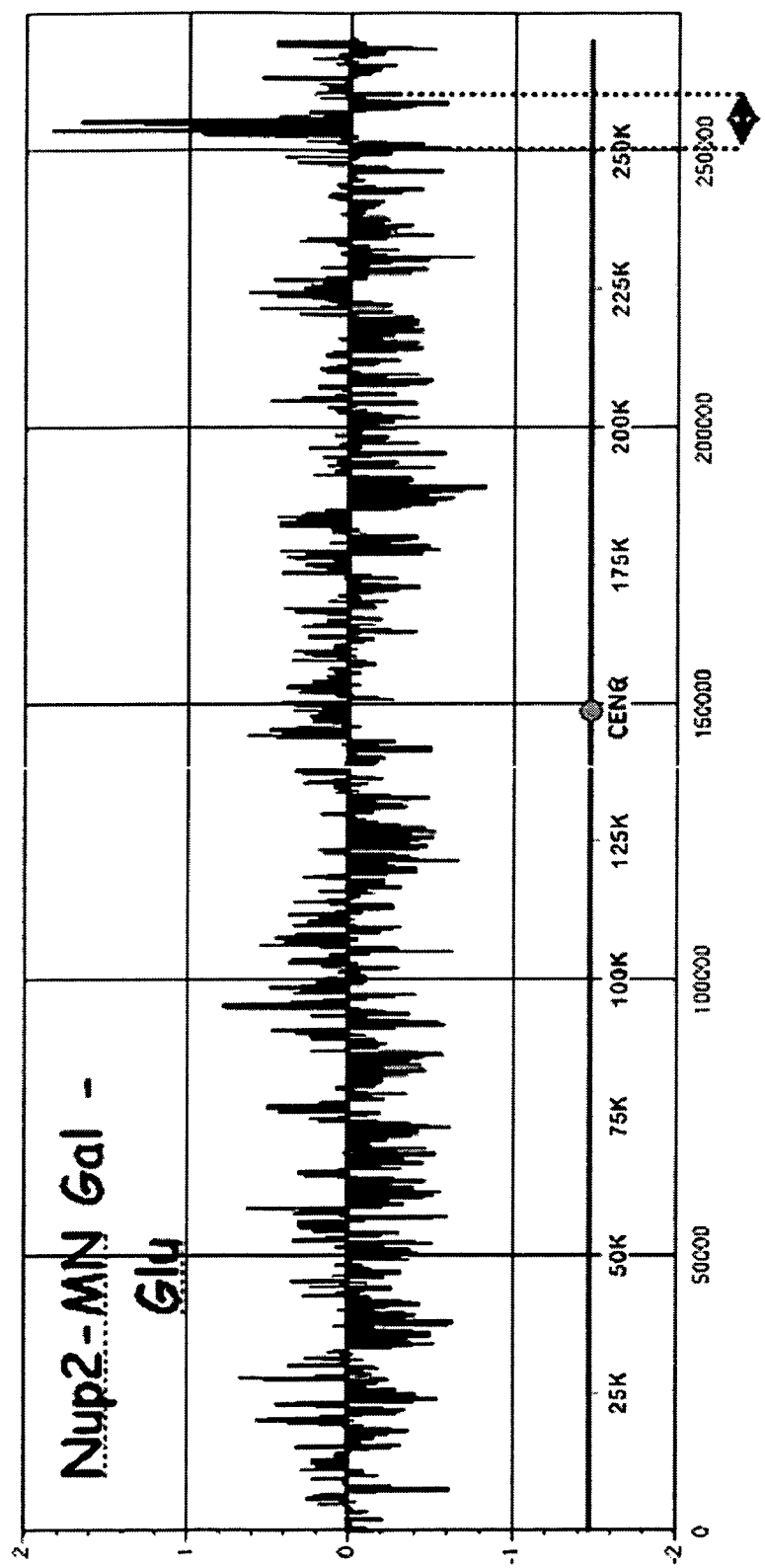

Galactose-Dependent Microarray Pattern:

The microarray data confirm this observation. FIG. 11A shows the results at low-resolution throughout chromosome VI. The vertical bars represent the ratio of the hybridization signals of the gw-probes (digestion 5 minutes) prepared from galactose over glucose-grown cells. This plot identifies a single major peak at the HXK1 gene. Hence, specific Nup2-MN cleavage at HXK1 in a galactose-dependent manner is also observed by microarray analysis.

Figure 11B:
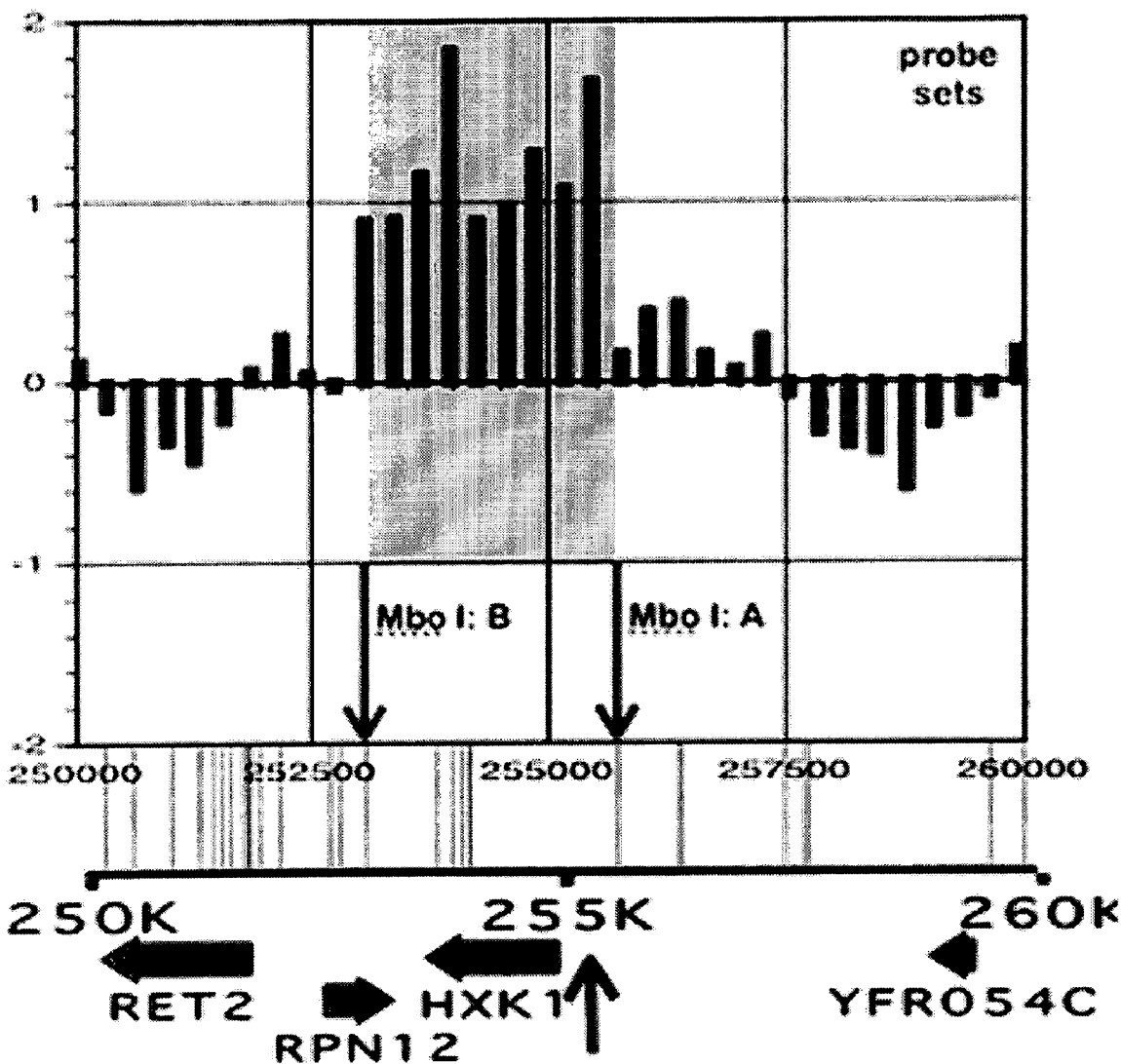

FIG. 11B, shows the same data at higher resolution around the HXK1 gene. It is to be noted that Mbo I digestion was used to trim the DNA flanking during the preparation of the gw-probes. Careful examination of the map shows a sharp drop of the positive signal toward the right of the Mbo I site A (arrow). This is expected, since theoretically the gw-probe encompasses DNA from the Nup2-MM cut (arrow) to this Mbo I site (A). Similarly as expected, all features throughout the gene up to the Mbo I site B are also enriched. The positive signals (boxed grey) extend past the next downstream Mbo I site and continue until site B downstream of HXK1. Hence, in addition to the strong cleavage site at the promoter, Nup2-MN cuts are supposed to occur also within and downstream of HXK1. This region was not precisely mapped by indirect end-labeling.

Figure 11C:
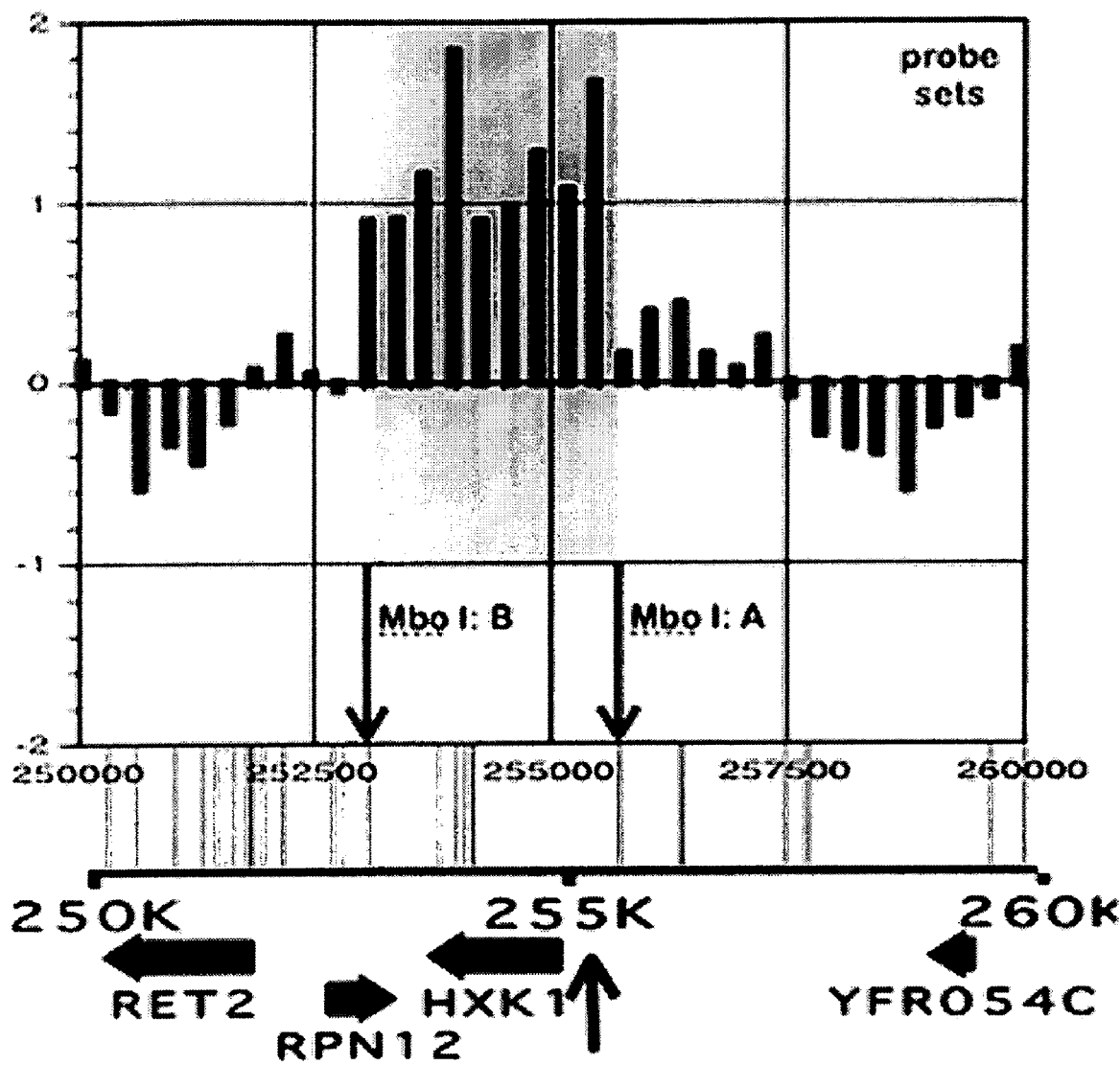

The data presented in FIG. 11B were presented using averaged values for probe-sets comprising up to 16 probes (see Methods), where the signals from the individual oligonucleotides (25 bases), called features, encompassing a probe-set are represented by a single value. FIG. 11C shows the data of panel B at a single probe resolution. That is, the signal of each individual feature is displayed. Examination of this presentation impressively establishes that the data is valid down to each individual feature. In addition, a sharp drop of the positive signals (boxed grey) coincides precisely with the flanking Mbo I sites (arrows, Mbo I: A & B). This and additional data demonstrated that the resolution of the gw-approach could be improved to single feature analysis.

This experiment nicely validates the genome-wide approach technically and demonstrates that activation-dependent interaction of Nup2-MN with the promoter not only occurs at the GAL locus, but also at the HXK1 gene. It also illustrates that it would be valuable to prepare higher resolution gw-probes (below), since unusually distant Mbo I sites (exampled by sites A & B at HXK1) can result in loss of resolution.

Constitutive Nup2-MN-to-Promoter Interaction:

Putative constitutive interactions of Nup2-MN were examined genome-wide along chromosomes VI. Gw-probes were prepared from Nup2-MN expressing cells and cells expressing the MN-tagged histone gene HTB2 (H2b-MN). This latter construct serves an important function to correct the gw-data for a bias introduced by nuclease hypersensitivity. As discussed in some detail previously in example 1, the extent of cleavage by a tethered MN moiety at a given locus is not only dependent on the fractional occupancy of that site by the tagged protein, but also depends on DNA accessibility. That is, it is well established that chromatin contains nuclease hypersensitive sites (HS), where cleavage is much more pronounced than at bulk loci. This correction is necessary since data obtained with gw-probes, if uncorrected, would be biased for regions with HS sites. The inventors have previously established that mild/brief cleavage by H2b-MN serves to localize HS sites in vivo (see example 1, see also FIG. 13).

FIG. 12A shows the uncorrected gw-data for Nup2-MN encompassing the 50-100 kb region of chromosome VI. The plot shown represents the ratio of the hybridization signals obtained with the 5 minute over the zero-minute (undigested) probes. Hence, positive values mark regions where Nup2-MN cleaves. The middle panel B represents the data for H2b-MN, where the ratios of the hybridization signals obtained with the one-minute over the zero-minute probe (undigested) are plotted. Positive peaks mark HS sites (see also FIG. 13). The bottom panel C shows the Nup2-MN data corrected for H2b-MN by substraction. Included in this presentation are standard deviation error bars from three independent experiments that attest to the impressive reproducibility of the data.

Examination of the corrected data establishes that Nup2-MN interactions occurs throughout the genome and occur nearly exclusively at promoter-containing intergenic regions. This is consistent with the data obtained by indirect end-labeling Southern blots of the GAL locus and the HXK1 genes (FIG. 10). Prominent examples obtained with the gw-approach are the divergent genes FRS2-GAT1, FYV1-FRS2 and RIM15-YFL030W. To ascertain the validity of the gw-data, a number of regions were also analyzed by indirect end-labeling and Southern blotting.

FIG. 13 compares the H2b-MN pattern to that of Nup2-MN at the ACT1 and at the FRS2 and GAT1 genes. The H2b-MN data reveals predominantly the HS sites (open arrowheads). Consistent with the microarray results, the Nup2-MN pattern is clearly different to the pattern of H2b-MN. Nup2-MN cleaves a number of bands that coincide with H2b-MN sites, although some of those appear with enhanced intensity in Nup2-MN (filled arrowheads). In addition, the Nup2-MN pattern contains several novel bands (asterisks) that are absent in H2b-MN pattern. Importantly, the novel and enhanced Nup2-MN bands coincide with the ACT1 and FRS2 and GAT1 promoter regions. These results confirm the gw-data (FIG. 12C), and establish congruency of both techniques. It can thus be concluded that Nup2-MN interacts with many promoter-intergenic regions and only very rarely with coding or 3' regions.

Analysis by conventional blotting also validates the HS correction applied to the gw-data. By way of example, the H2b-MN pattern of ACT1 (FIG. 13) reveals a major HS site 3' of this gene (open arrowhead). This same site is marked by a major peak in the gw-analysis of H2b-MN (FIG. 13B, open arrowhead), which is also observed in the uncorrected Nup2-MN data (FIG. 13A). In contrast, this peak, which clearly marks at HS site, is removed in the corrected presentation (FIG. 12C, open arrowhead).

Improving GW-Probes:

Resolution: The average resolution with Mbo I is theoretically about 254 by and is determined by the genomic sequence. Although this resolution is often adequate, it is possible to improve it by trimming the flanking DNA closer to the MN-cuts (see FIG. 10). One possibility is to use a nuclease that cuts in a random fashion (eg. DNase I), followed by the isolation of the DNA fragment abutting the MN-cut similarly as described in step 4 FIG. 8C. Another option is to employ a linker containing a recognition sequence for a class II restriction enzyme, such as EcoP15I (CAGCAGN$_{25}$) (SEQ ID No 5). Cleavage of the bead-bound DNA with this enzyme (instead of Mbo I) would result in probes, where the flanking DNA is composed of about 27 bp. This shortened DNA could be amplified using an appropriate B linker. The tiling microarrays from Affymetrics contain features harboring nucleotides of 25 bases. Hence, gw-probes containing 27 bases of genomic DNA should theoretically map MN-cuts to about 2 features.

Specificity: It might be desirable to improve the signal to noise ratio of the gw-probes. An important source of background may arise from MN-like breaks that are introduced mechanically during DNA isolation. These breaks then serve as acceptors sites for primer A. One possible procedure to reduce this mechanical background, would be to deliberately fragment DNA prior to isolation with DNase I (or another nuclease), under conditions where double-stranded breaks (Mn$^{++}$) are created. Such deliberate 'nicking' can then be blocked as described in FIG. 9 and further mechanical fragmentation can be avoided due to the already reduced DNA fragment size.

Material & Methods for Genome Wide ChIC & ChEC:

Yeast Strains and Culture Conditions:

Yeast strain expressing H2b-MN and Nup2-MN were created by MN-tagging the endogenous HTB2 and NUP2 loci as described previously (Schmid et al., 2004). These loci were modified in the yeast strain KIY54 (Schmid et al., 2004). The genotypes are: H2b-MN strain (W-303B hml::E-4×UASg-ADE2-4×UASg-URA3-1HTB2-MN:kan); Nup2-MN strain (W-303B hml::E-4×UASg-ADE2-4×UASg-URA3-I NUP2-MN:kan).

Yeast cells were cultivated and induced by glucose and galactose as described (Schmid et al., 2004).

In Vivo ChEC and Analysis by Indirect End-Labeling Southern Blot:

In vivo ChEC was done as described (Schmid et al., 2004). ChEC cleavage times were 0 minutes, 1 minute and 2 minutes on ice for H2b-MN and 0 minutes, 5 minutes and 10 minutes at 30° C. for Nup2-MN.

DNA was isolated from in vivo ChEC experiments as described and the DNA concentration measured after RNase A digestion.

DNA was analyzed by indirect end-labeling using Southern blotting as described (Schmid et al., 2004). Restriction digests for mapping by indirect end-labeling were as follows: for HXK1 with XbaI, for ACT1 and the FRS2/GAT1 region with EcoRI. The probes used were amplified from genomic DNA by PCR and correspond to the following genomic position on S. cerevisiae chromosome VI: HXK1: 255'476 to 255'999; ACT1: 55441 to 55925; FRS2/GAT1: 93890 to 94417.

Enrichment of MN-Cut Proximal DNA Fragments from ChEC DNA:

1) Blocking by Adding a ddNTP with TdT:

Free DNA 3'-OH ends, called nicks, were blocked by a reaction with a dideoxynucleotide (ddNTP) mixture and the enzyme terminal deoxynucleotidyl transferase (TdT). Blocking was done in a 30 µl final reaction volume, which was assembled as follows: 6 µl 5× TdT Reaction buffer; 6 µl 25 mM $CoCl_2$; 0.6 µl 400 U/µl recombinant TdT (all three reagents were from Roche, Terminal Transferase, recombinant); 1.5 µl ddNTPs (1 mM each ddATP, ddGTP, ddCTP, ddTTP; Roche); about 750 ngr of ChIC- or ChEC-derived DNA and $dH_2O$ to 30 µl. Reaction period was 2 hours at 37° C.

Reactions were stopped by adding 60 µl TE (10 mM Tris-Cl pH 8.0; 1 mM EDTA) and 1 µl 0.5 M EDTA and heat inactivated for 10 minutes at 70° C. DNA was precipitated by adding 12 µl 3 M Na-acetate and 240 µl ethanol, left for 10 minutes at −70° C. and spun 15 minutes at 16'000 g at 4° C. The pellets were washed with 70% ethanol and dried.

2) Phosphorylation of MN-Cut Ends with PNK:

MN doubled-stranded cuts contain 5'-OH/3'-Phosphate groups. These ends were converted to 5'-phosphate/3'-OH using T4 Polynucleotide Kinase (T4 PNK) in the presence of ATP. The DNA pellets following the blocking step 1 were resuspended in 20 µl (final) PNK reaction solution assembled with: 2 µl 10×DNA Ligase buffer (NEB); 0.4 µl T4 PNK (10 U/µl, NEB); 17.6 µl $dH_2O$. Incubation was for 1 hour at 37° C., T4 PNK was heat-inactivated at 70° C. for 15 minutes.

3) Ligation of the Linker $A^{Biotin}$:

Fifty µM of linker $A^{Biotin}$ was prepared by annealing the oligonucleotides 5'Biotin-ATTGGCGCGCCTAAG-CAGTCC-3'OH (SEQ ID No 6) and 5'OH-GGACTGCT-TAGGCGCGCCA-3'H (SEQ ID No 7) at 50 µM each in TE by heating to 94° C. and slow cooling to 4° C. The annealed primers were reused and stored at −20° C.

To the mixture after step 2 contained, 2 µl A-Ligation mix (0.2 µl 10×DNA Ligase buffer (NEB); 0.2 µl 100 mM ATP; 0.8 µl linker $A^{Biotin}$ (50 µM); 0.8 µl of T4 DNA ligase (400 U/µl, NEB)) were added, mixed and incubated for 20 hours at 16° C.

Excess, unligated linker $A^{Biotin}$ was removed by repeated precipitation using polyvinylalcohol (PVA) in the presence of high salt. Precipitation cycles were done by resuspending (or adjusting) the DNA to 150 µl $T_{40}E_1N_{2000}$ (40 mM Tris-Cl pH7.5; 1 mM EDTA; 2000 mM NaCl) and mixed with 150 µl of 10% PVA in $dH_2O$ (Polyvinylalcohol avg. MW=30-70 kD; Sigma). The mixture was left 15 minutes on ice and spun 10 minutes at 16'000 g. DNA was reprecipitated 4 times by resuspension in 150 µl $T_{40}E_1N_{2000}$ and addition of 150 µl of 10% PVA. The final DNA pellets were washed 10 minutes on ice with 70% ethanol and dried.

4) Mbo I Restriction Digest:

The DNA pellets after step (3) were resuspended in 50 µl Mbo I mix (5 µl 10× Magic buffer, 0.5 µl Mbo I (5U/µl, NEB); 44.5 µl $dH_2O$) and incubated for >12 h at 37° C. Magic buffer contains: 20 mM Tris/HCl, pH 7.4, 0.05 mM spermidine, 0.125 mM spermine, 20 mM KCl, 70 mM NaCl, 10 mM $MgCl_2$, and 0.1% digitonin.

5) Capture of Biotinylated DNA with Magnetic Beads:

To the MboI digestion reaction were added: 100 µl 10% PVA; 100 µl 5 M NaCl; 25 µl 1 M Tris-Cl pH 7.5; 2 µl 0.5 M EDTA; 25 µl of washed Dynabeads® M-280 Streptavidin in TE and 200 µl $dH_2O$. Binding of biotinylated DNA was done for 6 hours at room temperature (RT) under gentle rotation. The beads were then washed using a magnet (Dynal MPC) 3 times with 1 ml $T_{40}E_1N_{2000}$, twice with 1 ml and once with 300 µl $T_{30}Mg_{10}$ (30 mM Tris-Cl, pH 8; 10 mM $MgCl_2$).

6) Ligation of Linker B:

Fifty µM linker B was prepared by annealing the oligo-nucleotides 5'OH-GGTCCATCCAACC-3'OH (SEQ ID No 8) and 5'Phosphate-GATCGGTTGGATGGACCG-3'OH (SEQ ID No 9) as described in step (3) for linker $A^{Biotin}$.

Washed beads after step 5 were resuspended in 30 µl (final) B-Ligation mixture assembled as follows: 3 µl 10× T4 DNA Ligase buffer (NEB); 0.6 µl T4 DNA Ligase (400 U/µl; NEB); 0.75 µl Adaptor B (50 µM) and 25.65 µl $dH_2O$. Incubation was for 12 hours (or more) at 16° C. under gentle rotation. Beads were then washed with 1 ml $T_{40}E_1N_{2000}$ and 1 ml TE, resuspended in 30 µl TE and stored at −20° C.

7) PCR $1^{st}$ Round, Master-PCR:

A 25 µl Master-PCR reactions were performed using the DNA bound to Dynabeads after step 6 as a template. The reaction contained: 2.5 µl template (resuspended Dynabeads from step 7); 1 µl primers An/Bn (25 µM each; An: 5' GCGC-CTAAGCAGTCC 3' (SEQ ID No 10), Bn: 5' GGTCCATC-CAACCGAT 3') (SEQ ID No 11); 12.5 µl 2×Taq PCR Master Mix (Qiagen); 1 µl 25 mM $MgCl_2$ and $dH_2O$ to 25 µl. PCR conditions: 94° C. 90 seconds; 30 cycles of 94° C. 20 seconds—60° C. 30 seconds-68° C. 3 minutes; 72° C. 5 minutes.

Microarray Analysis:

PCR $2^{nd}$ Round:

The microarray probe was amplified from the Master-PCR in a 100 µl PCR reaction: 4 µl template (Master-PCR from step 7); 4 µl primers An/Bn (25 µM each; see above except that for the $2^{nd}$ round a 5' biotinylated version of primer An was used); 50 µl 2× Taq PCR Master Mix (Qiagen); 4 µl 25 mM $MgCl_2$ and $dH_2O$ to 100 µl. PCR conditions: 94° C. 90 seconds; 20 cycles of 94° C. 20 seconds-60° C. 30 seconds-68° C. 3 minutes; 72° C. 5 minutes.

DNase I Digestion and $ddATP^{Biotin}$ Labeling of DNase Fragments:

The DNA from PCR from step 8 was purified and concentrated by dilution with $dH_2O$ to 500 µl and concentrating 5 to 10 fold through a Microcon YM-30 Centrifugal Filter Device (Amicon/Millipore). The retentate was again filled to 500 µl with $dH_2O$ and concentrated to less than 40 µl. The final retentate was adjusted to 40 µl with $dH_2O$; digested with DNase I and labeled with $TdT/ddATp^{Biotin}$ as described previously (Katuo et al., 2003).

Hybridization and Analysis of DNA Tiling Microarrays:

Prehybridization, hybridization, washing, staining and scanning of S. cerevisiae chromosome VI tiling arrays (rik-DACF, P/N 510636, Affymetrix) was done as described previously (Katuo et al., 2003). Microarray data were analyzed using the open source software "Bioconductor" (Gentleman et al., 2004; www.bioconductor.org; version 1.5). For the statistical analysis, probes were grouped into probe sets comprising 16 probes or less in a way that a probe set does never overlap an MboI site. Signal log 2 values for probe sets were calculated by the robust multi-array average (RMA) algorithm using the Bioconductor software. Probe set log 2 ratio=RMA-value (exp 1)−RMA-value (exp 2). Signal log 2 ratios for single probes were calculated by extracting single probe values from perfect match probes. Single probe log 2 ratio=log 2(Signal 1)−log 2(Signal 2).

REFERENCES

Bartel, P. L., Roecklein, J. A., SenGupta, D., and Fields, S. (1996). A protein linkage map of Escherichia coli bacteriophage T7. Nat Genet 12, 72-77.

Belotserkovskaya, R., Saunders, A., Lis, J. T., and Reinberg, D. (2004). Transcription through chromatin: understanding a complex FACT. Biochim Biophys Acta 1677, 87-99.

Bowen, B., Steinberg, J., Laemmli, U. K., and Weintraub, H. (1980). The detection of DNA-binding proteins by protein blotting. Nucleic Acids Res 8, 1-20.

Bryant, G. O., and Ptashne, M. (2003). Independent recruitment in vivo by Gal4 of two complexes required for transcription. Mol Cell 11, 1301-1309.

Cherry, J. M., Adler, C., Ball, C., Chervitz, S. A., Dwight, S. S., Hester, E. T., Jia, Y., Juvik, G., Roe, T., Schroeder, M., et al. (1998). SGD: Saccharomyces Genome Database. Nucleic Acids Res 26, 73-79.

Chien, C. T., Buck, S., Sternglanz, R., and Shore, D. (1993). Targeting of SIR1 protein establishes transcriptional silencing at HM loci and telomeres in yeast. Cell 75, 531-541.

Cordeiro, C., and Freire, A. P. (1995). Digitonin permeabilization of Saccharomyces cerevisiae cells for in situ enzyme assay. Anal Biochem 229, 145-148.

de Bruin, D., Zaman, Z., Liberatore, R. A., and Ptashne, M. (2001). Telomere looping permits gene activation by a downstream UAS in yeast. Nature 409, 109-113.

Gentleman R C, Carey V J, Bates D M, Bolstad B, Dettling M, Dudoit S, Ellis B, Gautier L, Ge Y, Gentry J, Hornik K, Hothorn T, Huber W, Iacus S, Irizarry R, Leisch F, Li C, Maechler M, Rossini A J, Sawitzki G, Smith C, Smyth G, Tierney L, Yang J Y and Zhang J. *Bioconductor: open software development for computational biology and bioinformatics*. Genome Biology 2004, 5(10), R80.

Giraud-Panis, M. J., Duckett, D. R., and Lilley, D. M. (1995). The modular character of a DNA junction-resolving enzyme: a zinc-binding motif in bacteriophage T4 endonuclease VII. J Mol Biol 252, 596-610.

Harlow, E., and Lane, D. (1999). Using antibodies: a laboratory manual (Cold Spring Harbor, N.Y., Cold Spring Harbor Laboratory Press).

Irizarry R A, Hobbs B, Collin F, Beazer-Barclay Y D, Antonellis K J, Scherf U, Speed T P. *Exploration, normalization, and summaries of high density oligonucleotide array probe level data*. Biostatistics 2003, 4(2), 249-64.

Ishii, K., et al., Chromatin boundaries in budding yeast: the nuclear pore connection. Cell, 2002. 109(5): p. 551-62.

Ishii, K., and Laemmli, U. K. (2003). Structural and dynamic functions establish chromatin domains. Mol Cell 11, 237-248.

Kas, E., and Laemmli, U. K. (1992). In vivo topoisomerase II cleavage of the *Drosophila* histone and satellite III repeats: DNA sequence and structural characteristics. Embo J 11, 705-716.

Katou Y, Kanoh Y, Bando M, Noguchi H, Tanaka H, Ashikari T, Sugimoto K and Shirahige K. *S-phase checkpoint proteins Tof1 and Mrc1 form a stable replication-pausing complex*. Nature 2003, 424, 1078-1083.

Laemmli, U. K. (1970). Cleavage of structural proteins during the assembly of the head of bacteriophage T4. Nature 227, 680-685.

Lee, T. I., and Young, R. A. (1998). Regulation of gene expression by TBP-associated proteins. Genes Dev 12, 1398-1408.

Lee, J.-S., Lee, C.-H. and Chung, J. H. (1998); Studying the recruitment of Sp1 to the β-globin promoter with an in vivo method: Protein position identification with nuclease tail (PIN*POINT). Proc. Natl. Acad. Sci. USA 95, 969-974

Longtine, M. S., McKenzie, A., 3rd, Demarini, D. J., Shah, N. G., Wach, A., Brachat, A., Philippsen, P., and Pringle, J. R. (1998). Additional modules for versatile and economical PCR-based gene deletion and modification in *Saccharomyces cerevisiae*. Yeast 14, 953-961.

Mirkovitch, J. Mirault, M-E. and Laemmli, U. K. Cell, 1984, 39, 223-232.

Natsoulis, G., and Boeke, J. D. (1991). New antiviral strategy using capsid-nuclease fusion proteins. Nature 352, 632-635.

Orlando, V. (2000). Mapping chromosomal proteins in vivo by formaldehyde-crosslinked-chromatin immunoprecipitation. Trends Biochem Sci 25, 99-104.

Rusche, L. N., Kirchmaier, A. L., and Rine, J. (2003). The establishment, inheritance, and function of silenced chromatin in *Saccharomyces cerevisiae*. Annu Rev Biochem 72, 481-516.

Sambrook, J., and Russell, D. W. (2001). Molecular cloning: a laboratory manual, 3rd edn (Cold Spring Harbor, N.Y., Cold Spring Harbor Laboratory Press).

Schmid M., Durussel T. and Laemmli U. K. ChIC and ChEC: Genomic Mapping of Chromatin Proteins. Molecular Cell 2004, 16, 147-157.

Shortle, D. (1983). A genetic system for analysis of staphylococcal nuclease. Gene 22, 181-189.

Strahl-Bolsinger, S., Hecht, A., Luo, K., and Grunstein, M. (1997). SIR2 and SIR4 interactions differ in core and extended telomeric heterochromatin in yeast. Genes Dev 11, 83-93.

Telford, D. J., and Stewart, B. W. (1989). Micrococcal nuclease: its specificity and use for chromatin analysis. Int J Biochem 21, 127-137.

van Steensel, B., Delrow, J., and Henikoff, S. (2001). Chromatin profiling using targeted DNA adenine methyltransferase. Nat Genet 27, 304-308.

van Steensel, B., and Henikoff, S. (2000). Identification of in vivo DNA targets of chromatin proteins using tethered dam methyltransferase. Nat Biotechnol 18, 424-428.

Zhao, K. Hart, C. M. and Laemmli, U. K. Cell, 1995, 81, 879-889.

The invention claimed is:

1. A method for localizing within a chromosome or a DNA, the DNA binding loci of a chromatin binding protein or a DNA binding protein comprising the following steps:
   a) linking, directly or indirectly, to said chromatin binding protein or said DNA binding protein, an enzyme with regulatable activity, wherein the enzyme is capable of introducing into said chromosome or said DNA a detectable modification; and is in an inactive state when so linked;
   b) contacting the chromosome or the DNA with the chromatin binding protein or the DNA binding protein to which the enzyme is linked from step a);
   c) transiently activating the regulatable activity of the enzyme bound to the chromatin binding protein or the DNA binding protein so that the enzyme introduces the detectable modification into the chromosome or the DNA; and
   d) mapping on the chromosome or the DNA the location of the enzymatic modification introduced by the enzyme into said chromosome or said DNA so as to thereby localize within the chromosome or the DNA, the DNA binding loci of the chromatin binding protein or the DNA binding protein.

2. The method of claim 1, wherein the enzyme activity is regulatable by addition and suppression of an effector.

3. The method of claim 1, wherein the enzyme is a nuclease with regulatable nucleolytic activity and wherein the enzymatic modification comprises a cleavage site in the chromosome or DNA.

4. The method according to claim 1, wherein the transient activation lasts less than 2 hours.

5. The method according to claim 1, wherein the duration of transient activation is reduced by raising the temperature.

6. The method according to claim 1, wherein steps a), b) and c) are carried out in vitro.

7. The method according to claim 6, wherein steps a), b), and c) are carried out in a cell-free system.

8. The method according to claim 6, wherein steps a), b), and c) are carried out on formaldehyde-fixed nuclei or on extracted chromatin.

9. The method according to claim 1, wherein steps a), b), and c) are carried out in vivo.

10. The method according to claim 1, wherein steps a), b), and c) are carried out in solutions.

11. The method according to claim 1, wherein the chromosome or DNA is fixed on a solid support and wherein steps a), b), and c) are carried out in solid state.

12. The method according to claim 11, wherein the chromosome or DNA is covalently fixed on the solid support.

13. The method according to claim 11, wherein the solid support is coated with chemicals which react with the chromosome or DNA.

14. The method according to claim 13, wherein the chemicals are bifunctional chemicals.

15. The method according to claim 11, wherein the chromosome or DNA is attached to the solid support.

16. The method of claim 11, wherein the solid support is a glass coverslip.

17. The method according to claim 1, wherein the linking in step a) of the enzyme with regulatable activity to the chromatin binding protein or the DNA binding protein is carried out indirectly via one or more antibodies.

18. The method according to claim 3, wherein the nuclease is part of a fusion protein comprising another domain.

19. The method according to claim 18, wherein said another domain is staphylococcal protein A (pA), staphylococcal protein G (pG), or an antibody.

20. The method according to claim 17, wherein the antibodies are one or more of polyclonal antibodies, tagged antibodies or biotinylated antibodies.

21. The method according to claim 17, wherein the chromatin binding protein or the DNA binding protein is tagged.

22. The method according to claim 17, wherein the linking in step a) is carried out by:
   binding to said chromatin binding protein a primary antibody specific for the chromatin binding protein or for a tag bound to said protein,
   targeting a second antibody against the first antibody, and
   binding the second antibody with a fusion protein comprising the nuclease.

23. The method according to claim 3, wherein the linking in step a) of the nuclease to the chromatin binding protein or the DNA binding protein is carried out by expressing a fusion protein comprising said nuclease in an inactive state and the chromatin binding protein or the DNA binding protein.

24. The method according to claim 23, wherein the chromatin binding protein or the DNA binding protein is N-terminal with respect to the nuclease, in the fusion protein.

25. The method according to claim 23, wherein the chromatin binding protein or the DNA binding protein is C-terminal with respect to the nuclease, in the fusion protein.

26. The method according to claim 23, wherein the chromatin binding protein or the DNA binding protein is internally embedded in the fusion protein.

27. The method according to claim 23, wherein the nuclease of the fusion protein is introduced into the gene locus of the chromatin binding protein or the DNA binding protein by homologous recombination.

28. The method according to claim 23, wherein the fusion protein is expressed from a plasmid.

29. The method according to claim 23, wherein the fusion protein further comprises a linker between the nuclease and the chromatin binding protein or the DNA binding protein.

30. The method according to claim 3, wherein the nuclease is a micrococcal nuclease having the sequence set forth in SEQ ID NO:1 or a nuclease having at least 70% sequence identity with said SEQ ID NO:1.

31. The method according to claim 2, wherein the enzyme with regulatable activity is activated by influx of $Ca^{2+}$ ions.

32. The method according to claim 31, wherein, for in vivo embodiments, influx of $Ca^{2+}$ is obtained by permeabilization of the cells or by use of an ionophore.

33. The method according to claim 32, wherein the enzyme with regulatable activity is rendered inactive by quenching $Ca^{2+}$ by addition of EGTA or another chelating agent.

34. The method according to claim 1, wherein the chromosome or DNA is from a cell or a cell-free system.

35. The method according to claim 34, wherein the cell is a prokaryotic cell.

36. The method according to claim 34, wherein the cell is from a lower eukaryote.

37. The method according to claim 34, wherein the cell is from a higher eukaryote, a mammal or a human.

38. The method according to claim 3, wherein the mapping of the cleavage site is carried out by one or more of indirect end labelling, PCR or primer extension.

39. The method, wherein the specificity of the localisation of binding loci of the chromatin binding protein or the DNA binding protein is improved by deducting the non-specific general binding sites along the chromosome or the DNA from the binding loci mapped by the method of claim 1.

40. The method according to claim 39, wherein the non-specific general binding sites are determined by carrying out the method with a histone protein as the chromatin binding protein or with an unlinked, regulatable enzyme nuclease.

41. The method according to claim 39, wherein the non-specific binding sites are nuclease hypersensitive sites.

42. The method of claim 3, wherein the mapping of step d) is carried out by determining the extent of digestion of a given chromatin fragment with a probe specific for that chromatin fragment.

43. The method according to claim 1, wherein the mapping of step d) is carried out on an entire chromosome (chromosome-wide scale), an entire genome (genome-wide scale) or on specific DNA fragments.

44. The method according to claim 43, wherein the enzyme with regulatable activity is a nuclease and wherein the mapping on the entire chromosome or on the entire genome, is carried out by hybridizing DNA fragments abutting the location of the enzymatic modification DNA cleavage sites introduced by the nuclease to DNA encompassing the entire chromosome or genome.

45. The method according to claim 44, wherein said step d) comprises the following steps:
(i) preventing the nicks found in the DNA or chromosome from re-ligating,
(ii) rendering break sites introduced by the nuclease capable of ligation with a linker,
(iii) ligating a linker to said break sites,
(iv) digesting the chromosome or DNA with a restriction enzyme, and
(v) using the digested chromosome or DNA fragments comprising said linker from step (iv) as a hybridization probe to hybridize to DNA encompassing the entire chromosome or genome.

46. The method according to claim 3, wherein the mapping of the cleavage site is achieved with an array.

47. The method according to claim 46, wherein the array is a microarray or dot-blot.

48. The method according to claim 46, wherein the array is a tiling-microarray.

49. The method according to claim 46, wherein the array comprises genomic DNA, cDNA, DNA comprising chromatin binding regions, DNA comprising regulatory regions, RNA, or RNA comprising chromatin binding regions.

50. A method for determining whether a given protein binds to a chromosome or a DNA of a cell at a given specific locus in the chromosome or the DNA comprising:
a) linking a nuclease in an inactive state to said given protein,
b) contacting the chromosome or the DNA from said cell with the protein to which the nuclease is linked from step a)
c) transiently activating the nuclease in the presence of the chromosome or the DNA from said cell, and
d) detecting whether a cleavage site has been introduced into the chromosome or the DNA at the given specific locus.

51. A method of screening for proteins which are capable of binding to a chromosome or a DNA of a cell at a given, specific locus comprising:
a) linking a nuclease in an inactive state to said proteins,
b) contacting the chromosome or the DNA from said cell with the proteins to which the nuclease is linked from step a)
c) transiently activating the nuclease in the presence of the chromosome or the DNA from said cell, and
d) detecting whether a cleavage site has been introduced into the chromosome or the DNA at the given, specific locus.

52. A method for localising on a chromosome or a DNA, the binding loci of a chromatin binding protein or a DNA binding protein comprising the following steps:
a) fixing the chromosome or the DNA;
b) binding to the chromatin binding protein or the DNA binding protein, a primary antibody specific to the chromatin or DNA binding protein;
c) binding to the primary antibody, a second antibody specific for the primary antibody;
d) contacting the fixed chromosome or DNA of step a) with the chromatin binding protein or the DNA binding protein to which the primary antibody is bound and to which primary antibody the second antibody of step c) is bound;

e) adding a regulatable nuclease in an inactive state, fused to a domain having an affinity for the primary antibody or for the second antibody;
f) transiently adding $Ca^{2+}$ to activate the regulatable nuclease;
g) detecting whether a cleavage site has been introduced into the chromosome or the DNA by the regulatable nuclease; and
h) mapping on the chromosome or the DNA the cleavage site introduced by the nuclease into the chromosome or the DNA;

wherein steps b) to d) are carried out in a buffer containing an agent chelating the $Ca^{2+}$ ion, and wherein the cleavage site mapped on the DNA or the chromosome is the binding loci of the chromatin binding protein or the DNA binding protein.

53. The method according to claim 1, wherein the transient activation in step c) lasts less than 10 minutes.

54. The method according to claim 1, wherein the transient activation in step c) lasts less than 5 minutes.

55. The method according to claim 1, wherein the transient activation in step c) lasts less than 1 minute.

56. The method according to claim 1, wherein the transient activation in step c) lasts less than 30 seconds.

* * * * *

SEQUENCE LISTING

<160> NUMBER OF SEQ ID NOS: 11

<210> SEQ ID NO 1
<211> LENGTH: 149
<212> TYPE: PRT
<213> ORGANISM: Staphylococcus aureus

<400> SEQUENCE: 1

Ala Thr Ser Thr Lys Lys Leu His Lys Glu Pro Ala Thr Leu Ile Lys
1               5                   10                  15

```
Ala Ile Asp Gly Asp Thr Val Lys Leu Met Tyr Lys Gly Gln Pro Met
            20                  25                  30

Thr Phe Arg Leu Leu Val Asp Thr Pro Glu Thr Lys His Pro Lys
        35                  40                  45

Lys Gly Val Glu Lys Tyr Gly Pro Glu Ala Ser Ala Phe Thr Lys Lys
    50                  55                  60

Met Val Glu Asn Ala Lys Lys Ile Glu Val Glu Phe Asp Lys Gly Gln
65                  70                  75                  80

Arg Thr Asp Lys Tyr Gly Arg Gly Leu Ala Tyr Ile Tyr Ala Asp Gly
                85                  90                  95

Lys Met Val Asn Glu Ala Leu Val Arg Gln Gly Leu Ala Lys Val Ala
                    100                 105                 110

Tyr Val Tyr Lys Pro Asn Asn Thr His Glu Gln His Leu Arg Lys Ser
                115                 120                 125

Glu Ala Gln Ala Lys Lys Glu Lys Leu Asn Ile Trp Ser Glu Asp Asn
130                 135                 140

Ala Asp Ser Gly Gln
145

<210> SEQ ID NO 2
<211> LENGTH: 142
<212> TYPE: PRT
<213> ORGANISM: Staphylococcus aureus

<400> SEQUENCE: 2

Ser Leu Lys Asp Asp Pro Ser Gln Ser Ala Asn Leu Leu Ser Glu Ala
1               5                   10                  15

Lys Lys Leu Asn Glu Ser Gln Ala Pro Lys Ala Asp Asn Lys Phe Asn
            20                  25                  30

Lys Glu Gln Gln Asn Ala Phe Tyr Glu Ile Leu His Leu Pro Asn Leu
        35                  40                  45

Asn Glu Glu Gln Arg Asn Gly Phe Ile Gln Ser Leu Lys Asp Asp Pro
    50                  55                  60

Ser Gln Ser Ala Asn Leu Leu Ala Glu Ala Lys Lys Leu Asn Asp Ala
65                  70                  75                  80

Gln Ala Pro Lys Ala Asp Asn Lys Phe Asn Lys Glu Gln Gln Asn Ala
                85                  90                  95

Phe Tyr Glu Ile Leu His Leu Pro Asn Leu Thr Glu Glu Gln Arg Asn
                100                 105                 110

Gly Phe Ile Gln Ser Leu Lys Asp Asp Pro Ser Val Ser Lys Glu Ile
            115                 120                 125

Leu Ala Glu Ala Lys Lys Leu Asn Asp Ala Gln Ala Pro Lys
130                 135                 140

<210> SEQ ID NO 3
<211> LENGTH: 18
<212> TYPE: PRT
<213> ORGANISM: Artificial Sequence
<220> FEATURE:
<223> OTHER INFORMATION: chemically synthesized

<400> SEQUENCE: 3

Asp Ala Gln Ala Pro Lys Asp Asp Lys Glu Phe Ala Thr Ser Thr
1               5                   10                  15

Lys Lys
```

```
<210> SEQ ID NO 4
<211> LENGTH: 14
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: Xaa = unknown

<400> SEQUENCE: 4

Xaa Arg Ile Pro Gly Leu Ile Asn Ala Thr Ser Thr Lys Lys
 1               5                  10

<210> SEQ ID NO 5
<211> LENGTH: 31
<212> TYPE: DNA
<213> ORGANISM: Artificial Sequence
<220> FEATURE:
<223> OTHER INFORMATION: chemically synthesized
<220> FEATURE:
<221> NAME/KEY: misc_feature
<222> LOCATION: (7)..(31)
<223> OTHER INFORMATION: n = any nucleotide

<400> SEQUENCE: 5
cagcagnnnn nnnnnnnnnn nnnnnnnnnn n                           31

<210> SEQ ID NO 6
<211> LENGTH: 21
<212> TYPE: DNA
<213> ORGANISM: Artificial Sequence
<220> FEATURE:
<223> OTHER INFORMATION: chemically synthesized

<400> SEQUENCE: 6
attggcgcgc ctaagcagtc c                                      21

<210> SEQ ID NO 7
<211> LENGTH: 19
<212> TYPE: DNA
<213> ORGANISM: Artificial Sequence
<220> FEATURE:
<223> OTHER INFORMATION: chemically synthesized

<400> SEQUENCE: 7
ggactgctta ggcgcgcca                                         19

<210> SEQ ID NO 8
<211> LENGTH: 13
<212> TYPE: DNA
<213> ORGANISM: Artificial Sequence
<220> FEATURE:
<223> OTHER INFORMATION: chemically synthesized

<400> SEQUENCE: 8
ggtccatcca acc                                               13

<210> SEQ ID NO 9
<211> LENGTH: 18
<212> TYPE: DNA
<213> ORGANISM: Artificial Sequence
<220> FEATURE:
<223> OTHER INFORMATION: chemically synthesized

<400> SEQUENCE: 9
gatcggttgg atggaccg                                          18
```

-continued

```
<210> SEQ ID NO 10
<211> LENGTH: 15
<212> TYPE: DNA
<213> ORGANISM: Artificial Sequence
<220> FEATURE:
<223> OTHER INFORMATION: chemically synthesized

<400> SEQUENCE: 10
gcgcctaagc agtcc                                                          15

<210> SEQ ID NO 11
<211> LENGTH: 16
<212> TYPE: DNA
<213> ORGANISM: Artificial Sequence
<220> FEATURE:
<223> OTHER INFORMATION: chemically synthesized

<400> SEQUENCE: 11
ggtccatcca accgat                                                         16
```